US010653600B2

(12) United States Patent
Geffroy et al.

(10) Patent No.: US 10,653,600 B2
(45) Date of Patent: May 19, 2020

(54) COSMETIC COMPOSITION COMPRISING A SUPRAMOLECULAR COMPOUND CAPABLE OF ESTABLISHING HYDROGEN BONDS, AND TWO PARTICULAR DISTINCT SILICONE OILS

(75) Inventors: Nathalie Geffroy, Verrieres le Buisson (FR); Roberto Cavazzuti, Paris (FR); Sylvie Manet, Verrieres le Buisson (FR); Florence Lahousse, Thiais (FR)

(73) Assignee: L'OREAL, Paris (FR)

( * ) Notice: Subject to any disclaimer, the term of this patent is extended or adjusted under 35 U.S.C. 154(b) by 220 days.

(21) Appl. No.: 14/128,989

(22) PCT Filed: Jun. 14, 2012

(86) PCT No.: PCT/EP2012/061308
§ 371 (c)(1),
(2), (4) Date: Jul. 11, 2014

(87) PCT Pub. No.: WO2012/175402
PCT Pub. Date: Dec. 27, 2012

(65) Prior Publication Data
US 2014/0328783 A1 Nov. 6, 2014

(30) Foreign Application Priority Data

Jun. 23, 2011 (FR) ...................................... 11 55576

(51) Int. Cl.
*A61Q 1/06* (2006.01)
*A61K 8/49* (2006.01)
*A61K 8/891* (2006.01)

(52) U.S. Cl.
CPC ............ *A61K 8/4953* (2013.01); *A61K 8/891* (2013.01); *A61Q 1/06* (2013.01); *A61K 2800/40* (2013.01)

(58) Field of Classification Search
None
See application file for complete search history.

(56) References Cited

U.S. PATENT DOCUMENTS

2003/0035781 A1* 2/2003 Minami ................... A61K 8/37
424/64
2010/0028277 A1* 2/2010 Chodorowski-Kimmes et al. ......
424/59
(Continued)

FOREIGN PATENT DOCUMENTS

EP 1 602 353 12/2005
EP 1 738 748 1/2007
(Continued)

OTHER PUBLICATIONS

U.S. Appl. No. 13/993,240, filed Jun. 11, 2013, Geffroy, et al.
International Search Report dated Mar. 6, 2013 in PCT/EP12/061308 Filed Jun. 14, 2012.

*Primary Examiner* — Jyothsna A Venkat
(74) *Attorney, Agent, or Firm* — Oblon, McClelland, Maier & Neustadt, L.L.P.

(57) ABSTRACT

The present invention relates to a cosmetic composition comprising, in a cosmetically acceptable medium, at least: (a) a supramolecular compound that may be obtained by reaction between: —at least one oil bearing at least one nucleophilic reactive function chosen from OH and $NH_2$, and —at least one junction group capable of establishing hydrogen bonds with one or more partner junction groups, each pairing of a junction group involving at least three hydrogen bonds, the said junction group bearing at least one isocyanate or imidazole reactive function capable of reacting with the reactive function borne by the oil, the said junction group also comprising at least one unit of formula (I) or (II): (b) at least two distinct non-volatile silicone oils chosen from: i) phenyl silicone oils, in particular of formula (II) or (VII) below: ii) linear or cyclic polydimethylsiloxanes (PDMSs), iii) polydimethylsiloxanes comprising alkyl or alkoxy groups, which are pendent and/or at the end of the silicone chain, these groups each containing from 2 to 24 carbon atoms, and (d) at least one agent for structuring the liquid fatty phase.

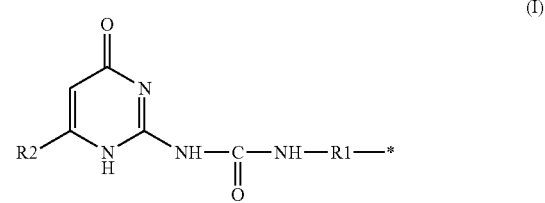

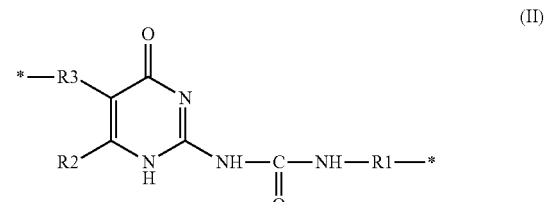

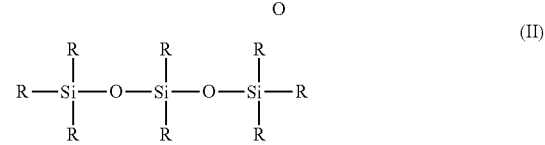

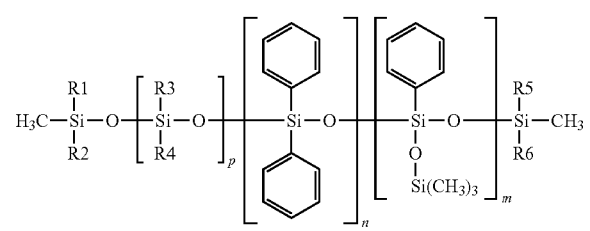

(Continued)

4 Claims, No Drawings

(56) References Cited

U.S. PATENT DOCUMENTS

| | | |
|---|---|---|
| 2010/0260700 A1 | 10/2010 | Dop |
| 2010/0260701 A1 | 10/2010 | Dop |
| 2010/0310489 A1 | 12/2010 | Barba |
| 2010/0310490 A1 | 12/2010 | Barba et al. |
| 2010/0316587 A1 | 12/2010 | Barba et al. |
| 2011/0002869 A1 | 1/2011 | Barba et al. |
| 2011/0038820 A1 | 2/2011 | Barba et al. |
| 2011/0177016 A1* | 7/2011 | Aliano ............... A61K 8/31 424/70.7 |
| 2013/0195778 A1* | 8/2013 | Chodorowski-Kimmes et al. ...... 424/59 |
| 2013/0267611 A1 | 10/2013 | Geffroy et al. |

FOREIGN PATENT DOCUMENTS

| | | |
|---|---|---|
| EP | 2 140 858 | 1/2010 |
| WO | 2009 080953 | 7/2009 |
| WO | 2011 147696 | 12/2011 |

* cited by examiner

COSMETIC COMPOSITION COMPRISING A SUPRAMOLECULAR COMPOUND CAPABLE OF ESTABLISHING HYDROGEN BONDS, AND TWO PARTICULAR DISTINCT SILICONE OILS

CROSS REFERENCE TO RELATED APPLICATIONS

The present application is a 35 U.S.C. § 371 national stage patent application of International patent application PCT/EP2012/061308, filed on Jun. 14, 2012, published as WO/2012/175402 on Dec. 27, 2012, the text of which is incorporated by reference, and claims the benefit of the filing date of French application no. 1155576, filed on Jun. 23, 2011, the text of which is also incorporated by reference.

The present invention relates to a cosmetic composition, especially for caring for and/or making up keratin materials, in particular the skin or the lips, especially the lips, comprising novel compounds A (referred to in the context of the present patent application as supramolecular compounds) capable of establishing hydrogen bonds with partner junction groups, combined with a wax and an oil, chosen from silicone oils.

According to one particular mode, the composition of the invention comprises at least novel supramolecular compounds combined with at least one agent for structuring the liquid fatty phase, in particular a wax and at least two particular distinct silicone oils.

Many cosmetic compositions exist for which gloss and/or remanence properties of the deposited film, after application to keratin materials, are desired. Examples that may be mentioned include lipsticks or nail varnishes. In order to obtain such a result, it is possible to combine particular starting materials, especially lanolins, with "glossy" oils such as polybutenes, or fatty acid or alcohol esters with a high carbon number; or alternatively certain plant oils; or alternatively esters resulting from the partial or total esterification of a hydroxylated aliphatic compound with an aromatic acid, as described in patent application EP 1 097 699.

However, these oils combined with compounds obtained by modification of oils containing an OH or NH2 function may give rise to a problem of tackiness. This tacky nature is unpleasant and causes these formulations to leave marks on supports, for instance glasses or coffee cups. Moreover, the presence of a film-forming agent for the remanence of the film on keratin materials may lead to compositions that cause drying-out.

Moreover, when it is sought to obtain solid compositions, it is important for the structuring of the composition to impart thereto sufficient strength to prevent it from breaking, for example during application to keratin materials, especially the skin or the lips, while at the same time being stable (no exudation or phase separation) over time (especially after 1 month at 23° C., and also at 45° C.). Moreover, the composition must also be easy to apply, especially in terms of glidance on application, and of cake erosion (amount deposited).

Formulators are thus in search of starting materials and/or systems for obtaining compositions whose deposit is fine and comfortable, with no drying-out effect, and which is characterized by gloss and a tack-free (or at least sparingly tack-free) effect. In the particular case of solid compositions, formulators are also in search of compositions that are easy to apply, that can be eroded easily and that are stable over time, whose deposit on the skin or the lips does not transfer and which shows good remanence and is characterized by a tack-free (or at least sparingly tack-free) effect.

The aim of the present invention is to propose cosmetic compositions, especially solid compositions, for obtaining such a uniform deposit on keratin materials, the said deposit having good remanence (especially remanence of the colour of the deposit and remanence of the gloss over time, in particular 1 hour after application), while at the same time being transfer-resistant or long-wearing and non-tacky (or sparingly tacky) and particularly comfortable to wear.

One subject of the present invention is thus a solid cosmetic composition, preferably for making up and/or caring for keratin materials (especially the skin or the lips, in particular the lips), comprising, in a cosmetically acceptable medium, at least:

(a) a compound A (referred to, in the context of the present patent application, as a supramolecular compound) that may be obtained by reaction between:
  at least one oil bearing at least one nucleophilic reactive function chosen from OH and $NH_2$, and
  at least one junction group capable of establishing hydrogen bonds with one or more partner junction groups, each pairing of a junction group involving at least three hydrogen bonds, the said junction group bearing at least one isocyanate or imidazole reactive function capable of reacting with the reactive function borne by the oil, the said junction group also comprising at least one unit of formula (I) or (II):

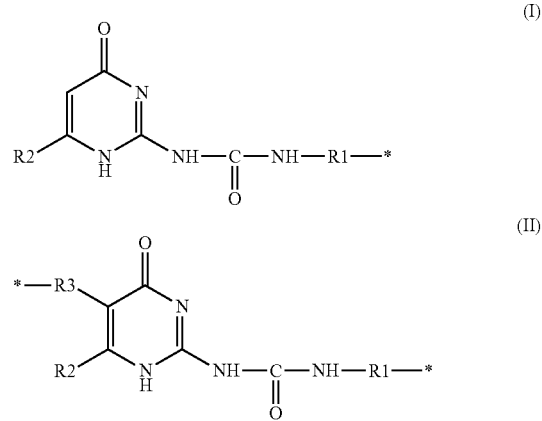

in which:
  R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;
  R2 represents a hydrogen atom or a linear, branched or cyclic, saturated or unsaturated, optionally aromatic, C1-C32 carbon-based and especially hydrocarbon-based radical, which may comprise one or more heteroatoms chosen from O, N, S, F, Si and P;
(b) at least one silicone oil;
(c) at least one wax.

According to one particular mode, one subject of the present invention is a cosmetic composition, preferably for making up and/or caring for keratin materials, especially the skin or the lips, in particular the lips, comprising, in a cosmetically acceptable medium, at least:

(a) a compound A (referred to, in the context of the present patent application, as a supramolecular compound) that may be obtained by reaction between:

at least one oil bearing at least one nucleophilic reactive function chosen from OH and $NH_2$, and at least one junction group capable of establishing hydrogen bonds with one or more partner junction groups, each pairing of a junction group involving at least three hydrogen bonds, the said junction group bearing at least one isocyanate or imidazole reactive function capable of reacting with the reactive function borne by the oil, the said junction group also comprising at least one unit of formula (I) or (II):

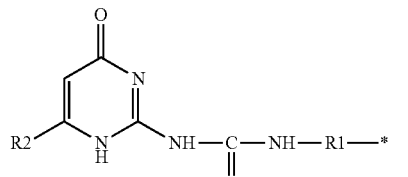

(I)

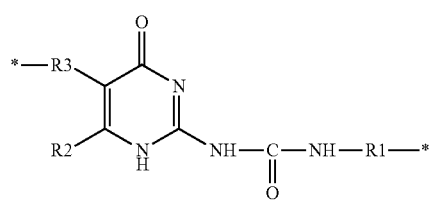

(II)

in which:

R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;

R2 represents a hydrogen atom or a linear, branched or cyclic, saturated or unsaturated, optionally aromatic, C1-C32 carbon-based and especially hydrocarbon-based radical, which may comprise one or more heteroatoms chosen from O, N, S, F, Si and P;

(b) at least two distinct non-volatile silicone oils chosen from:

i) phenyl silicone oils, in particular of formula (II) or (VII) below:

(II)

in which the groups R represent, independently of each other, saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl, or a phenyl, at least one of the groups R being a phenyl group,

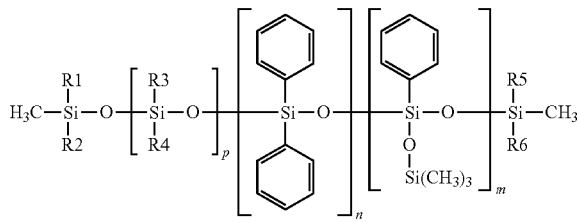

(VII)

in which:

R1 to R6, independently of each other, are saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl, m, n and p are, independently of each other, integers between 0 and 100, with the proviso that the sum n+m is between 1 and 100;

(X)

ii) linear or cyclic polydimethylsiloxanes (PDMSs), iii) polydimethylsiloxanes comprising alkyl or alkoxy groups, which are pendent and/or at the end of the silicone chain, these groups each containing from 2 to 24 carbon atoms, it being understood that:

at least one of the non-volatile silicone oils is chosen from the phenyl silicone oils of formula (II) or of formula (VII) with p=0 (also known as oil that is "compatible" with the supramolecular compound in the description) and at least one of the said non-volatile silicone oils is chosen from the phenyl silicone oils of formula (VII) with p≠0 and $R_3$ and $R_4$ are saturated or unsaturated, linear or branched $C_1$-$C_{30}$ and especially $C_1$-$C_{12}$ hydrocarbon-based radicals, and in particular a methyl, ethyl, propyl or butyl radical, preferably methyl, linear or cyclic polydimethylsiloxanes (PDMSs), and polydimethylsiloxanes comprising alkyl or alkoxy groups, which are pendent and/or at the end of the silicone chain, these groups each containing from 2 to 24 carbon atoms (also known as oil that is "incompatible" with the supramolecular compound in the description), and (d) advantageously at least one agent for structuring the liquid fatty phase, chosen especially from waxes and/or pasty fatty substances, in particular waxes, preferably apolar waxes.

According to another particular mode, a subject of the present invention is a cosmetic composition, preferably for making up and/or caring for keratin materials, especially the skin or the lips, in particular the lips, comprising, in a cosmetically acceptable medium, at least:

(a) a compound A (referred to, in the context of the present patent application, as a supramolecular compound) that may be obtained by reaction between:

at least one oil bearing at least one nucleophilic reactive function chosen from OH and $NH_2$, and at least one junction group capable of establishing hydrogen bonds with one or more partner junction groups, each pairing of a junction group involving at least three hydrogen bonds, the said junction group bearing at least one isocyanate or imidazole reactive function capable of reacting with the reactive function borne by the oil, the said junction group also comprising at least one unit of formula (I) or (II):

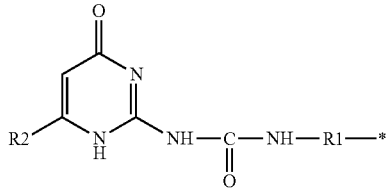

(I)

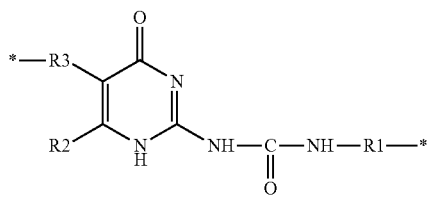

(II)

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;
R2 represents a hydrogen atom or a linear, branched or cyclic, saturated or unsaturated, optionally aromatic, C1-C32 carbon-based and especially hydrocarbon-based radical, which may comprise one or more heteroatoms chosen from O, N, S, F, Si and P;

(b) at least two distinct non-volatile silicone oils of formula (X), (II) or (VII) below:

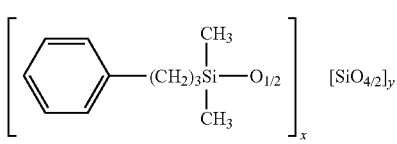

(X)

in which x/y is equal to 2 with y ranging from 1 to 30,

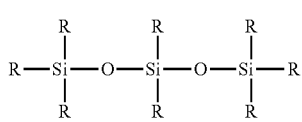

(II)

in which the groups R represent, independently of each other, saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl, or a phenyl, at least one of the groups R being a phenyl group,

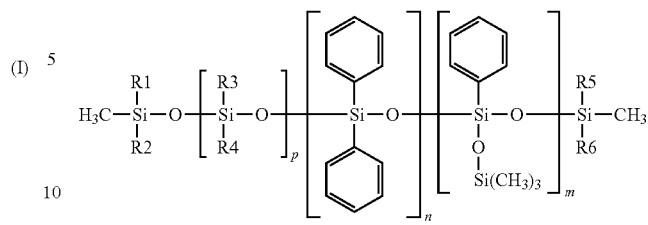

(VII)

in which:
R1 to R6, independently of each other, are saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl,
m, n and p are, independently of each other, integers between 0 and 100, with the proviso that the sum n+m is between 1 and 100;

ii) linear or cyclic polydimethylsiloxanes (PDMSs),
iii) polydimethylsiloxanes comprising alkyl or alkoxy groups, which are pendent and/or at the end of the silicone chain, these groups each containing from 2 to 24 carbon atoms, it being understood that:
at least one of the non-volatile silicone oils is chosen from the phenyl silicone oils of formula (X) and
at least one of the said non-volatile silicone oils is chosen from the phenyl silicone oils of formula (VII) with p≠0 and $R_3$ and $R_4$ are saturated or unsaturated, linear or branched $C_1$-$C_{30}$ and especially $C_1$-$C_{12}$ hydrocarbon-based radicals, and in particular a methyl, ethyl, propyl or butyl radical, preferably methyl, linear or cyclic polydimethylsiloxanes (PDMSs), and polydimethylsiloxanes comprising alkyl or alkoxy groups, which are pendent and/or at the end of the silicone chain, these groups each containing from 2 to 24 carbon atoms (also known as oil that is "incompatible" with the supramolecular compound in the description), and
(d) advantageously at least one agent for structuring the liquid fatty phase, chosen especially from waxes and/or pasty fatty substances, in particular waxes, preferably apolar waxes.

According to another particular mode, a subject of the present invention is a cosmetic composition, preferably for making up and/or caring for keratin materials, especially the skin or the lips, in particular the lips, comprising, in a cosmetically acceptable medium, at least:
(a) a compound A (referred to, in the context of the present patent application, as a supramolecular compound) that may be obtained by reaction between:
at least one oil bearing at least one nucleophilic reactive function chosen from OH and $NH_2$, and
at least one junction group capable of establishing hydrogen bonds with one or more partner junction groups, each pairing of a junction group involving at least three hydrogen bonds, the said junction group bearing at least one isocyanate or imidazole reactive function capable of reacting with the reactive function borne by the oil, the said junction group also comprising at least one unit of formula (I) or (II):

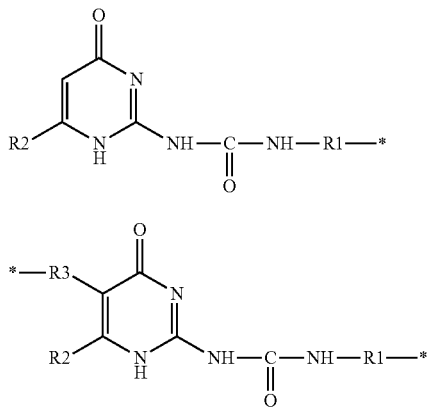

(I)

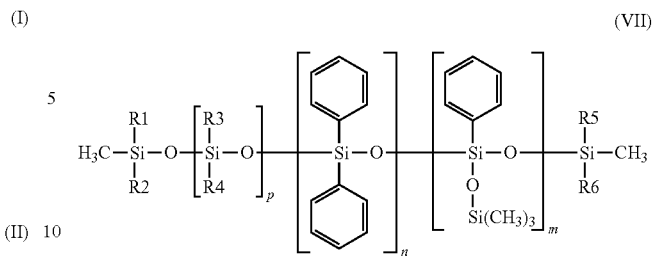

(VII)

in which:
R1 to R6, independently of each other, are saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl, m, n and p are, independently of each other, integers between 0 and 100, with the proviso that the sum n+m is between 1 and 100;

ii) linear or cyclic polydimethylsiloxanes (PDMSs), iii) polydimethylsiloxanes comprising alkyl or alkoxy groups, which are pendent and/or at the end of the silicone chain, these groups each containing from 2 to 24 carbon atoms, it being understood that:
at least one of the non-volatile silicone oils is chosen from the phenyl silicone oils of formula (III) and
at least one of the said non-volatile silicone oils is chosen from the phenyl silicone oils of formula (II), (VII) or (X), and (d) advantageously at least one agent for structuring the liquid fatty phase, chosen especially from waxes and/or pasty fatty substances, in particular waxes, preferably apolar waxes.

In particular, the total content of agents for structuring the liquid fatty phase is less than or equal to 20% by weight and preferably less than or equal to 15% by weight relative to the total weight of the said composition.

Preferably, the composition of the invention according to the various embodiments described above comprises at least one agent for structuring the liquid fatty phase, chosen especially from waxes and/or pasty fatty substances, in particular waxes, in a content ranging from 1% to 20% by weight, in particular from 1% to 15% by weight and better still from 1% to 10% by weight relative to the total weight of the said composition.

In particular, the composition of the invention is in solid form, especially in the form of a cast product or a stick.

The invention also relates to a cosmetic process for making up keratin materials, especially the skin and/or the lips, in particular the lips, comprising the application to the said keratin materials, especially the skin and/or the lips, in particular the lips, of a composition according to the invention.

Supramolecular Compounds:

The compounds A (also known as supramolecular compounds) functionalized according to the present invention are in the form of a solid; this makes it possible especially to form a non-tacky material, which does not transfer onto the fingers once applied to keratin materials; this is not the case for the functionalized compounds of the prior art, especially as described in U.S. Pat. No. 5,707,612, which are (II)

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;

R2 represents a hydrogen atom or a linear, branched or cyclic, saturated or unsaturated, optionally aromatic, C1-C32 carbon-based and especially hydrocarbon-based radical, which may comprise one or more heteroatoms chosen from O, N, S, F, Si and P;

(b) at least two distinct non-volatile silicone oils of formula (III), (X), (II) or (VII) below:

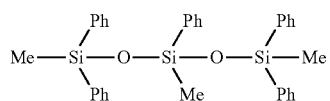

(III)

in which Me represents methyl, Ph represents phenyl,

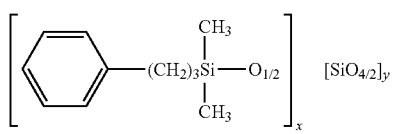

(X)

in which x/y is equal to 2 with y ranging from 1 to 30,

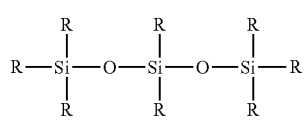

(II)

in which the groups R represent, independently of each other, saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl, or a phenyl, at least one of the groups R being a phenyl group, in the form of a more or less viscous liquid, and which form a tacky material that transfers onto the fingers after application to keratin materials.

Moreover, it has been found that crosslinking by means of four hydrogen bonds, via ureidopyrimidone groups, can increase the strength of this crosslinking, and thus improve the remanence of the desired cosmetic effect, most particularly the remanence of the deposit or of the gloss.

Furthermore, the compounds, or functionalized oils, according to the invention are easy to convey in the usual cosmetic media, especially the usual cosmetic oily media.

They are advantageously compatible with the oils usually present in cosmetic compositions, and also have good properties of dispersing pigments or fillers.

They are easy to convey in cosmetic oily or solvent media, especially oils, fatty alcohols and/or fatty esters, which facilitates their use in the cosmetic field, especially in lipsticks.

They show acceptable solubility in varied cosmetic oily media, such as plant oils, alkanes, esters, whether they are short esters such as butyl or ethyl acetate, or fatty esters, and fatty alcohols, and most particularly in media comprising isododecane, Parleam, isononyl isononanoate, octyldodecanol and/or a C12-C15 alkyl benzoate.

The cosmetic compositions according to the invention moreover show good applicability and good coverage; good adherence to the support, whether it is to the nails, the eyelashes, the skin or the lips; adequate flexibility and strength of the film, and also an excellent gloss durability. The comfort and glidance properties are also very satisfactory.

In general, in the context of the present patent application, the compounds A may be referred to without preference as "supramolecular compounds" for convenience and for greater clarity.

The compounds A (or supramolecular compounds) of the compositions according to the invention may be obtained by reaction between:
- at least one oil bearing at least one nucleophilic reactive function chosen from OH and $NH_2$, and
- at least one junction group capable of establishing hydrogen bonds with one or more partner junction groups, each pairing of a junction group involving at least three hydrogen bonds, the said junction group bearing at least one isocyanate or imidazole reactive function capable of reacting with the reactive function borne by the oil, the said junction group also comprising at least one unit of formula (I) or (II):

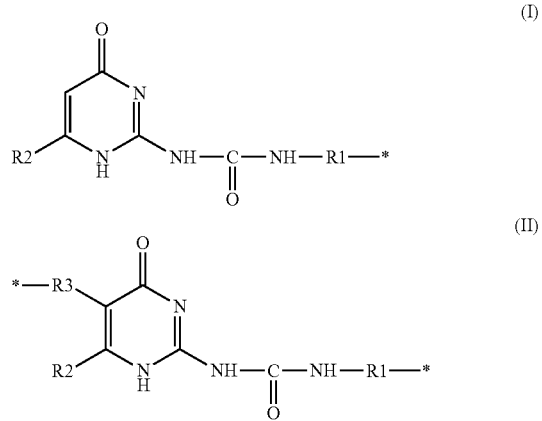

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;
R2 represents a hydrogen atom or a linear, branched or cyclic, saturated or unsaturated, optionally aromatic, C1-C32 carbon-based and especially hydrocarbon-based radical, which may comprise one or more heteroatoms chosen from O, N, S, F, Si and P.

In conclusion, the supramolecular compounds of the compositions according to the invention thus comprise at least one part (HB) originating from the oil and at least one part (G) originating from the junction group, the said part (G) comprising at least one unit of formula (I) or (II).

In particular, the said parts (HB) and (G) are connected via a covalent bond and may especially be connected via a covalent bond formed during the reaction between the OH and/or $NH_2$ reactive functions borne by the oil and the isocyanate reactive functions borne by the junction group; or alternatively between the $NH_2$ reactive functions borne by the oil and the isocyanate or imidazole functions borne by the junction group.

The preferential production of the compounds according to the invention may thus especially be represented schematically by the chemical reaction between the following species:

or

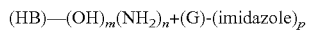

with m, n and p being non-zero integers.

The oil that may be used to prepare the compound according to the invention, which may preferably be represented schematically as $(HB)-(OH)_m(NH_2)_n$, is a fatty substance or a mixture of fatty substances, which is not crystalline at 25° C., and is liquid at room temperature and at atmospheric pressure (25° C., 1 atm.); preferably apolar or even, preferably, water-insoluble.

Preferably, the oil that may be used to prepare the supramolecular compound according to the invention is non-polymeric.

The term "liquid" means that the viscosity of the compound is less than or equal to 2500 centipoises, at 110° C. and 1 atm., measured with a Brookfield DV-I or Brookfield Cap 1000+ rheometer, a person skilled in the art selecting the machine that is suited to the viscosity measurement.

The term "apolar" means a compound whose HLB value (hydrophilic/lipophilic balance) is low; especially less than or equal to 8, preferably less than or equal to 4 and better still less than or equal to 2; preferentially, the HLB value should be low enough to make it possible to obtain a supramolecular material that is not hygroscopic, or not too hygroscopic.

The term "insoluble" means that the oil fraction that can dissolve in water, at 25° C. and 1 atm., is less than 5% by weight (i.e. 5 g of oil in 100 ml of water); preferably less than 3%. The term "fatty substance" means especially, but not exclusively, a hydrocarbon-based compound comprising one or more saturated or unsaturated, linear, cyclic or branched alkyl chains, containing at least 6 carbon atoms and possibly comprising polar groups such as an acid, hydroxyl or polyol, amine, amide, phosphoric acid, phosphate, ester, ether, urea, carbamate, thiol, thioether or thioester group, this chain possibly containing up to 100 carbon atoms.

Preferably, the oil that may be used to prepare the compound according to the invention is a glossy oil, i.e. an oil with a refractive index of greater than or equal to 1.46 at 25° C. and in particular between 1.46 and 1.55 (the refractive index being defined relative to the sodium D line, at 25° C.).

Preferably, the oil that may be used to prepare the supramolecular compound according to the invention is a non-volatile oil. The term "non-volatile oil" means an oil that is capable of remaining on keratin materials at room temperature and atmospheric pressure for at least several hours, and that especially has a vapour pressure of less than $10^{-3}$ mmHg (0.13 Pa).

Preferably, the oil has a molar mass (Mw) of between 150 and 6000, especially between 170 and 4000, or even between 180 and 2000, more preferentially between 200 and 1500 and better still between 220 and 800 g/mol.

The oil that may be used in the context of the present invention bears at least one reactive function capable of reacting with the reactive function borne on the junction group, and is especially capable of reacting chemically with the isocyanate or imidazole groups borne by the junction group; preferably, this function is an OH or $NH_2$ function. Preferably, the oil comprises only OH functions, in particular 1 to 3 OH functions, preferentially primary or secondary OH functions, and better still only primary functions.

The oil according to the present invention is preferably a carbon-based and especially a hydrocarbon-based oil, which, besides the reactive function capable of reacting with the junction group, may comprise oxygen, nitrogen, sulfur and/or phosphorus atoms. The oil is very preferentially chosen from cosmetically acceptable oils.

The oil that may be used in the context of the present invention may be chosen from:
(i) linear, branched or cyclic, saturated or unsaturated fatty alcohols, comprising 6 to 50 carbon atoms, and comprising one or more OH; optionally comprising one or more $NH_2$. Mention may be made in particular of:
- saturated or unsaturated, linear or branched C6-C50, especially C6-C32 and in particular C8-C28 monoalcohols, and especially isostearyl alcohol, cetyl alcohol, oleyl alcohol, isopalmitoyl alcohol, 2-butyloctanol, 2-hexyldecanol, 2-octyldecanol, 2-octyldodecanol, 2-octyltetradecanol, 2-decyltetradecanol and 2-dodecylhexadecanol, and especially the alcohols sold under the name Jarcol by the company Jarchem Industries, such as Jarcol I-12, Jarcol I-16, Jarcol I-20 and Jarcol I-24;
- saturated or unsaturated, linear or branched, C6-C50, especially C6-C40 and in particular C8-C38 diols, and especially branched C32-36 diols, and in particular the commercial product Pripol 2033 from Uniqema;
- saturated or unsaturated, linear or branched C6-C50, especially C6-C32 and in particular C8-C28 triols, and especially phytanetriol;

(ii) esters and ethers bearing at least one free OH, and especially partial polyol esters and ethers, and hydroxylated carboxylic acid esters.

The term "partial polyol ester" means esters prepared by esterification of a polyol with a substituted or unsubstituted carboxylic acid, the reaction not being total, i.e. not performed on all of the free OHs of the polyol; as a result, the ester thus still comprises at least one free OH.

Preferably, the carboxylic acid is a monoacid. A mixture of carboxylic acids, especially monocarboxylic acids, may also be used.

The term "partial polyol ether" means ethers prepared by etherification of a polyol, with itself or with at least one other monohydroxylated or polyhydroxylated alcohol, preferably a monoalcohol, the etherification reaction not being total, i.e. not performed on all of the free OHs of the polyol; as a result, the ether still comprises at least one free OH.

The term "hydroxylated carboxylic acid ester" means (mono and poly)esters prepared by reaction between a carboxylic acid bearing at least one free OH function, and one or more (mono or poly)alcohols, preferably a monoalcohol, the reaction possibly being total or partial (performed on all or some of the free OHs of the alcohol).

Among the polyols that may be used for preparing the above esters or ethers, mention may be made of propylene glycol, glycerol, neopentyl glycol, trimethylolpropane, trimethylolethane, polyglycerols and especially polyglycerol-2, polyglycerol-3 and polyglycerol-10; erythritol, dipentaerythritol, pentaerythritol, bis(trimethylolpropane), phytanetriol, sucrose, glucose, methylglucose, sorbitol, fructose, xylose, mannitol or glucosamine; and also diol dimers obtained especially from fatty acid dimers, especially branched aliphatic and/or alicyclic C32-C38 and especially C36 diols, such as those defined in the article Hofer et al., European Coating Journal (March 2000), pages 26-37; and mixtures thereof.

Among the monoalcohols that may be used for preparing the above esters or ethers, mention may be made of linear or branched, preferably branched, C3-C50 alcohols, and especially 2-ethylhexanol, octanol and isostearyl alcohol, and mixtures thereof.

Among the carboxylic acids that may be used for preparing the above esters or ethers, mention may be made of linear or branched, saturated or unsaturated monoacids containing 6 to 50 carbon atoms and diacids containing 3 to 12 carbon atoms, among which mention may be made of octylneodecanoic acid, hexyldecanoic acid, ethylhexanoic acid, isostearic acid, nonanoic acid, isononanoic acid, arachidic acid, stearic acid, palmitic acid, oleic acid, oxalic acid, adipic acid, succinic acid, fumaric acid, maleic acid, capric acid, hexanedioic acid and decanoic acid, and mixtures thereof.

Among the hydroxylated carboxylic acids that may be used for preparing the above esters or ethers, mention may be made of monohydroxylated or polyhydroxylated acids, preferably monohydroxylated acids, containing for example 4 to 28 carbon atoms, and especially 12-hydroxystearic acid, ricinoleic acid, malic acid, lactic acid and citric acid; and mixtures thereof.

Thus, the oil that may be used to prepare the supramolecular compound in the present invention may be chosen, alone or as a mixture, from:
- pentaerythritol partial esters, and especially pentaerythrityl adipate, pentaerythrityl caprate, pentaerythrityl succinate, pentaerythrityl tetraisononanoate, pentaerythrityl triisononanoate, pentaerythrityl tetraisostearate, pentaerythrityl triisostearate, pentaerythrityl tetrakis(2-decyl)tetradecanoate, pentaerythrityl tetrakis(ethyl)hexanoate and pentaerythrityl tetrakis(octyl)dodecanoate;
- dipentaerythritol diesters, triesters, tetraesters or pentaesters, and especially dipentaerythrityl pentaisononanoate, dipentaerythrityl pentaisostearate, dipentaerythrityl tetraisostearate and dipentaerythrityl tris(polyhydroxystearate);

trimethylolpropane monoesters and diesters, for instance trimethylolpropane monoisostearate, trimethylolpropane diisostearate, trimethylolpropane mono-2-ethylhexanoate and trimethylolpropane bis(2-ethylhexanoate);

bis(trimethylolpropane)monoesters, diesters and triesters, for instance bis(trimethylolpropane)diisostearate, bis(trimethylolpropane)triisostearate and bis(trimethylolpropane)triethylhexanoate;

partial monoesters or polyesters of glycerol or of polyglycerols, and especially:

glyceryl diisostearate and glyceryl diisononanoate;

polyglycerol-2 monoesters, diesters and triesters; for example with isostearic acid, 2-ethylhexanoic acid and/or isononanoic acid; and especially polyglyceryl-2 isostearate; polyglyceryl-2 diisostearate; polyglyceryl-2 triisostearate; polyglyceryl-2 nonaisostearate; polyglyceryl-2 nonanoate;

polyglycerol-3 monoesters, diesters, triesters or tetraesters; for example with either isostearic acid, 2-ethylhexanoic acid and/or isononanoic acid; and especially polyglyceryl-3 isostearate; polyglyceryl-3 diisostearate; polyglyceryl-3 triisostearate; polyglyceryl-3 nonaisostearate; polyglyceryl-3 nonanoate;

polyglycerol-10 partial esters and in particular polyglyceryl-10 nonaisostearate; polyglyceryl-10 nonanoate; polyglyceryl-10 isostearate; polyglyceryl-10 diisostearate; polyglyceryl-10 triisostearate;

propylene glycol monoesters, for instance propylene glycol monoisostearate, propylene glycol neopentanoate or propylene glycol monooctanoate;

diol dimer monoesters, for instance isostearyl dimer dilinoleate and octyldodecyl dimer dilinoleate;

glycerol ethers, such as polyglyceryl-2 oleyl ether, polyglyceryl-3 cetyl ether, polyglyceryl-3 decyl tetradecyl ether and polyglyceryl-2 stearyl ether;

esters between a hydroxylated monocarboxylic, dicarboxylic or tricarboxylic acid and monoalcohols, and in particular:

esters, especially monoesters, of 12-hydroxystearic acid; such as octyl hydroxystearate and 2-octyldodecyl hydroxystearate; mention may also be made of the corresponding oligomeric polyhydroxystearates, especially with a degree of polymerization of from 1 to 10, containing at least one residual OH;

lactic acid esters, especially C4-40 alkyl lactates, such as 2-ethylhexyl lactate, diisostearyl lactate, isostearyl lactate, isononyl lactate and 2-octyldodecyl lactate;

malic acid esters, and especially C4-40 alkyl malates, such as bis(2-ethyl)hexyl malate, diisostearyl malate and bis(2-octyl)dodecyl malate;

citric acid esters, and especially C4-40 alkyl citrates, such as triisostearyl citrate, triisocetyl citrate and triisoarachidyl citrate;

(iii) hydroxylated natural oils, modified natural oils and plant oils, and especially:

triglyceryl esters bearing one or more OHs;

hydrogenated or non-hydrogenated castor oil, and also derivatives thereof derived especially from the transesterification of castor oil; for instance the products Polycin M-365 or Polycin 2525 sold by Vertellus;

modified epoxidized oils, the modification consisting in opening the epoxy function to obtain a diol, and especially hydroxylated modified soybean oil; hydroxylated soybean oils (directly hydroxylated or epoxidized beforehand); and especially the oils Agrol 2.0, Agrol 3.0 and Agrol 7.0 sold by Bio-Based Technologies, LLC; the oil Soyol R2-052 from the company Urethane Soy System; the Renuva oils sold by Dow Chemical; the oils BioH Polyol 210 and 500 sold by Cargill.

According to a first particularly preferred embodiment, the oil that may be used to prepare the supramolecular compound in the context of the present invention is chosen from linear, branched or cyclic, saturated or unsaturated fatty alcohols, comprising 6 to 50 carbon atoms, comprising one or more OH; optionally comprising one or more $NH_2$, such as:

saturated or unsaturated, linear or branched C6-C50, especially C6-C32 and in particular C8-C28 monalcohols, and especially isostearyl alcohol, cetyl alcohol, oleyl alcohol, isopalmitoyl alcohol, 2-butyloctanol, 2-hexyldecanol, 2-octyldecanol, 2-octyldodecanol, 2-octyltetradecanol, 2-decyltetradecanol and 2-dodecylhexadecanol, and especially the alcohols sold under the name Jarcol by the company Jarchem Industries, such as Jarcol I-12, Jarcol I-16, Jarcol I-20 and Jarcol I-24;

saturated or unsaturated, linear or branched, C6-C50, especially C6-C40 and in particular C8-C38 diols, and especially branched C32-36 diols, and in particular the commercial product Pripol 2033 from Uniqema;

saturated or unsaturated, linear or branched C6-C50, especially C6-C32 and in particular C8-C28 triols, and especially phytanetriol.

According to this first preferred embodiment, the oil that may be used to prepare the supramolecular compound in the context of the present invention is preferably chosen from linear or branched, saturated or unsaturated C6-C50, especially C6-C32 and in particular C8-C28 monalcohols, and especially isostearyl alcohol, cetyl alcohol, oleyl alcohol, isopalmitoyl alcohol, 2-butyloctanol, 2-hexyldecanol, 2-octyldodecanol, 2-octyldodecanol, 2-octyltetradecanol, 2-decyltetra-decanol and 2-dodecylhexadecanol, and especially the alcohols sold under the name Jarcol by the company Jarchem Industries, such as Jarcol I-12, Jarcol I-16, Jarcol I-20 and Jarcol I-24.

According to one preferred mode, use will be made of the alcohols sold under the name Jarcol I-24.

According to a second particularly preferred embodiment, the oil that may be used to prepare the supramolecular compound in the context of the present invention is chosen from esters between a hydroxylated mono-, di- or tricarboxylic acid and monoalcohols, and in particular:

esters, especially monoesters, of 12-hydroxystearic acid; such as octyl hydroxystearate and 2-octyldodecyl hydroxystearate; mention may also be made of the corresponding oligomeric polyhydroxystearates, especially with a degree of polymerization of from 1 to 10, containing at least one residual OH;

lactic acid esters, especially C4-40 alkyl lactates, such as 2-ethylhexyl lactate, diisostearyl lactate, isostearyl lactate, isononyl lactate and 2-octyldodecyl lactate;

malic acid esters, and especially C4-40 alkyl malates, such as bis(2-ethyl)hexyl malate, diisostearyl malate and bis(2-octyl)dodecyl malate;

citric acid esters, and especially C4-40 alkyl citrates, such as triisostearyl citrate, triisocetyl citrate and triisoarachidyl citrate.

According to this second preferred embodiment, the oil that may be used in the context of the present invention is preferably chosen from esters between a hydroxylated dicarboxylic acid and monoalcohols, and in particular of malic acid, and especially C4-40 alkyl malates, such as bis(2-ethyl)hexyl malate, diisostearyl malate and bis(2-octyl)dodecyl malate.

In particular, when glossy oils are used, use may be made of the following glossy oils, for which the refractive index at 25° C. is indicated in parentheses: polyglyceryl-3 diisostearate (1.472), phytanetriol (1.467), castor oil (1.475), 2-octyldodecanol (1.46), oleyl alcohol (1.461), octyl hydroxystearate (1.46), polyglyceryl-2 isostearate (1.468), polyglyceryl-2 diisostearate (1.464), diisostearyl malate (1.462), 2-butyloctanol, 2-hexyldecanol (1.45), 2-decyltetradecanol (1.457), and also mixtures thereof.

Preferably, the oils that may be used in the present invention are chosen from 2-octyldodecanol, diisostearyl malate, 2-butyloctanol, 2-hexyldecanol, 2-decyltetradecanol; hydrogenated or non-hydrogenated castor oil, and also derivatives thereof; hydroxylated modified soybean oil, and mixtures thereof.

Junction Group

The junction group that may be used to form the supramolecular compound of the compositions according to the invention bears at least one reactive group, especially isocyanate or imidazole, capable of reacting with the reactive functions, especially OH and/or $NH_2$ (exclusively $NH_2$ for imidazole), of the oil, so as to form a covalent bond, especially of urethane type, between the said oil and the said junction group.

Preferably, the junction group that may be used to form the supramolecular compound of the compositions according to the invention bears at least one reactive group, especially isocyanate.

The said junction group is capable of establishing H bonds with one or more partner junction groups, of identical or different chemical nature, each junction group pairing involving at least 3H (hydrogen) bonds, preferably at least 4H bonds and preferentially 4H bonds.

For the purposes of the invention, the term "junction group" means any functional group comprising groups that are H bond donors or acceptors, and that are capable of establishing at least 3H bonds, preferably at least 4H bonds, preferentially 4H bonds, with an identical or different partner junction group.

For the purposes of the invention, the term "partner junction group" means any junction group that can establish H bonds with one or more junction groups of the same or of another polymer according to the invention. The junction groups may be of identical or different chemical nature. If they are identical, they may then establish H bonds between themselves and are then referred to as self-complementary junction groups. If they are different, they are chosen such that they are complementary with respect to H interactions.

The said junction group, bearing isocyanate groups, may thus be represented schematically as $(G)-(NCO)_p$, p being a non-zero integer, preferably equal to 1 or 2.

The junction group moreover comprises at least one monovalent unit of formula (I) and/or at least one divalent unit of formula (II), as defined below:

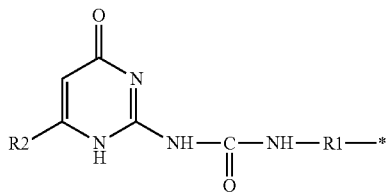

(I)

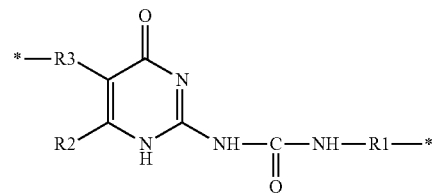

(II)

in which:

R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;

R2 represents a hydrogen atom or a linear, branched or cyclic, saturated or unsaturated, optionally aromatic, C1-C32 carbon-based and especially hydrocarbon-based (alkyl) radical, which may comprise one or more heteroatoms chosen from O, N, S, F, Si and P.

Preferably, the junction group moreover comprises at least one monovalent unit of formula (I).

The radical R1 may especially be:

a linear or branched, divalent C2-C12 alkylene group, especially a 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene) or 1,7-(3,7-dimethyloctylene) group;

a divalent C4-C12 cycloalkylene or arylene group, chosen especially from the following radicals: isophorone-, tolylene, 2-methyl-1,3-phenylene, 4-methyl-1,3-phenylene; 4,4'-methylenebiscyclohexylene; 4,4-bisphenylenemethylene; or of structure:

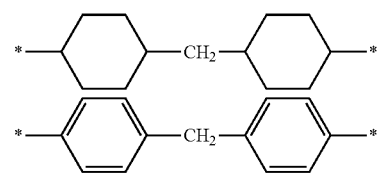

The term "-isophorone-" means the divalent radical having the structure:

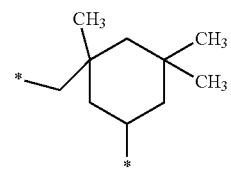 [SMILES: *CC1(C)CC(*)CC(C)(C)C1]

Preferentially, R1 represents -isophorone-, —$(CH_2)_6$— or 4,4'-methylenebiscyclohexylene.

The radical R2 may especially be H or:

a $C_1$-$C_{32}$, in particular $C_1$-$C_{16}$ or even $C_1$-$C_{10}$ alkyl group;
a $C_4$-$C_{12}$ cycloalkyl group;
a $C_4$-$C_{12}$ aryl group;
a $(C_4$-$C_{12})aryl(C_1$-$C_{18})$alkyl group;

a $C_1$-$C_4$ alkoxy group;

an arylalkoxy group, in particular an aryl($C_1$-$C_4$)alkoxy group;

a $C_4$-$C_{12}$ heterocycle;

or a combination of these radicals, which may be optionally substituted with an amino, ester and/or hydroxyl function.

Preferably, R2 represents H, $CH_3$, ethyl, $C_{13}H_{27}$, $C_7H_{15}$, phenyl, isopropyl, isobutyl, n-butyl, tert-butyl, n-propyl or —CH($C_2H_5$)($C_4H_9$).

Preferably, R3 represents a divalent radical —R'3-O—C(O)—NH—R'4— in which R'3 and R'4, which may be identical or different, represent a divalent carbon-based radical chosen from a linear or branched $C_1$-$C_{32}$ alkyl group, a $C_4$-$C_{16}$ cycloalkyl group and a $C_4$-$C_{16}$ aryl group; or a mixture thereof.

In particular, R'3 and R'4 may represent methylene, 1,2-ethylene, 1,6-hexylene, 1,4-butylene, 1,6-(2,4,4-trimethylhexylene), 1,4-(4-methylpentylene), 1,5-(5-methylhexylene); 1,6-(6-methylheptylene); 1,5-(2,2,5-trimethylhexylene), 1,7-(3,7-dimethyloctylene); 4,4'-methylenebiscyclohexylene; 2-methyl-1,3-phenylene; 4-methyl-1,3-phenylene; 4,4'-bisphenylenemethylene; 1,2-tolylene, 1,4-tolylene, 2,4-tolylene, 2,6-tolylene; 1,5-naphthylene; tetramethylxylylene; isophorone.

Most particularly, R'3 may represent a C1-C4 alkylene, especially 1,2-ethylene.

Preferably, R'4 may represent the divalent radical derived from isophorone.

Most particularly, R3 may have the structure:

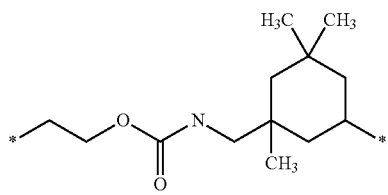 [SMILES: *CCOC(=O)NCC1(C)CC(*)CC(C)(C)C1]

In a particularly preferred manner, the following may apply in formula (I):

$R_1$=-isophorone-, R2=methyl, which gives the unit of formula:

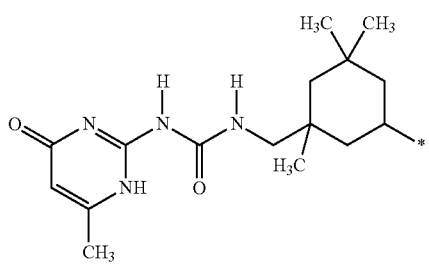

$R_1$=—($CH_2$)$_6$—, R2=methyl, which gives the unit of formula:

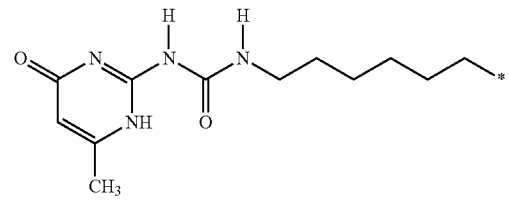

$R_1$=—($CH_2$)$_6$—, R2=isopropyl, which gives the unit of formula:

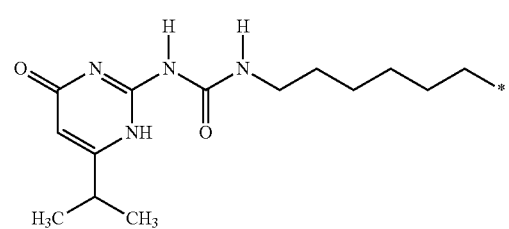

$R_1$=4,4'-methylenebiscyclohexylene and R2=methyl, which gives the unit of formula:

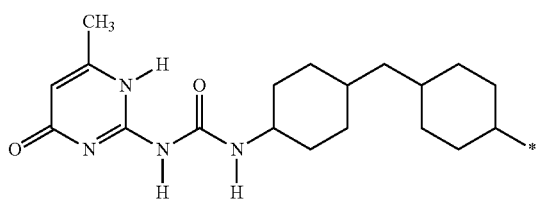

In a particularly preferred manner, in formula (II), R1 represents the -isophorone- radical, R2=methyl and R3=—($CH_2$)$_2$OCO—NH-isophorone-, which gives the divalent unit of formula:

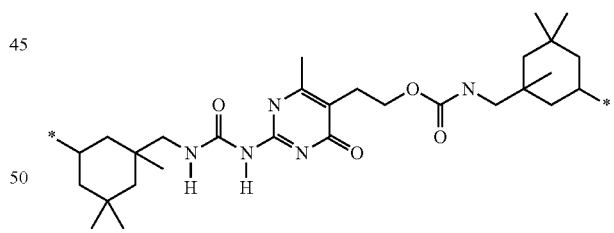

The junction groups bearing only one isocyanate function may have the formula:

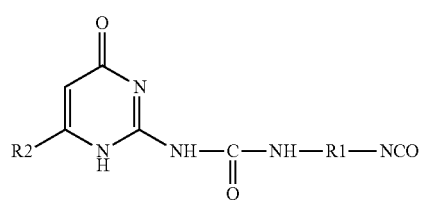

in which R1 and R2 are as defined above; and in particular:
R1 represents -isophorone-, —(CH$_2$)$_6$—, —CH$_2$CH(CH$_3$)—CH$_2$—C(CH$_3$)$_2$—CH$_2$—CH$_2$, 4,4'-methylenebiscyclohexylene or 2-methyl-1,3-phenylene; and/or
R2 represents H, CH$_3$, ethyl, C$_{13}$H$_{27}$, C$_7$H$_{15}$, phenyl, isopropyl, isobutyl, n-butyl, tert-butyl, n-propyl or —CH(C$_2$H$_5$)(C$_4$H$_9$).

Preferably, the junction groups may be chosen from the following groups:

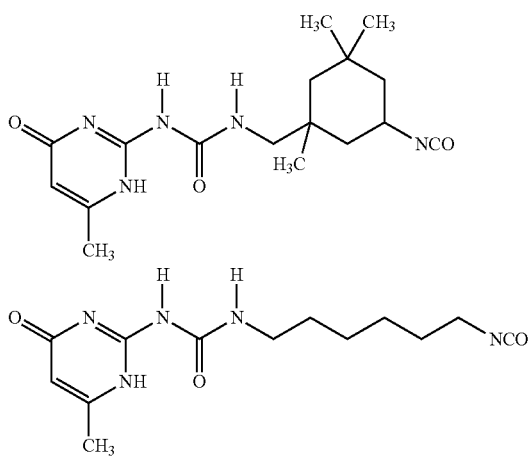

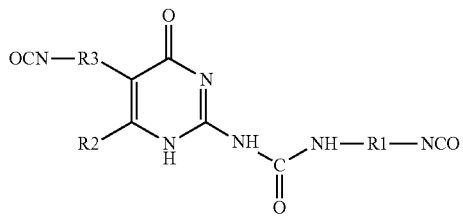

in which R1, R2 and R3 are as defined above, and in particular:
R1 represents -isophorone-, —(CH$_2$)$_2$—, —(CH$_2$)$_6$—, —CH$_2$CH(CH$_3$)—CH$_2$—C(CH$_3$)$_2$—CH$_2$—CH$_2$, 4,4'-methylenebiscyclohexylene or 2-methyl-1,3-phenylene; and/or
R2 represents H, CH$_3$, ethyl, C$_{13}$H$_{27}$, C$_7$H$_{15}$, phenyl, isopropyl, isobutyl, n-butyl, tert-butyl, n-propyl or —CH(C$_2$H$_5$)(C$_4$H$_9$); and/or
R3 represents a divalent radical —R'3-O—C(O)—NH—R'4— in which R'3 and R'4, which may be identical or different, represent a divalent carbon-based radical chosen from a linear or branched C$_1$-C$_{30}$ alkyl group, a C$_4$-C$_{12}$ cycloalkyl group and a C$_4$-C$_{12}$ aryl group; or a mixture thereof; and especially R'3 represents a C$_1$-C$_4$ alkylene, especially 1,2-ethylene, and R'4 represents the divalent radical derived from isophorone.

A junction group that is most particularly preferred is the one having the formula:

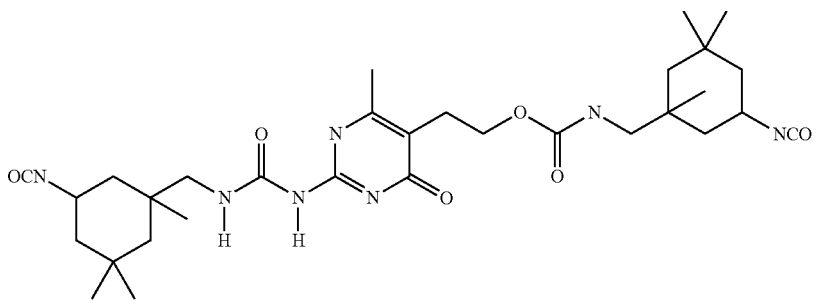

-continued

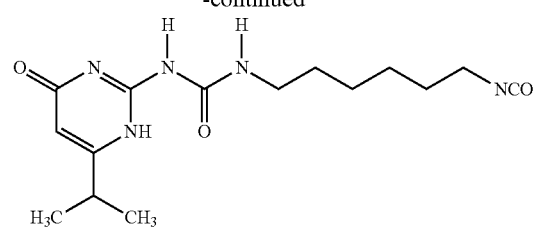

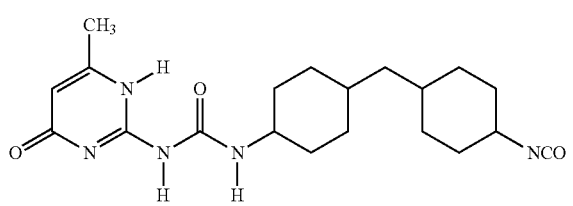

The junction groups bearing two isocyanate functions may have the formula:

Among the junction groups bearing an imidazole group, mention may be made of the following compound:

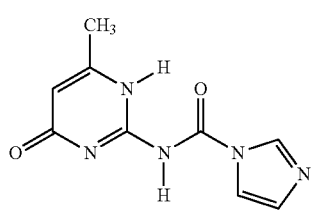 [SMILES: Cc1cc(=O)nc(NC(=O)n2ccnc2)[nH]1]

According to one particular embodiment of the invention, the junction groups may be attached to the oil by functionalization of the junction group with an isocyanate or imidazole.

According to another embodiment, it is possible to perform the reverse reaction by prefunctionalizing the oil with a diisocyanate.

As mentioned above (first mode), the compound according to the invention may thus result from the chemical reaction between an oil (HB)—(OH)$_m$(NH$_2$)$_n$ and a junction group (G)-(NCO)$_p$ or (G)-(imidazole)$_p$.

Preferably, the oil comprises only hydroxyl functions and the junction group comprises 1 or 2 isocyanate functions, which leads to the following reactions:

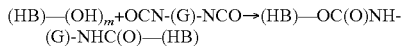

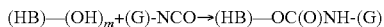

with m=integer greater than or equal to 1.

Preferably, the degree of grafting of the free OHs of the oil is between 1% and 100%, especially between 20% and 99% and better still between 50% and 95%; preferably, this degree is 100% (all the free OHs are functionalized with a junction group), especially when the oil initially comprises only one OH function.

The supramolecular compound according to the invention may be prepared via the processes usually used by those skilled in the art for forming a urethane bond, between the free OH functions of the oil and the isocyanate functions borne by the junction group.

By way of illustration, a general preparation process consists in:
- ensuring that the oil to be functionalized does not comprise any residual water,
- heating the oil comprising at least one reactive function, especially OH, to a temperature that may be between 60° C. and 140° C.;
- adding the junction group bearing the reactive functions, especially isocyanate;
- optionally stirring the mixture, under a controlled atmosphere, at a temperature of about 100-130° C.; for 1 to 24 hours;
- monitoring by infrared spectroscopy the disappearance of the characteristic band for isocyanates (between 2500 and 2800 cm$^{-1}$) so as to stop the reaction at the total disappearance of the peak, and then to allow the final product to cool to room temperature. The reaction may be performed in the presence of a solvent, especially methyltetrahydrofuran, tetrahydrofuran, toluene or butyl acetate; the reaction may also be performed without solvent, in which case the oil may serve as solvent.

It is also possible to add a conventional catalyst for forming a urethane bond. An example that may be mentioned is dibutyltin dilaurate.

Finally, the supramolecular compound may be washed and dried, or even purified, according to the general knowledge of a person skilled in the art.

According to the second embodiment, the reaction may include the following steps:

(i) functionalization of the oil with a diisocyanate according to the reaction scheme:

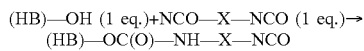

and then
(iia) either reaction with 6-methylisocytosine:

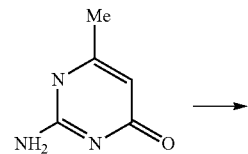

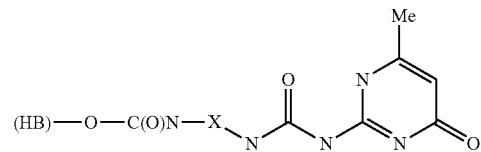

or
(iib) or reaction with 5-hydroxyethyl-6-methylisocytosine:

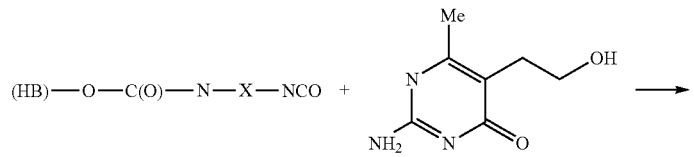

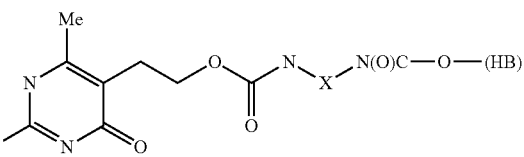

An illustration of such a reaction is given in Folmer et al., Adv. Mater., 12, 874-78 (2000).
The supramolecular compounds of the compositions according to the invention may especially correspond to the following structures:
ureidopyrimidone-functionalized octyldodecanol of structure:
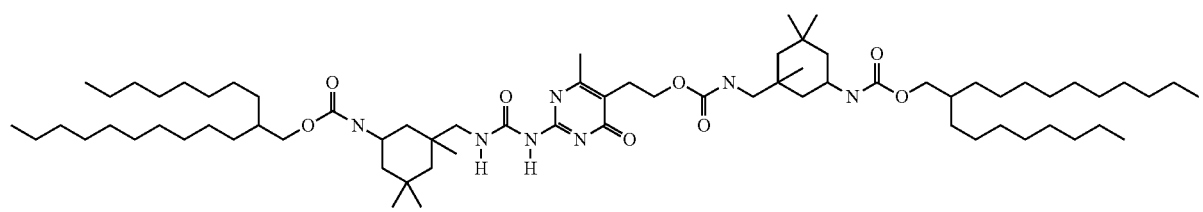
or of structure:
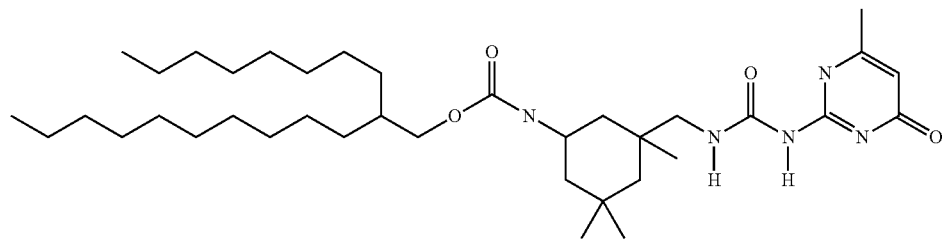 [SMILES: CCCCCCCCCCC(CCCCCCCC)COC(=O)NC1CC(C)(C)CC(C)(CNC(=O)Nc2nc(=O)cc(C)[nH]2)C1]
ureidopyrimidone-functionalized diisostearyl malate of structure:
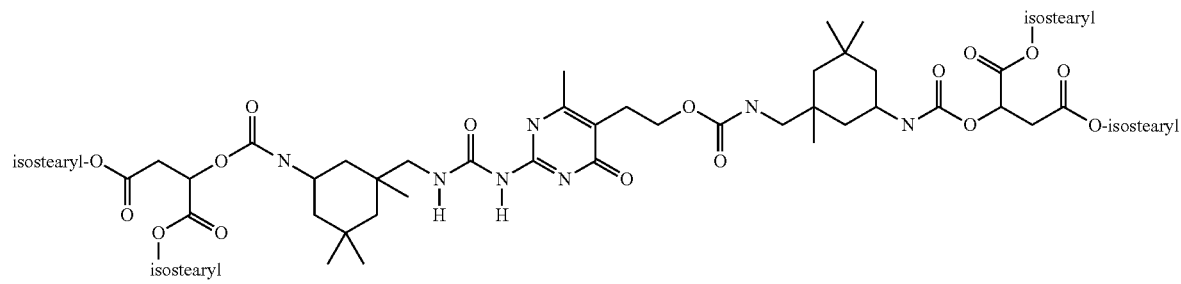

or of structure:
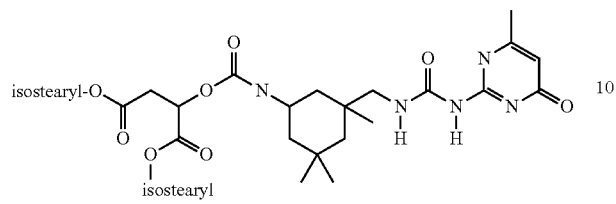
ureidopyrimidone-functionalized castor oil of structure:
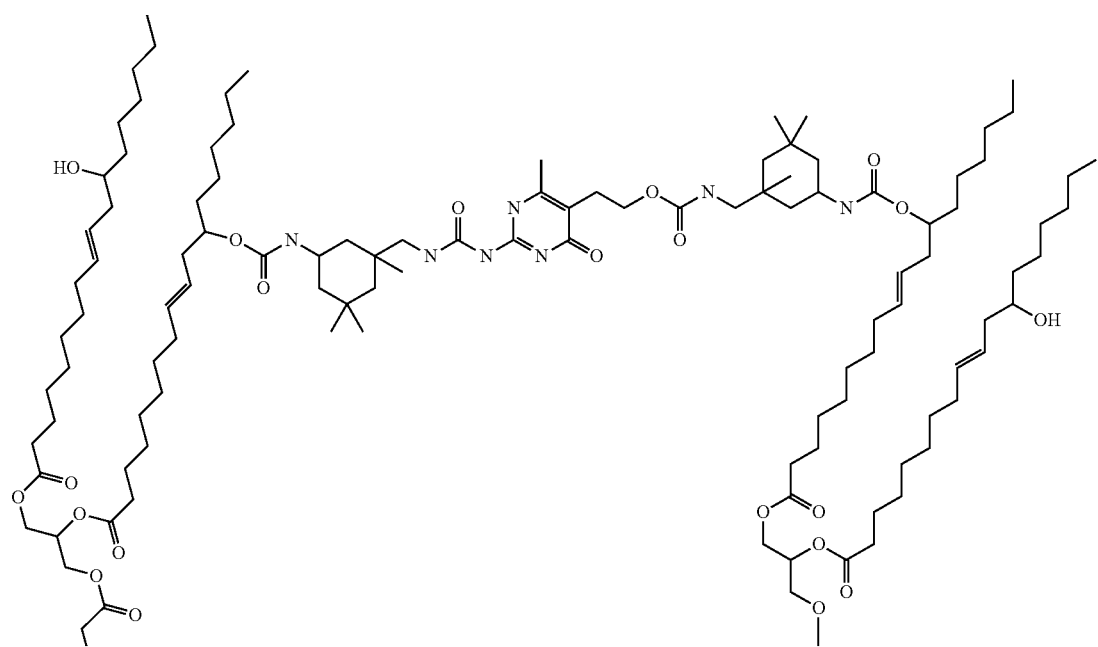
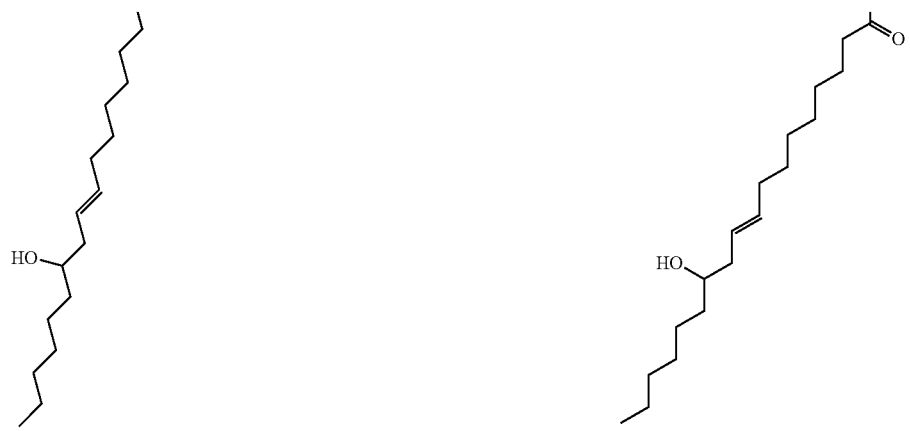

or of structure:
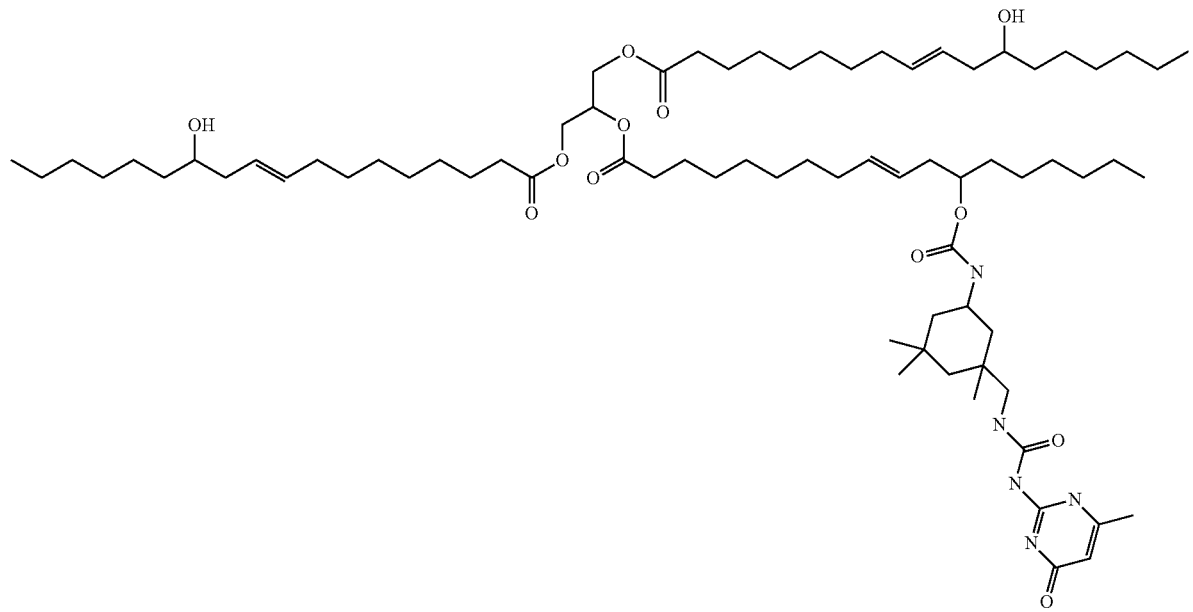 [SMILES: CCCCCCC(O)C/C=C/CCCCCCCC(=O)OCC(COC(=O)CCCCCCC/C=C/CC(O)CCCCCC)OC(=O)CCCCCCC/C=C/CC(CCCCCC)OC(=O)NC1CC(C)(C)CC(C)(CNC(=O)Nc2nc(=O)cc(C)[nH]2)C1]
ureidopyrimidone-functionalized 2-hexyldodecanol of structure:
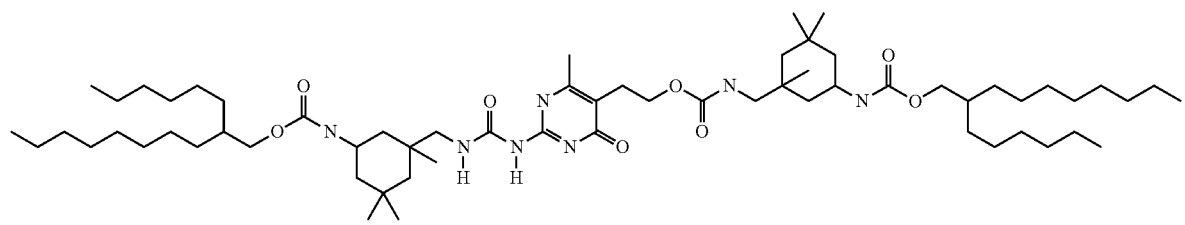
or of structure:
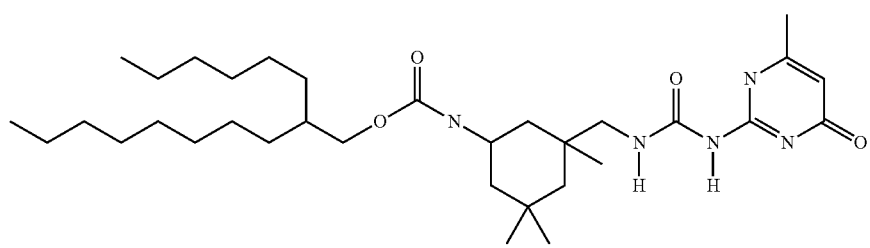 [SMILES: CCCCCCCCC(CCCCCC)COC(=O)NC1CC(C)(C)CC(C)(CNC(=O)Nc2nc(=O)cc(C)[nH]2)C1]

ureidopyrimidone-functionalized 2-decyltetradecanol of structure:

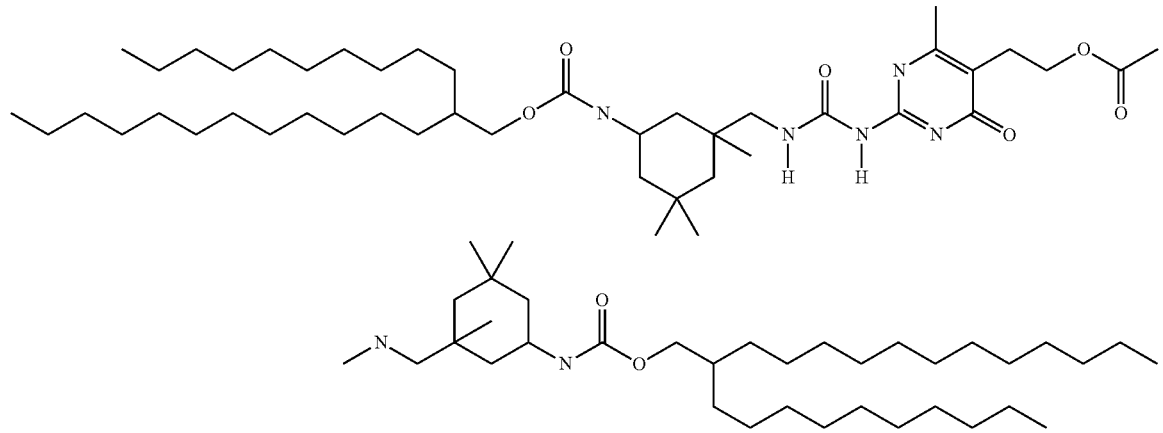

or of structure:

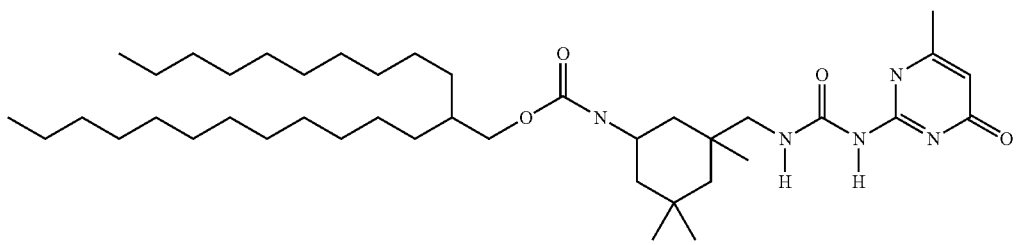 [SMILES: CCCCCCCCCCCCC(CCCCCCCCCC)COC(=O)NC1CC(C)(C)CC(C)(CNC(=O)Nc2nc(=O)cc(C)[nH]2)C1]

It has been found that the use of the compounds according to the invention may lead, after application of the composition to keratin materials, to the formation of a supramolecular polymer in the form of a physically crosslinked network, especially by means of hydrogen bonds, which is generally in the form of a film, and which has very good mechanical strength.

For the purposes of the invention, the term "supramolecular polymer" means a polymer chain or network formed from the assembly of non-polymeric compounds according to the invention with at least one other identical or different non-polymeric compound according to the invention, each assembly comprising at least one pair of identical or different paired junction groups.

For the purposes of the invention, the term "pair of paired junction groups" means two junction groups, each of which may optionally be borne by the same compound according to the invention, the two groups being connected together via 4H bonds.

Thus, the supramolecular polymer will have points of physical crosslinking provided by the H bonds between these pairs of junction groups. The physical crosslinking will ensure the maintenance and persistence of the cosmetic effect in a similar manner to chemical crosslinking, while at the same time allowing reversibility, i.e. the possibility of totally removing the deposit.

Preferably, the supramolecular compound according to the invention has a viscosity, measured at 125° C., of between 30 and 6000 mPa·s, especially between 150 and 4000 mPa·s, or even between 500 and 3500 mPa·s and better still between 750 and 3000 mPa·s.

The number-average molecular mass (Mn) of the supramolecular compound according to the invention is preferably between 180 and 8000, preferably from 200 to 6000, or even from 300 to 4000, better still from 400 to 3000 and preferentially from 500 to 1500.

The supramolecular compound according to the invention is advantageously soluble in the cosmetic oily media usually used, especially in plant oils, C6-C32 alkanes, C8-C32 fatty esters, C2-C7 short esters, C8-C32 fatty alcohols, and more particularly in media comprising at least isododecane, Parleam, isononyl isononanoate, octyldodecanol, a C12-C15 alkyl benzoate, butyl acetate or ethyl acetate, alone or as a mixture.

The term "soluble" means that the compound forms a clear solution in at least one solvent chosen from isododecane, Parleam, isononyl isononanoate, octyldodecanol, a C12-C15 alkyl benzoate, butyl acetate or ethyl acetate, in a proportion of at least 50% by weight, at 25° C.

The supramolecular compounds according to the invention may be used advantageously in a cosmetic composition, which moreover comprises a cosmetically acceptable medium, i.e. a medium that is compatible with keratin materials such as facial or bodily skin, the eyelashes, the eyebrows, the lips and the nails.

According to one particular mode, the composition according to the invention has a content of supramolecular compound (as starting material) of between 5% and 95% by weight, preferably between 10% and 95% by weight and better still preferably between 20% and 90% by weight relative to the total weight of the composition.

Preferably, the composition according to the invention has a content of supramolecular compound of between 4% and 20% by weight of active material, preferably between 6% and 15% by weight of active material and better still preferably between 8% and 13% by weight of active material relative to the total weight of the composition.

Specifically, the Applicant has observed that these contents of supramolecular compound in the composition of the invention correspond to the best compromise of desired remanence/non-tacky effect.

As examples of supramolecular compounds that may be used in the compositions according to the invention, mention may be made of the following compounds:

Compound 1: Ureidopyrimidone-functionalized octyldodecanol

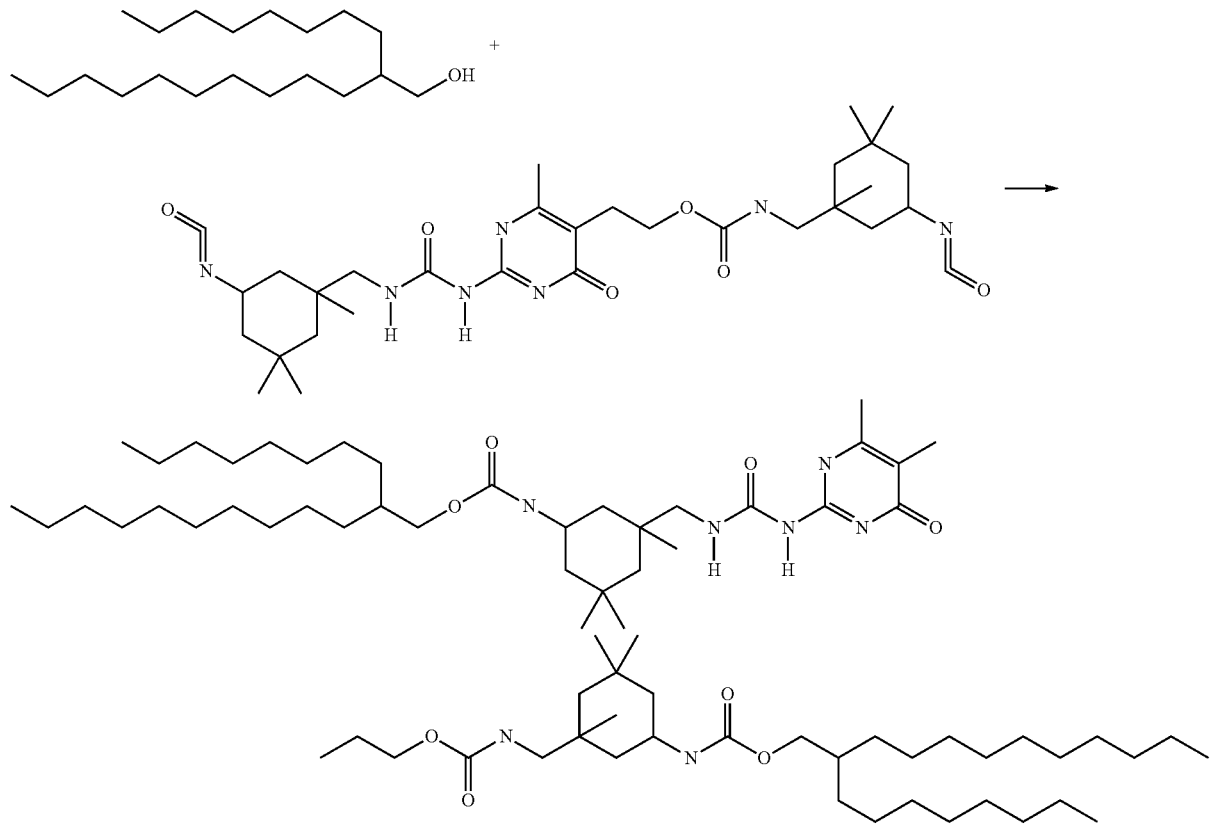

70 g of ureidopyrimidone diisocyanate are dissolved in methyltetrahydrofuran, under argon. 80.3 g of octyldodecanol in 100 ml of dichloromethane are added, under argon, followed by addition of 15 microlitres of dibutyltin dilaurate (catalyst). The reaction mixture is refluxed until the isocyanate peak (2250-2265 cm$^{-1}$) has disappeared on IR spectrometry.

The excess octyldodecanol is removed by successive washing of the reaction medium with methanol, followed by three extractions and drying over MgSO$_4$. After evaporation of the organic phase, 103 g of a pale yellow powder, characterized by 1H NMR (structure in conformity), are obtained.

This powder may be conveyed in isododecane, for example at a concentration of 10% by weight; this concentration may especially be up to 60% by weight in isododecane, which then leads to a solution that is viscous but still manipulable. It is thus found that by functionalizing with a ureidopyrimidone, the oil changes from a liquid to a solid, which can be conveyed in isododecane at concentrations above 30%.

When a solution comprising 50% by weight of compound in isododecane is applied, after evaporating off the solvent, a glossy transparent film is obtained, which shows good adhesion by fragmentation, and low resistance to friction.

Compound 2: Diisostearyl Malate Functionalized with a Ureidopyrimidone 15 g (0.0234 mol) of diisostearyl malate are dried under reduced pressure at 80° C. for 4 hours. 7.21 g (0.0117 mol) of ureidopyrimidone diisocyanate dissolved in 60 ml of methyltetrahydrofuran, and 12 µl of dibutyltin dilaurate catalyst are added. The mixture is heated at 95° C., under argon, for 26 hours (disappearance of the characteristic band for isocyanates on IR spectroscopy). 20 ml of methyltetrahydrofuran are added to the reaction mixture, and the resulting mixture is then filtered through Celite. After evaporating off the solvent and drying under reduced pressure, a pale yellow solid is obtained.

Compound 3: Castor Oil Functionalized with a Ureidopyrimidone 15 g of castor oil (0.016 mol) are dried under reduced pressure at 80° C. for 4 hours. A solution of 4.9 g of ureidopyrimidone diisocyanate (0.008 mol) in 60 ml of methyltetrahydrofuran, and 12 µl of dibutyltin dilaurate catalyst are added. The mixture is heated at 90° C. for 19 hours (total disappearance of the characteristic band for isocyanates on IR spectroscopy). At the end of the reaction, the solvent is evaporated off and the resulting product is dried under reduced pressure at 35° C. overnight.

A pale yellow solid gum is obtained.

Compound 4 (Comparative to Example 1): Octyldodecanol Functionalized with Isophorone

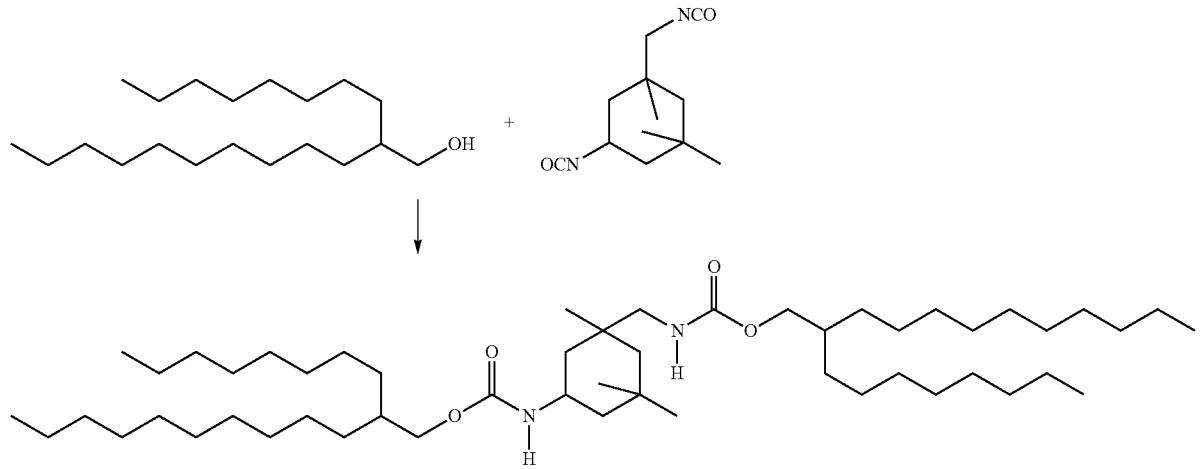

10 g of octyldodecanol are dried under reduced pressure at 80° C. for 2 hours, followed by addition of 3.72 g of isophorone diisocyanate and 25 microlitres of dibutyltin dilaurate catalyst. The mixture is heated at 95° C. under argon. The disappearance of the isocyanate is monitored by IR spectroscopy (disappearance of the band between 2250 and 2265 cm$^{-1}$, after heating for 12 hours).

A viscous oil that does not form a cohesive material is obtained.

Compound 5 (Comparative to Example 2): Diisostearyl Malate Functionalized with Isophorone 10 g (0.0159 mol) of diisostearyl malate are dried under reduced pressure at 80° C. for 3 hours. 1.77 g (0.079 mol) of isophorone diisocyanate and 2.5 µl of catalyst (dibutyltin dilaurate) are added under argon, and the reaction mixture is heated at 95° C. for 16 hours. During the reaction, the viscosity of the reaction medium increases. The reaction is stopped after disappearance of the characteristic peak for isocyanates on IR spectroscopy.

Compound 6 (Comparative to Example 3): Castor Oil Functionalized with Isophorone 15 g (0.016 mol) of castor oil are dried under reduced pressure at 80° C. for 6 hours. 1.78 g (0.008 mol) of isophorone diisocyanate and 12 µl of dibutyltin dilaurate catalyst are added, and the mixture is heated at 90° C. for 16 hours. The reaction is stopped after disappearance of the characteristic peak for isocyanates on IR spectroscopy.

EXAMPLE 7

The compounds prepared in Examples 1 to 6 are observed, visually and by feel, and the results are summarized in the following table:

|  | Physical appearance of the compound | Appearance of the film* Refractive index** (refractive index of non-functionalized oil) |
|---|---|---|
| Compound 1 | Yellow solid | Glossy tacky film, which does not dewet; uniform deposit. No transfer onto the fingers. 1.488 (1.46) |
| Compound 4 (comparative) | Viscous oil transparent | Film which dewets; non-uniform deposit. Transfers onto the fingers. 1.474 (1.46) |
| Compound 2 | Yellow solid | Glossy, sparingly tacky film, which does not dewet; uniform deposit. No transfer onto the fingers. 1.478 (1.462) |
| Compound 5 (comparative) | Viscous oil transparent | Glossy tacky film which dewets; non-uniform deposit. No transfer onto the fingers. 1.4598 (1.462) |
| Compound 3 | Yellow solid (solid gum) | Glossy, slightly tacky film; behaviour of a fragile solid, which does not dewet; uniform deposit. No transfer onto the fingers. 1.4852 (1.48) |
| Compound 6 (comparative) | Viscous oil transparent | Very tacky glossy film, which dewets; non-uniform deposit. Transfers onto the fingers. 1.4813 (1.48) |

*The films are formed from a solution containing 40% by weight of the compound, either in isododecane for Examples 1-2 and 4-5, or in tetrahydrofuran for compounds 3 and 6.
**For the refractive index measurements, all the films are formed from a solution containing 40% by weight of the compound in tetrahydrofuran; the refractive index is measured after evaporating off the solvent.

The term "film which does not dewet" means that, after deposition and evaporation of the solvent, a continuous, uniform "true" film is obtained.

The term "film which dewets" means that, after deposition and evaporation of the solvent, a non-uniform, discontinuous film "with holes" is obtained.

A tribometry test is performed on these deposits/films: the films are formed from a solution at 40% by weight in tetrahydrofuran, by deposition onto a nitrile elastomer, followed by drying for 24 hours at 25° C.

The tests are performed using a CSEM tribometer and equipped with a ball 6 mm in diameter. This ball, subjected to a 0.15 N load, rubs repeatedly on a film (10 to 20 μm thick). The rotation speed of the disk is set at 6.3 cm/s, which corresponds to a frequency of one revolution per second. The test is ended when wear is complete, or else is stopped after 1000 stress revolutions.

| | Observations |
|---|---|
| Compound 1 | The film remains unchanged (uniform) for 300 revolutions (no wear or brittleness); the material is thus cohesive; behaviour of a solid. |
| Compound 4 (comparative) | No measurement possible: the material has no cohesion, and behaves like an oil. |
| Compound 2 | The film remains unchanged (uniform) for 1000 revolutions (no wear or brittleness); the material is thus cohesive and does not wear out. |
| Compound 5 (comparative) | The material behaves like an oil, with a buttering effect when it is subjected to the wear test. |
| Example 3 | The film is sparingly brittle but remains unchanged for 10 revolutions; after 10 revolutions, the wear is more pronounced; this reflects the behaviour of a solid. |
| Compound 6 (comparative) | No measurement possible since no film was initially formed: behaviour of an oil |

It is thus found that there is no decrease in the refractive index after functionalization. The oil keeps its glossy nature, even when functionalized. It is also found that functionalization with ureidopyrimidones leads to films that are more or less tacky, but that do not transfer onto the fingers, unlike the comparative films.

Furthermore, and principally, in the case of the oils functionalized with isophorone (comparative), the films dewet and do not form a uniform deposit. In contrast, the films obtained with the compounds according to the invention do not dewet and are uniform and cohesive. The tribometry results confirm the cohesion properties obtained with the compounds of the invention.

Functionalization with ureidopyrimidones thus leads to materials that are cohesive enough to be able to ensure remanence of the deposit, which, incidentally, is glossy, superior to the remanence of the prior art (isophorone).

In summary: the gloss is maintained, the cohesion of the deposit is improved, and thus its remanence is improved.

Compound 8: Diisostearyl Malate Functionalized with a Ureidopyrimidone

Preparation Protocol

Preparation of the Supramolecular Oil: Diisostearyl Malate Functionalized with a Ureidopyrimidone 150 g of diisostearyl malate were added over 1 hour 20 minutes at 50° C. to a solution of 57.4 g of isophorone diisocyanate and 38.18 g of methyl isocytosine, in the presence of the catalyst dibutyltin dilaurate, with control of the exothermicity and under an inert atmosphere. Stirring was continued for 55 minutes at 50° C. after the addition, and 50 ml of propylene carbonate were then added. The temperature of the reaction medium was then raised to 140° C. with a contact time of 2 hours, with stirring. The temperature of the reaction medium was then lowered to 70° C., the medium was neutralized by addition of 30 ml of ethanol, and stirring was continued for 1 hour.

After adding 780 ml of ethyl acetate, the medium was filtered through Celite. After evaporating off the ethyl acetate, 400 ml of cyclohexane were added to the reaction medium, and the mixture was washed twice with an H₂O/EtOH mixture (2v/1v) saturated with NaCl. The organic phase was then stripped with isododecane, down to a viscous liquid, corresponding to the desired molecule in a solids content of 50%. For the purposes of the formulation, this dry extract may optionally be modified by adding isododecane to the medium.

Compound 9: 2-Hexyldecanol Functionalized with Ureidopyrimidone

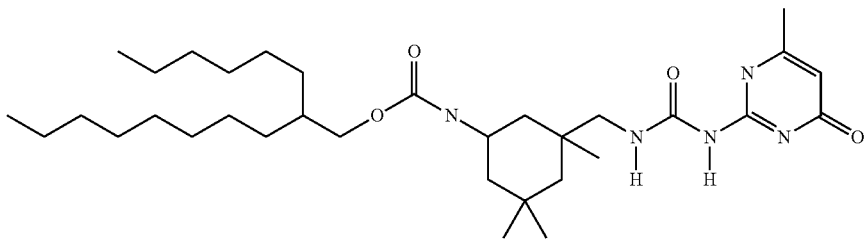 [SMILES: CCCCCCCCC(CCCCCC)COC(=O)NC1CC(C)(C)CC(C)(CNC(=O)Nc2nc(=O)cc(C)[nH]2)C1]

126.4 g of 2-hexyldecanol are heated at 60° C. under reduced pressure for 2 hours to dry them. After 2 hours, the oil is allowed to cool to 20° C. under argon, and is then added slowly, over 5 hours, to a mixture of 116 g of isophorone diisocyanate and 55 mg of DBTL catalyst at 50° C. At the end of the addition, the temperature of the reaction mixture is brought to 110° C., and 90 ml of propylene carbonate and 78.4 g of 6-methylisocytosine are then added, which produces a homogeneous white suspension. Stirring is continued at 110° C. for 2 hours, and the disappearance of the isocyanate is monitored by infrared spectroscopy. Disappearance of the peak at 2250 cm$^{-1}$ is observed. In parallel, the disappearance of the amine originating from the isocytosine is monitored by means of an amine assay. At the end of the reaction, 500 g of isododecane are added, at 100° C., and a slightly cloudy pale yellow solution is obtained. 300 ml of ethanol are added and stirring is continued for 2 hours. After filtering through Celite, the reaction mixture is stripped with isododecane at 80° C. in order to remove the alcohol and the propylene carbonate.

Finally, the desired product conveyed in isododecane, in a solids content of 50%, is obtained. The product is especially characterized by HPLC and GPC (structure confirmed).

Compound 10: 2-Hexyldecanol Functionalized with Ureidopyrimidone

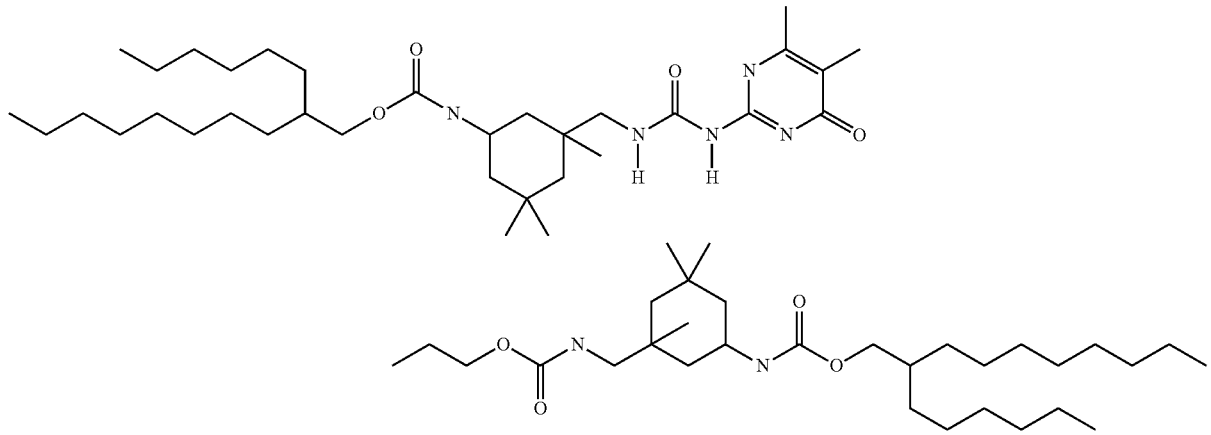

173.1 g of 2-hexyldecanol are heated at 60° C. under reduced pressure for 2 hours to dry them. After 2 hours, the oil is allowed to cool to 50° C. under argon, and is then added slowly, over 5 hours, to a mixture of 158.7 g of isophorone diisocyanate and 77 mg of DBTL catalyst at 50° C. At the end of the addition, the temperature of the reaction mixture is brought to 110° C., and 150 ml of propylene carbonate and 60.3 g of 5-hydroxyethyl-6-methylisocytosine are added, which produces a uniform white suspension. Stirring is continued at 110° C. for 5 hours, and the disappearance of the isocyanate is monitored by infrared spectroscopy. Disappearance of the peak at 2250 cm$^{-1}$ is observed. At the end of the reaction, the temperature of the reaction medium is reduced to 100° C., and 780 g of isododecane are added; a pale yellow cloudy mixture is obtained. 100 ml of ethanol are added and stirring is continued for 2 hours. After filtering through Celite, the reaction mixture is stripped with isododecane at 80° C. in order to remove the alcohol and the propylene carbonate.

Finally, the desired product conveyed in isododecane, in a solids content of 50%, is obtained. The product is especially characterized by HPLC and GPC (structure confirmed).

Compound 11: 2-Decyltetradecanol Functionalized with Ureidopyrimidone 126 g of 2-decyltetradecanol are heated at 100° C. under reduced pressure for 4 hours to dry them. After 2 hours, the oil is added, over 4 hours, at 50° C. and under argon, to a mixture of 94.7 g of isophorone diisocyanate and of DBTL catalyst (qs). Monitoring by assay of the isocyanate allows the reaction progress to be followed; at half-equivalence, 126 g of propylene carbonate and 53.3 g of 6-methylisocytosine are added. Stirring and heating are continued at 100° C. for 16 hours, and disappearance of the isocyanate is monitored by infrared spectroscopy. Disappearance of the peak at 2250 cm$^{-1}$ is observed. In parallel, the disappearance of the amine originating from the isocytosine is monitored by means of an amine assay. At the end of the reaction, the temperature is cooled to 50° C., 100 ml of ethanol are added and stirring is continued for 5 hours. After filtering through Celite and stripping with isododecane, the desired product conveyed in isododecane, at a solids content of 50%, is obtained. The product is especially characterized by GPC and HPLC coupled to mass spectroscopy.

Compound 12: Ureidopyrimidone-Functionalized Jarcol 24 (J24)

200 g of Jarcol I-24 are added at 50° C. to IPDI (1.1 eq. IPDI) in the presence of the catalyst, with control of the exothermicity and under an inert atmosphere. Stirring is continued after the addition for 30 minutes at 50° C. 1.3 equivalents of methylisocytosine (MIC) are then added to the mixture, followed by addition of 100 ml of propylene carbonate. The temperature of the reaction medium is then raised to 140° C., with a contact time of 1 hour at 140° C. The disappearance of the isocyanate functions is monitored by infrared spectroscopy, and the temperature of the medium is then lowered to 70° C., followed by addition of 30 ml of ethanol and stirring for 1 hour. After addition of ethyl acetate, the medium is filtered through filter paper. After evaporating off the ethyl acetate, cyclohexane is added, followed by 5 washes with a mixture of water saturated with NaCl/ethanol (2v/1v). The organic phase is then dried over Na$_2$SO$_4$, filtered and stripped with isododecane. A solution with a 50% solids content of oil functionalized with a ureidopyrimidone is then obtained.

Compound 13: Ureidopyrimidone-Functionalized Jarcol 20 (J20)

180 g of Jarcol I-20 are added at 50° C. to IPDI (1.1 eq. IPDI) in the presence of the catalyst, with control of the exothermicity and under an inert atmosphere.

Stirring is continued for 30 minutes at 50° C. 1.3 equivalents of MIC are added to the reaction medium, followed by addition of 100 ml of propylene carbonate.

The temperature of the reaction medium is then raised to 140° C. and stirring is continued for 1 hour at 140° C. The reaction is monitored by infrared spectroscopy, with monitoring of the decrease of the characteristic peak of the isocyanate function. The temperature is reduced to 70° C., 30 ml of ethanol are then added and the mixture is stirred for 1 hour. After addition of ethyl acetate, the medium is filtered through filter paper. After evaporating off the ethyl acetate, cyclohexane is added, followed by 5 washes with a mixture of water saturated with NaCl/ethanol (2v/1v). The organic phase is then dried over $Na_2SO_4$, filtered and stripped with isododecane. A solution with a 50% solids content of oil functionalized with a ureidopyrimidone is then obtained.

According to a second mode, the composition of the invention comprises at least one supramolecular compound such as the oil Jarcol 24 functionalized with a ureidopyrimidone, such as the product described in Example 12 above.

According to one particular mode, the composition according to the invention has a content of supramolecular compound of between 5% and 95% by weight, preferably between 10% and 95% by weight and better still preferably between 20% and 90% by weight relative to the total weight of the composition.

Preferably, the composition according to the invention has a content of supramolecular compound of between 4% and 20% by weight of active material, preferably between 6% and 15% by weight of active material and better still preferably between 8% and 13% by weight of active material relative to the total weight of the composition.

Physiologically Acceptable Medium

The term "physiologically acceptable medium" is intended to denote a medium that is particularly suitable for applying a composition of the invention to the skin and/or the lips, for instance the oils or organic solvents commonly used in cosmetic compositions.

The physiologically acceptable medium (acceptable tolerance, toxicology and feel) is generally adapted to the nature of the support onto which the composition is to be applied, and also to the form in which the composition is to be conditioned.

Silicone Oils

The composition according to the invention comprises at least one silicone oil.

According to one particular mode, the composition according to the invention comprises at least a first silicone oil and at least a second silicone oil that is different from the first one.

The term "oil" means a water-immiscible non-aqueous compound that is liquid at room temperature (25° C.) and at atmospheric pressure (760 mmHg).

The silicone oils that may be used according to the invention may be volatile and/or non-volatile. Thus, a composition according to the invention may contain a mixture of volatile and non-volatile silicone oil.

In particular, the volatile or non-volatile silicone oils that may be used in the invention preferably have a viscosity at 25° C. of less than 800 000 cSt, preferably less than or equal to 600 000 cSt and preferably less than or equal to 500 000 cSt. The viscosity of these silicone oils may be measured according to standard ASTM D-445.

The term "volatile oil" means an oil that can evaporate on contact with the skin in less than one hour, at room temperature (25° C.) and atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.1 to 10 mmHg).

The term "non-volatile" refers to an oil whose vapour pressure at room temperature and atmospheric pressure is non-zero and is less than 0.02 mmHg (2.66 Pa) and better still less than $10^{-3}$ mmHg (0.13 Pa).

According to one preferred embodiment, the composition according to the invention comprises at least one non-volatile silicone oil.

According to a preferred embodiment, the composition according to the invention comprises at least a first non-volatile silicone oil and a second non-volatile silicone oil that is different from the first one.

According to a preferred mode, the two non-volatile silicone oils are phenylated.

Non-Volatile Silicone Oil

The non-volatile silicone oil that may be used in the invention may be chosen especially from silicone oils especially with a viscosity at 25° C. of greater than or equal to 9 centistokes (cSt) ($9 \times 10^{-6}$ m$^2$/s) and preferably less than 800 000 cSt, preferably between 50 and 600 000 cSt and preferably between 100 and 500 000 cSt. The viscosity of this silicone may be measured according to standard ASTM D-445.

Among these silicone oils, two types of oil may be distinguished, according to whether or not they contain phenyl.

According to a first embodiment, the non-volatile silicone oil is a non-phenyl silicone oil. Non-phenyl non-volatile silicone oils that may be mentioned include:
- non-volatile polydimethylsiloxanes (PDMSs),
- PDMSs comprising alkyl or alkoxy groups, which are pendent and/or at the end of the silicone chain, these groups each containing from 2 to 24 carbon atoms,
- PDMSs comprising aliphatic and/or aromatic groups, or functional groups such as hydroxyl, thiol and/or amine groups,
- polyalkylmethylsiloxanes optionally substituted with a fluorinated group, such as polymethyltrifluoropropyldimethylsiloxanes,
- polyalkylmethylsiloxanes substituted with functional groups such as hydroxyl, thiol and/or amine groups,
- polysiloxanes modified with fatty acids, fatty alcohols or polyoxyalkylenes, and mixtures thereof.

According to one embodiment, a composition according to the invention contains at least one non-phenyl linear silicone oil.

Representative examples of these non-volatile linear silicone oils that may be mentioned include polydimethylsiloxanes; alkyl dimethicones; vinyl methyl methicones; and also silicones modified with optionally fluorinated aliphatic groups, or with functional groups such as hydroxyl, thiol and/or amine groups.

The non-phenyl linear silicone oil may be chosen especially from the silicones of formula (I):

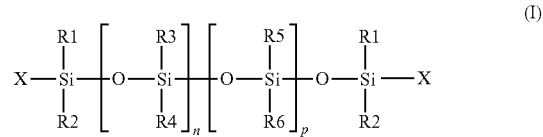

(I)

in which:
$R_1$, $R_2$, $R_5$ and $R_6$ are, together or separately, an alkyl radical containing 1 to 6 carbon atoms,
$R_3$ and $R_4$ are, together or separately, an alkyl radical containing from 1 to 6 carbon atoms, a vinyl radical, an amine radical or a hydroxyl radical,
X is an alkyl radical containing from 1 to 6 carbon atoms, a hydroxyl radical or an amine radical, n and p are integers chosen so as to have a fluid compound, in particular whose viscosity at 25° C. is between 9 centistokes (cSt) ($9\times10^{-6}$ m$^2$/s) and 800 000 cSt.

As non-volatile silicone oils that may be used according to the invention, mention may be made of those for which:
- the substituents $R_1$ to $R_6$ and X represent a methyl group, and p and n are such that the viscosity is 500 000 cSt, such as the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning,
- the substituents $R_1$ to $R_6$ and X represent a methyl group, and p and n are such that the viscosity is 60 000 cSt, such as the product sold under the name Dow Corning 200 Fluid 60000 CS by the company Dow Corning, and the product sold under the name Wacker Belsil DM 60 000 by the company Wacker,
- the substituents $R_1$ to $R_6$ and X represent a methyl group, and p and n are such that the viscosity is 350 cSt, such as the product sold under the name Dow Corning 200 Fluid 350 CS by the company Dow Corning,
- the substituents $R_1$ to $R_6$ represent a methyl group, the group X represents a hydroxyl group, and n and p are such that the viscosity is 700 cSt, such as the product sold under the name Baysilone Fluid T0.7 by the company Momentive.

According to one preferred embodiment, the composition according to the invention comprises at least one non-phenyl linear silicone oil.

According to one preferred embodiment variant, a composition according to the invention contains at least one non-volatile phenyl silicone oil.

Representative examples of these non-volatile phenyl silicone oils that may be mentioned include:
- the phenyl silicone oils corresponding to the following formula:

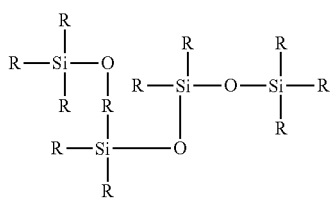

(I)

in which the groups R represent, independently of each other, a methyl or a phenyl, with the proviso that at least one group R represents a phenyl. Preferably, in this formula, the phenyl silicone oil comprises at least three phenyl groups, for example at least four, at least five or at least six.
- the phenyl silicone oils corresponding to the following formula:

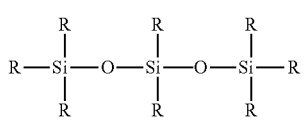

(II)

in which the groups R represent, independently of each other, saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl, or a phenyl, with the proviso that at least one group R is a phenyl group. Preferably, in this formula, the said organopolysiloxane comprises at least three phenyl groups, for example at least four or at least five. Mixtures of the phenyl organopolysiloxanes described previously may be used. Examples that may be mentioned include mixtures of triphenyl, tetraphenyl or pentaphenyl organopolysiloxanes.
- the phenyl silicone oils corresponding to the following formula:

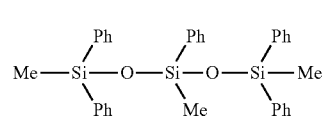

(III)

in which Me represents methyl, Ph represents phenyl. Such a phenyl silicone is especially manufactured by Dow Corning under the reference PH-1555 HRI or Dow Corning 555 Cosmetic Fluid (chemical name: 1,3,5-trimethyl-1,1,3,5,5-pentaphenyl trisiloxane; INCI name: trimethyl pentaphenyl trisiloxane). The reference Dow Corning 554 Cosmetic Fluid may also be used.
- the phenyl silicone oils corresponding to the following formula:

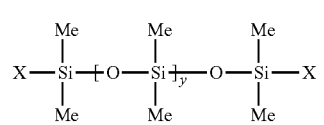

(IV)

in which Me represents methyl, y is between 1 and 1000 and X represents —CH$_2$—CH(CH$_3$)(Ph).
- the phenyl silicone oils corresponding to formula (V) below:

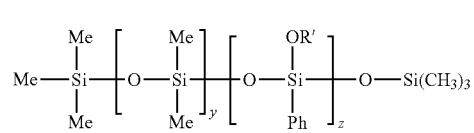

(V)

in which Me is methyl and Ph is phenyl, OR' represents a group —OSiMe$_3$ and y is 0 or ranges between 1 and 1000, and z ranges between 1 and 1000, such that compound (V) is a non-volatile oil.

According to a first embodiment, y ranges between 1 and 1000. Use may be made, for example, of trimethyl siloxyphenyl dimethicone, sold especially under the reference Belsil PDM 1000 sold by the company Wacker.

According to a second embodiment, y is equal to 0. Use may be made, for example, of phenyl trimethylsiloxy trisiloxane, sold especially under the reference Dow Corning 556 Cosmetic Grade Fluid.
- the phenyl silicone oils corresponding to formula (VI) below, and mixtures thereof:

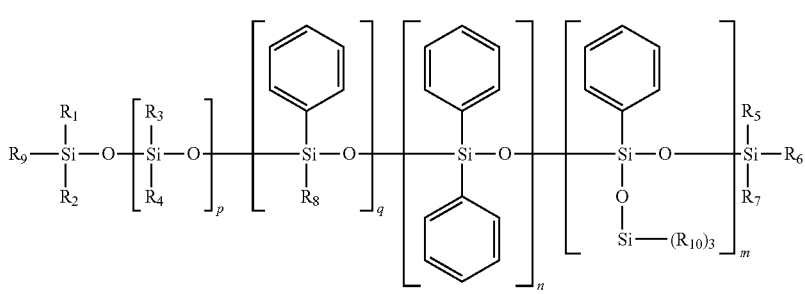
(VI)

in which:

R₁ to R₁₀, independently of each other, are saturated or unsaturated, linear, cyclic or branched $C_1$-$C_{30}$ hydrocarbon-based radicals, m, n, p and q are, independently of each other, integers between 0 and 900, with the proviso that the sum m+n+q is other than 0.

Preferably, the sum m+n+q is between 1 and 100. Preferably, the sum m+n+p+q is between 1 and 900 and better still between 1 and 800. Preferably, q is equal to 0.

the phenyl silicone oils corresponding to formula (VII) below, and mixtures thereof:

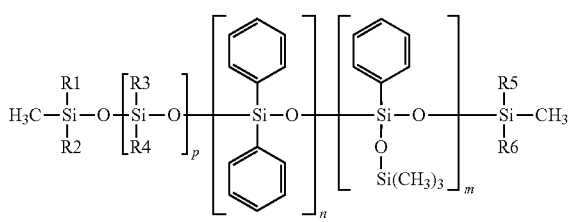
(VII)

in which:

R₁ to R₆, independently of each other, are saturated or unsaturated, linear, cyclic or branched $C_1$-$C_{30}$ hydrocarbon-based radicals, m, n and p are, independently of each other, integers between 0 and 100, with the proviso that the sum n+m is between 1 and 100.

Preferably, R₁ to R₆, independently of each other, represent a saturated, linear or branched $C_1$-$C_{30}$ and especially $C_1$-$C_{12}$ hydrocarbon-based radical and in particular a methyl, ethyl, propyl or butyl radical.

R₁ to R₆ may especially be identical, and in addition may be a methyl radical.

Preferably, m=1 or 2 or 3, and/or n=0 and/or p=0 or 1 may apply, in formula (VII).

the phenyl silicone oils corresponding to formula (VIII), and mixtures thereof:

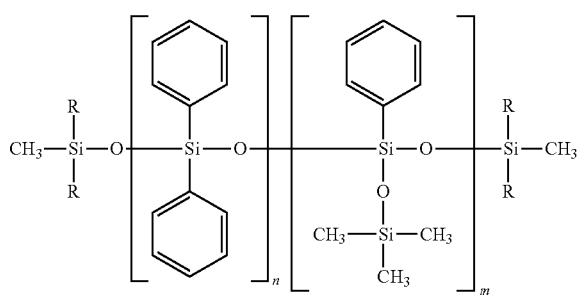
(VIII)

in which:

R is a $C_1$-$C_{30}$ alkyl radical, an aryl radical or an aralkyl radical, n is an integer ranging from 0 to 100, and m is an integer ranging from 0 to 100, with the proviso that the sum n+m ranges from 1 to 100.

In particular, the radicals R of formula (VIII) and R₁ to R₁₀ defined previously may each represent a linear or branched, saturated or unsaturated alkyl radical, especially of $C_2$-$C_{20}$, in particular $C_3$-$C_{16}$ and more particularly $C_4$-$C_{10}$, or a monocyclic or polycyclic $C_6$-$C_{14}$ and especially $C_{10}$-$C_{13}$ aryl radical, or an aralkyl radical whose aryl and alkyl residues are as defined previously.

Preferably, R of formula (VIII) and R₁ to R₁₀ may each represent a methyl, ethyl, propyl, isopropyl, decyl, dodecyl or octadecyl radical, or alternatively a phenyl, tolyl, benzyl or phenethyl radical.

According to one embodiment, a phenyl silicone oil of formula (VIII) with a viscosity at 25° C. of between 5 and 1500 mm²/s (i.e. 5 to 1500 cSt), and preferably with a viscosity of between 5 and 1000 mm²/s (i.e. 5 to 1000 cSt), may be used.

As phenyl silicone oils of formula (VIII), it is especially possible to use phenyl trimethicones such as DC556 from Dow Corning (22.5 cSt), the oil Silbione 70663V30 from Rhône-Poulenc (28 cSt) or diphenyl dimethicones such as Belsil oils, especially Belsil PDM1000 (1000 cSt), Belsil PDM 200 (200 cSt) and Belsil PDM 20 (20 cSt) from Wacker. The values in parentheses represent the viscosities at 25° C.

the phenyl silicone oils corresponding to the following formula, and mixtures thereof:

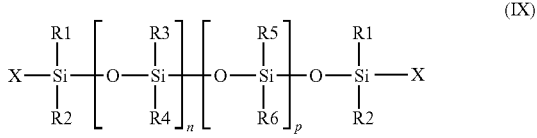

(IX)

in which:
- R₁, R₂, R₅ and R₆ are, together or separately, an alkyl radical containing 1 to 6 carbon atoms,
- R₃ and R₄ are, together or separately, an alkyl radical containing from 1 to 6 carbon atoms or an aryl radical,
- X is an alkyl radical containing from 1 to 6 carbon atoms, a hydroxyl radical or a vinyl radical,
- n and p being chosen so as to give the oil a weight-average molecular mass of less than 200 000 g/mol, preferably less than 150 000 g/mol and more preferably less than 100 000 g/mol.
- the phenyl silicones are more particularly chosen from phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and mixtures thereof.

More particularly, the phenyl silicones are chosen from phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and mixtures thereof.

Preferably, the weight-average molecular weight of the non-volatile phenyl silicone oil according to the invention ranges from 500 to 10 000 g/mol.

Preferably, the silicone oil is chosen from:
i) phenyl silicone oils, in particular of formula (II) or (VII) below:

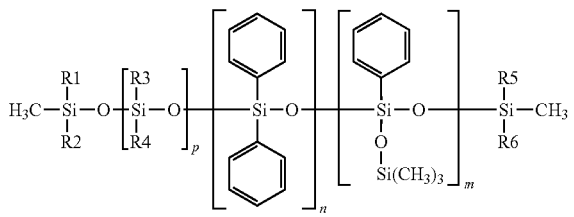

(VII)

in which:
- R1 to R6, independently of each other, are saturated or unsaturated, linear, cyclic or branched $C_1$-$C_{30}$ hydrocarbon-based radicals,
- m, n and p are, independently of each other, integers between 0 and 100, with the proviso that the sum n+m is between 1 and 100;

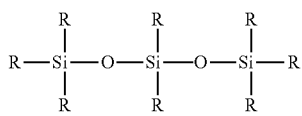

(II)

in which the groups R represent, independently of each other, a methyl or a phenyl, at least one of the groups R being a phenyl, ii) linear or cyclic polydimethylsiloxanes (PDMSs),
iii) polydimethylsiloxanes comprising alkyl or alkoxy groups, which are pendent and/or at the end of the silicone chain, these groups each containing from 2 to 24 carbon atoms.

A phenyl silicone oil that is preferably used is an oil of formula (V) or of formula (II) (preferably of formula (III)).

As preferred non-volatile silicone oils, examples that may be mentioned include silicone oils such as:
- phenyl silicones (also known as phenyl silicone oil) for instance Belsil PDM 1000 from the company Wacker (MW=9000 g/mol) (cf. formula (V) above), phenyl trimethicones (such as the phenyl trimethicone sold under the trade name DC556 by Dow Corning), phenyl dimethicones, phenyltrimethylsiloxydiphenylsiloxanes, diphenyl dimethicones, diphenylmethyldiphenyltrisiloxanes, 2-phenylethyl trimethylsiloxysilicates, trimethylpentaphenyl trisiloxane (such as the product sold under the name Dow Corning PH-1555 HRI Cosmetic fluid by Dow Corning) (cf. formula (III) above),
- non-volatile polydimethylsiloxanes (PDMSs), polydimethylsiloxanes comprising alkyl or alkoxy groups, which are pendent and/or at the end of the silicone chain, these groups each containing from 2 to 24 carbon atoms,
- and mixtures thereof.

According to a preferred mode, a composition according to the invention comprises at least a first non-volatile phenyl silicone oil and a second non-volatile silicone oil that is different from the first one.

Advantageously, the first and second silicone oils used in the composition of the invention are such that they are mutually incompatible, at least in certain defined ratios (they form a transparent homogeneous mixture that is colourless at room temperature, at least in certain first oil/second oil ratios) and form, in the presence of the supramolecular compound according to the invention, a two-phase mixture at room temperature (at least one of the non-volatile silicone oils of the combination used being incompatible with the said supramolecular compound).

After application to keratin materials, in particular the lips, the combination of these two non-volatile silicone oils and of the supramolecular compound makes it possible to obtain a thin film that is comfortable (not tacky, not drying-out), which shows satisfactory gloss and has good remanence (of the gloss and of the colour when the composition contains dyestuffs) and homogeneity of the deposit.

Thus, according to one particular mode, a subject of the present invention is a cosmetic composition, preferably for making up and/or caring for keratin materials, especially the skin or the lips, in particular the lips, comprising, in a cosmetically acceptable medium, at least:
(a) a compound A (referred to, in the context of the present patent application, as a supramolecular compound) that may be obtained by reaction between:
- at least one oil bearing at least one nucleophilic reactive function chosen from OH and $NH_2$, and
- at least one junction group capable of establishing hydrogen bonds with one or more partner junction groups, each pairing of a junction group involving at least three hydrogen bonds, the said junction group bearing at least one isocyanate or imidazole reactive function capable of reacting with the reactive function borne by the oil, the said junction group also comprising at least one unit of formula (I) or (II):

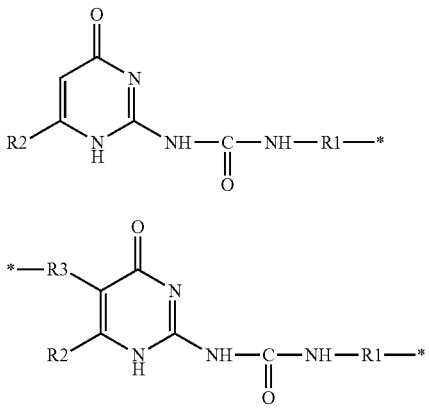

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;

R2 represents a hydrogen atom or a linear, branched or cyclic, saturated or unsaturated, optionally aromatic, C1-C32 carbon-based and especially hydrocarbon-based radical, which may comprise one or more heteroatoms chosen from O, N, S, F, Si and P;

(b) at least two distinct non-volatile silicone oils chosen from:

i) phenyl silicone oils of formula (II) or (VII) below:

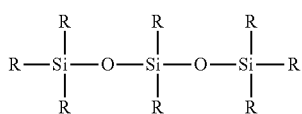

in which the groups R represent, independently of each other, saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably a methyl, or a phenyl, at least one of the groups R being a phenyl group, in which:
R1 to R6, independently of each other, are saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl, m, n and p are, independently of each other, integers between 0 and 100, with the proviso that the sum n+m is between 1 and 100;

ii) linear or cyclic polydimethylsiloxanes (PDMSs),
iii) polydimethylsiloxanes comprising alkyl or alkoxy groups, which are pendent and/or at the end of the silicone chain, these groups each containing from 2 to 24 carbon atoms, it being understood that:
at least one of the non-volatile silicone oils is chosen from the phenyl silicone oils of formula (II) or of formula (VII) with p=0 (also known as oil that is "compatible" with the supramolecular compound in the description) and at least one of the said non-volatile silicone oils is chosen from the phenyl silicone oils of formula (VII) with p≠0 and $R_3$ and $R_4$ are saturated or unsaturated, linear or branched $C_1$-$C_{30}$ and especially $C_1$-$C_{12}$ hydrocarbon-based radicals, and in particular a methyl, ethyl, propyl or butyl radical, preferably methyl, linear or cyclic polydimethylsiloxanes (PDMSs), and polydimethylsiloxanes comprising alkyl or alkoxy groups, which are pendent and/or at the end of the silicone chain, these groups each containing from 2 to 24 carbon atoms (also known as oil that is "incompatible" with the supramolecular compound in the description),
and (d) advantageously at least one agent for structuring the liquid fatty phase, chosen especially from solid and/or pasty fatty substances, in particular waxes, preferably apolar waxes.

According to another particular mode, a subject of the present invention is a cosmetic composition, preferably for making up and/or caring for keratin materials, especially the skin or the lips, in particular the lips, comprising, in a cosmetically acceptable medium, at least:

(a) a compound A (referred to, in the context of the present patent application, as a supramolecular compound) that may be obtained by reaction between:
at least one oil bearing at least one nucleophilic reactive function chosen from OH and NH₂, and
at least one junction group capable of establishing hydrogen bonds with one or more partner junction groups, each pairing of a junction group involving at least three hydrogen bonds, the said junction group bearing at

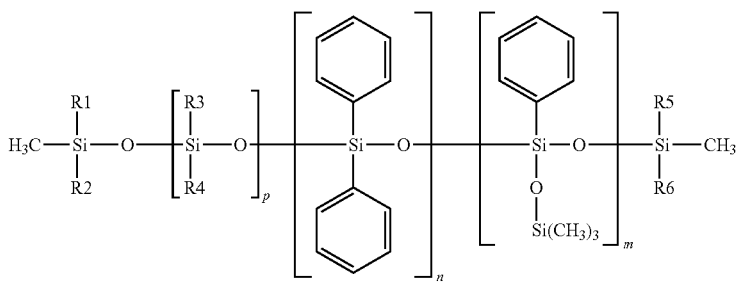

least one isocyanate or imidazole reactive function capable of reacting with the reactive function borne by the oil, the said junction group also comprising at least one unit of formula (I) or (II):

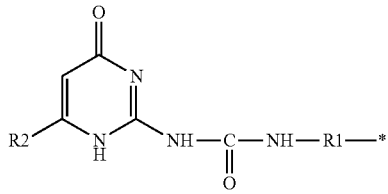

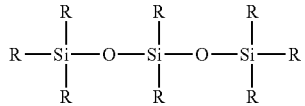

in which the groups R represent, independently of each other, saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl, or a phenyl, at least one of the groups R being a phenyl group,

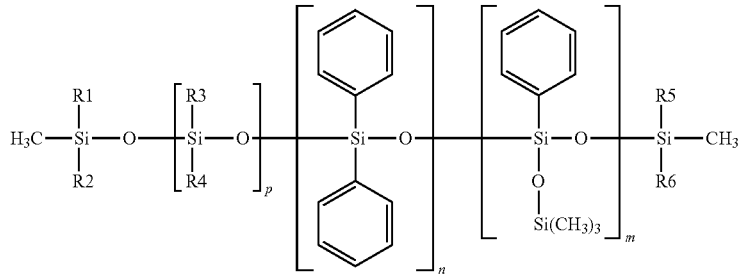

-continued

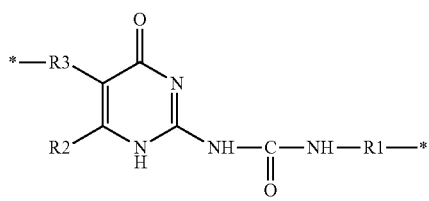

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;
R2 represents a hydrogen atom or a linear, branched or cyclic, saturated or unsaturated, optionally aromatic, C1-C32 carbon-based and especially hydrocarbon-based radical, which may comprise one or more heteroatoms chosen from O, N, S, F, Si and P;
(b) at least two distinct non-volatile silicone oils of formula (X), (II) or (VII) below:

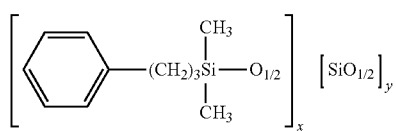

in which x/y is equal to 2 with y ranging from 1 to 30, in which:
R1 to R6, independently of each other, are saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl,
m, n and p are, independently of each other, integers between 0 and 100, with the proviso that the sum n+m is between 1 and 100;
ii) linear or cyclic polydimethylsiloxanes (PDMSs),
iii) polydimethylsiloxanes comprising alkyl or alkoxy groups, which are pendent and/or at the end of the silicone chain, these groups each containing from 2 to 24 carbon atoms,
it being understood that:
at least one of the non-volatile silicone oils is chosen from the phenyl silicone oils of formula (X) and
at least one of the said non-volatile silicone oils is chosen from the phenyl silicone oils of formula (VII) with p≠0 and $R_3$ and $R_4$ are saturated or unsaturated, linear or branched $C_1$-$C_{30}$ and especially $C_1$-$C_{12}$ hydrocarbon-based radicals, and in particular a methyl, ethyl, propyl or butyl radical, preferably methyl, linear or cyclic polydimethylsiloxanes (PDMSs), and polydimethylsiloxanes comprising alkyl or alkoxy groups, which are pendent and/or at the end of the silicone chain, these groups each containing from 2 to 24 carbon atoms (also known as oil that is "incompatible" with the supramolecular compound in the description),
and
(d) advantageously at least one agent for structuring the liquid fatty phase, chosen especially from waxes and/or pasty fatty substances, in particular waxes, preferably apolar waxes.

According to another particular mode, a subject of the present invention is a cosmetic composition, preferably for making up and/or caring for keratin materials, especially the skin or the lips, in particular the lips, comprising, in a cosmetically acceptable medium, at least:

(a) a compound A (referred to, in the context of the present patent application, as a supramolecular compound) that may be obtained by reaction between:

at least one oil bearing at least one nucleophilic reactive function chosen from OH and $NH_2$, and at least one junction group capable of establishing hydrogen bonds with one or more partner junction groups, each pairing of a junction group involving at least three hydrogen bonds, the said junction group bearing at least one isocyanate or imidazole reactive function capable of reacting with the reactive function borne by the oil, the said junction group also comprising at least one unit of formula (I) or (II):

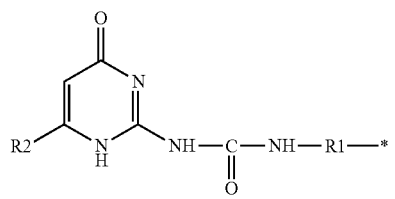
(I)

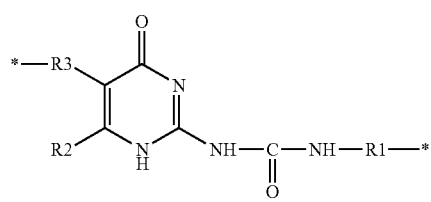
(II)

(b) at least two distinct non-volatile silicone oils of formula (III), (X), (II) or (VII) below:

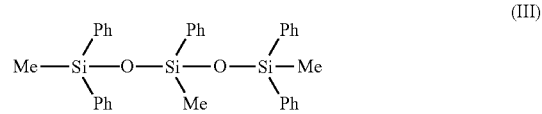
(III)

in which Me represents methyl, Ph represents phenyl,

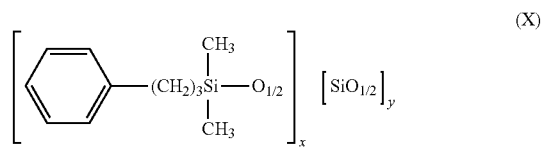
(X)

in which x/y is equal to 2 with y ranging from 1 to 30,

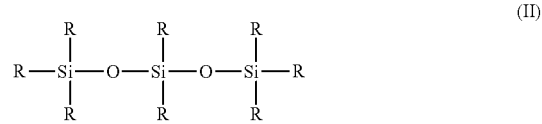
(II)

in which the groups R represent, independently of each other, saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl, or a phenyl, at least one of the groups R being a phenyl group,

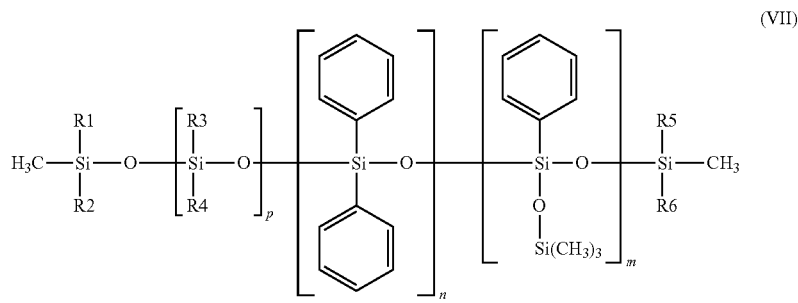
(VII)

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;
R2 represents a hydrogen atom or a linear, branched or cyclic, saturated or unsaturated, optionally aromatic, C1-C32 carbon-based and especially hydrocarbon-based radical, which may comprise one or more heteroatoms chosen from O, N, S, F, Si and P;

in which:

R1 to R6, independently of each other, are saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl, m, n and p are, independently of each other, integers between 0 and 100, with the proviso that the sum n+m is between 1 and 100;

ii) linear or cyclic polydimethylsiloxanes (PDMSs), iii) polydimethylsiloxanes comprising alkyl or alkoxy groups, which are pendent and/or at the end of the silicone chain, these groups each containing from 2 to 24 carbon atoms, and in particular a methyl, ethyl, propyl or butyl radical, preferably methyl, or a phenyl, at least one of the groups R being a phenyl group.

According to another particular mode, the composition according to the invention comprises, as first non-volatile silicone oil, a phenyl oil of formula (VII)

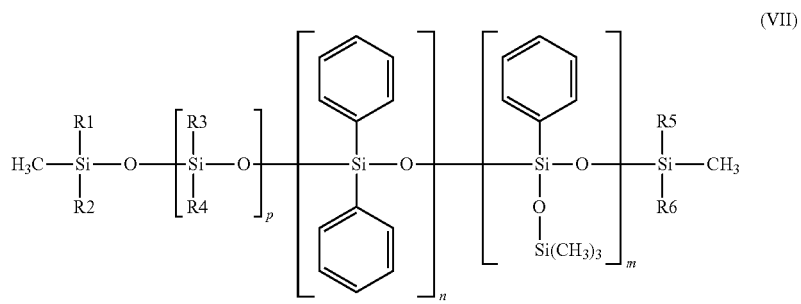

it being understood that:
- at least one of the non-volatile silicone oils is chosen from the phenyl silicone oils of formula (III) and
- at least one of the said non-volatile silicone oils is chosen from the phenyl silicone oils of formula (II), (VII) or (X), and (d) advantageously at least one agent for structuring the liquid fatty phase, chosen especially from waxes and/or pasty fatty substances, in particular waxes, preferably apolar waxes.

According to this latter embodiment, a person skilled in the art will select a content of oil of formula (III) such that it is compatible or incompatible with the supramolecular compound and will adapt in consequence the choice of the second oil of formula (II), (VII) or (X) to have at the end a mixture of a compatible oil/an incompatible oil with the supramolecular compound.

Preferably, the composition as described in the above embodiments comprises at least one agent for structuring the liquid fatty phase, chosen especially from waxes and/or pasty fatty substances, in particular waxes, in a content of less than or equal to 20% by weight relative to the total weight of the composition, especially ranging from 1% to 20% by weight, in particular from 1% to 15% by weight and better still from 1% to 10% by weight relative to the total weight of the said composition.

Examples of corresponding oils are described previously.

First Non-Volatile Silicone Oil

According to one particular mode, the composition according to the invention comprises, as first non-volatile silicone oil, a phenyl oil of formula (II)

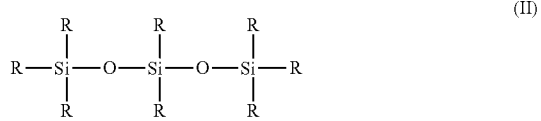

in which the groups R represent, independently of each other, saturated or unsaturated, linear, cyclic or branched $C_1$-$C_{30}$ and especially $C_1$-$C_{12}$ hydrocarbon-based radicals, in which:
- R1 to R6, independently of each other, are saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl,
- m and n are, independently of each other, integers between 0 and 100, with the proviso that the sum n+m is between 1 and 100;
- p=0.

In particular, R1, R2, R5 and R6 are identical and are methyl groups; mention may be made especially of Diphenylsiloxyphenyl trimethicone (US INCI name) sold especially under the trade name KF-56A by Shin-Etsu.

According to a particular preferred mode, the composition comprises at least, as first non-volatile silicone oil, a phenyl oil of formula (VII) as defined above with p=0 and n=0 and R1, R2, R5 and R6 are identical and are methyl groups; mention may be made especially of Phenyltrimethylsiloxytrisiloxane (US INCI name) sold especially under the reference Dow Corning 556 Cosmetic Grade Fluid.

According to another particular mode, the composition comprises, as first non-volatile silicone oil, a phenyl oil of formula (X)

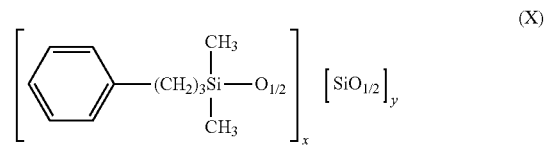

in which x/y is equal to 2 with y ranging from 1 to 30.

These non-volatile phenyl silicone oils of formula (X) are also known as phenyl silicone resins of low viscosity (50 to 1000 cSt) and are described especially in patents U.S. Pat. Nos. 5,338,538 and 5,397,566.

Mention may be made especially of Phenylpropyldimethyl siloxysilicate (US INCI name) sold especially under the trade name Silshine 151 by the company Momentive Performance Materials.

According to another particular mode, the composition comprises at least, as first non-volatile silicone oil, a phenyl oil of formula (III)

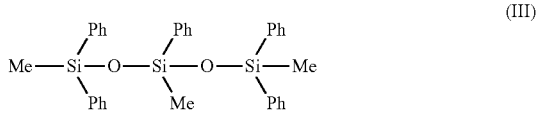

(III)

in which Me represents methyl, Ph represents phenyl.

The Applicant has shown, specifically, that according to the ratio of supramolecular compound/oil of formula (III), this oil could be compatible (ratio 50/50 and 70/30) or incompatible (ratio 30/70). Consequently, in order to be in the condition of a "compatible" first oil, use will be made especially of a content of oil of formula (III) that is less than or equal to the content of supramolecular compound.

According to one particular mode, the first non-volatile silicone oil is present in the composition in a content ranging from 10% to 60% by weight relative to the total weight of the said composition, in particular from 20% to 50% by weight and especially from 25% to 40% by weight relative to the total weight of the said composition.

Second Non-Volatile Silicone Oil

According to one particular mode, the composition according to the invention comprises, as second non-volatile silicone oil, an oil chosen from linear or cyclic polydimethylsiloxanes (PDMSs), in particular the linear polydimethylsiloxanes of formula (XI)

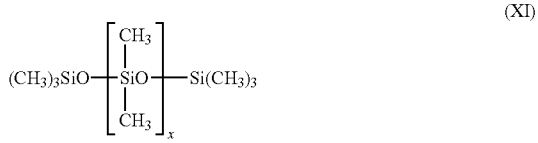

(XI)

the US INCI name of which is Dimethicone.

According to another particular preferred mode, the composition according to the invention comprises, as second non-volatile silicone oil, a phenyl oil of formula (VII)

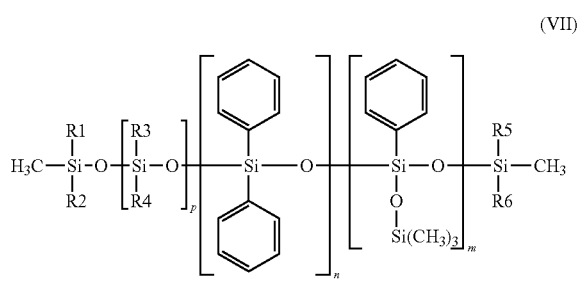

(VII)

in which:

R1 to R6, independently of each other, are saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl, m and n are, independently of each other, integers between 0 and 100, with the proviso that the sum n+m is between 1 and 100;

p≠0 and $R_3$ and $R_4$ are saturated or unsaturated, linear or branched $C_1$-$C_{30}$ and especially $C_1$-$C_{12}$ hydrocarbon-based radicals, and in particular a methyl, ethyl, propyl or butyl radical, preferably methyl.

According to one particular mode, n=0 and R1 to R6 are identical and are methyl radicals; mention may be made especially of Trimethylsiloxyphenyl dimethicone (US INCI name) sold especially under the reference Wacker-Belsil PDM 1000 by Wacker.

According to another particular mode, m=0 and R1 to R6 are identical and are methyl radicals; mention may be made especially of Diphenyl dimethicone 400 cSt (US INCI name) sold especially under the name KF-54 by Shin-Etsu.

According to another particular mode, the composition comprises at least, as second non-volatile silicone oil, a phenyl oil of formula (III)

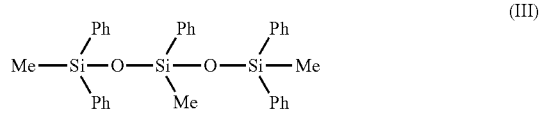

(III)

in which Me represents methyl, Ph represents phenyl.

In this particular case, in order to be in the condition "incompatible", use will be made especially of a content of oil of formula (III) that is greater than or equal to the content of supramolecular compound.

According to one particular mode, the second non-volatile silicone oil is present in the composition in a content ranging from 1% to 40% by weight relative to the total weight of the said composition, in particular from 5% to 30% by weight and especially from 10% to 25% by weight relative to the total weight of the said composition.

According to a particularly preferred embodiment, the composition of the invention comprises at least a combination of a first non-volatile silicone oil of formula (VII)

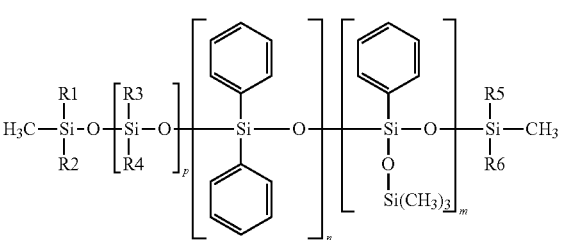

(VII)

in which:

R1 to R6, independently of each other, are saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl, m and n are, independently of each other, integers between 0 and 100, with the proviso that the sum n+m is between 1 and 100;

with p=0 and n=0 and R1, R2, R5 and R6 are identical and are methyl groups; especially such as Phenyl trimethylsiloxy trisiloxane (US INCI name) sold especially under the reference Dow Corning 556 Cosmetic Grade Fluid, and of a second non-volatile silicone oil of formula (VII)

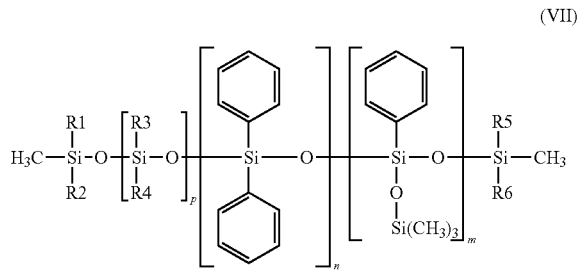

(VII)

in which:
R1 to R6, independently of each other, are saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl, m and n are, independently of each other, integers between 0 and 100, with the proviso that the sum n+m is between 1 and 100;

p≠0 and $R_3$ and $R_4$ are saturated or unsaturated, linear or branched $C_1$-$C_{30}$ and especially $C_1$-$C_{12}$ hydrocarbon-based radicals, and in particular a methyl, ethyl, propyl or butyl radical, preferably methyl, with n=0 and R1 to R6 are identical and are methyl radicals; especially such as Trimethylsiloxyphenyl dimethicone (US INCI name) sold especially under the reference Wacker-Belsil PDM 1000 by Wacker.

This composition also advantageously comprises at least one agent for structuring the liquid fatty phase and in particular an apolar wax, such as a polyethylene wax.

The inventors have moreover observed that the application properties and cosmetic properties of the composition (thickness and homogeneity of the deposit, comfort-absence of tack and absence of drying-out effect) were further improved with optimized ratios of supramolecular compound/silicone oils and first silicone oil/second silicone oil.

Thus, according to one particular mode, the content of first non-volatile silicone oil(s) that are said to be "compatible" with the supramolecular compound is greater than or equal to the content of second non-volatile silicone oil(s) said to be "incompatible" with the supramolecular compound.

In particular, the weight ratio of first non-volatile silicone oil ("compatible")/second non-volatile silicone oil ("incompatible") will range from 2.5/1 to 1/1 and especially from 2/1 to 1/1.

The Applicant has in fact observed that this weight ratio makes it possible to obtain the best compromise of gloss/homogeneity of the makeup result with good remanence.

Advantageously, the total content of first and second non-volatile silicone oils as defined is less than or equal to 75% by weight relative to the total weight of the said composition and in particular less than or equal to 65% by weight relative to the total weight of the said composition. In particular, the total content of first and second non-volatile silicone oils as defined previously will range from 10% to 75% by weight, in particular from 20% to 65% by weight and especially from 40% to 65% by weight relative to the total weight of the said composition.

Viscosity of the Non-Volatile Silicone Oils at 25° C.

The non-volatile silicone oils that may be used in the invention preferably have a viscosity at 25° C. of less than 10 000 cSt and preferably less than or equal to 5000 cSt. The viscosity of these silicone oils may be measured according to standard ASTM D-445.

Advantageously, the two non-volatile silicone oils will have different viscosities, the first non-volatile silicone oil as defined above preferably having a viscosity at 25° C. of less than or equal to 100 cSt and in particular less than or equal to 60 cSt, and the second non-volatile silicone oil as defined above having a viscosity at 25° C. of greater than or equal to 150 cSt, in particular a viscosity ranging from 150 cSt to 10 000 cSt, especially from 200 cSt to 5000 cSt and preferably from 300 to 2000 cSt.

The Applicant has in fact observed that the weight ratio between the oils and the use of a second non-volatile silicone oil of higher viscosity than the first non-volatile silicone oil makes it possible to obtain the best compromise of gloss/homogeneity of the makeup result with good remanence.

Advantageously, a composition according to the invention may comprise from 0.1% to 60% by weight, or even from 1% to 50% or even from 2% to 40% by total weight of silicone oil(s), and especially of phenyl silicone oil(s), relative to the total weight of the composition.

It should be noted that, among the abovementioned silicone oils, phenyl silicone oils prove to be particularly advantageous. These oils make it possible especially to give a good level of gloss to the deposit on the skin or the lips produced with the composition according to the invention, without generating any tack.

Preferably, the composition according to the invention advantageously contains from 1% to 80% by weight, in particular from 5% to 70% by weight and preferably from 10% to 60% by total weight of silicone oils, preferably non-volatile silicone oil, relative to the total weight of the composition.

Preferably, the composition according to the invention contains from 20% to 50% by total weight of silicone oil, preferably of non-volatile silicone oil, relative to the total weight of the composition.

Additional Oil:

According to one embodiment, the composition according to the invention is free of additional oil, different from the said silicone oil.

According to one embodiment, the composition according to the invention may comprise at least one additional oil, different from the said silicone oil.

The additional oil may be chosen from silicone oils that are different from the preceding oils, polar and apolar hydrocarbon-based oils, and mixtures thereof.

Advantageously, the composition of the invention comprises at least one additional polar hydrocarbon-based oil.

Additional Non-Volatile Oil:

According to another embodiment, the additional oil is a non-volatile oil, different from the silicone oil.

The term "non-volatile oil" means an oil that remains on keratin materials, at room temperature and atmospheric pressure, for at least several hours and that especially has a vapour pressure of less than $10^{-3}$ mmHg (0.13 Pa). A non-volatile oil may also be defined as having an evaporation rate such that, under the conditions defined previously, the amount evaporated after 30 minutes is less than 0.07 mg/cm².

Preferably, the additional oil is a hydrocarbon-based oil.

Hydrocarbon-Based Apolar Oils

According to a first embodiment, the oil present in the composition according to the invention is a hydrocarbon-based apolar oil.

These oils may be of plant, mineral or synthetic origin.

For the purposes of the present invention, the term "apolar oil" means an oil whose solubility parameter at 25° C., $\delta_a$, is equal to 0 $(J/cm^3)^{1/2}$.

The definition and calculation of the solubility parameters in the Hansen three-dimensional solubility space are described in the article by C. M. Hansen: "The three dimensional solubility parameters", J. Paint Technol. 39, 105 (1967).

According to this Hansen space:
- $\delta_D$ characterizes the London dispersion forces derived from the formation of dipoles induced during molecular impacts;
- $\delta_p$ characterizes the Debye interaction forces between permanent dipoles and also the Keesom interaction forces between induced dipoles and permanent dipoles;
- $\delta_h$ characterizes the specific interaction forces (such as hydrogen bonding, acid/base, donor/acceptor, etc.); and
- $\delta_a$ is determined by the equation:

$$\delta_a = (\delta_p^2 + \delta_h^2)^{1/2}.$$

The parameters $\delta_p$, $\delta_h$, $\delta_D$ and $\delta_a$ are expressed in $(J/cm^3)^{1/2}$.

The term "hydrocarbon-based oil" means an oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

Preferably, the non-volatile apolar hydrocarbon-based oil is free of oxygen atoms.

Preferably, the non-volatile apolar hydrocarbon-based oil may be chosen from linear or branched hydrocarbons of mineral or synthetic origin, such as:
- liquid paraffin or derivatives thereof,
- squalane,
- isoeicosane,
- liquid petroleum jelly,
- naphthalene oil,
- polybutylenes such as Indopol H-100 (molar mass or MW=965 g/mol), Indopol H-300 (MW=1340 g/mol) and Indopol H-1500 (MW=2160 g/mol) sold or manufactured by the company Amoco,
  - hydrogenated polyisobutylenes such as Parleam® sold by the company Nippon Oil Fats, Panalane H-300 E sold or manufactured by the company Amoco (MW=1340 g/mol), Viseal 20000 sold or manufactured by the company Synteal (MW=6000 g/mol) and Rewopal PIB 1000 sold or manufactured by the company Witco (MW=1000 g/mol),
- decene/butene copolymers, polybutene/polyisobutene copolymers, especially Indopol L-14,
- polydecenes and hydrogenated polydecenes such as: Puresyn 10 (MW=723 g/mol) and Puresyn 150 (MW=9200 g/mol) sold or manufactured by the company Mobil Chemicals,
- and mixtures thereof.

Polar Oils:

According to a second preferred embodiment, the said non-volatile oil is a hydrocarbon-based, silicone or fluoro polar oil.

The term "silicone oil" means an oil containing at least one silicon atom, and especially containing Si—O groups.

The term "fluoro oil" means an oil containing at least one fluorine atom.

According to a first preferred embodiment, the said non-volatile polar oil is a hydrocarbon-based oil.

For the purposes of the present invention, the term "polar oil" means an oil whose solubility parameter at 25° C., $\delta_a$, is other than 0 $(J/cm^3)^{1/2}$.

These oils may be of plant, mineral or synthetic origin.

The term "polar hydrocarbon-based oil" means an oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

In particular, the hydrocarbon-based non-volatile polar oil may be chosen from the list of oils below, and mixtures thereof:
- hydrocarbon-based plant oils such as liquid triglycerides of fatty acids containing from 4 to 10 carbon atoms, for instance heptanoic or octanoic acid triglycerides or jojoba oil;
- hydrocarbon-based esters of formula RCOOR' in which RCOO represents a carboxylic acid residue containing from 2 to 30 carbon atoms, and R' represents a hydrocarbon-based chain containing from 1 to 30 carbon atoms, such as isononyl isononanoate, oleyl erucate or 2-octyldodecyl neopentanoate; isopropyl myristate;
- polyesters obtained by condensation of an unsaturated fatty acid dimer and/or trimer and of diol, such as those described in patent application FR 0 853 634, in particular such as dilinoleic acid and 1,4-butanediol. Mention may especially be made in this respect of the polymer sold by Biosynthis under the name Viscoplast 14436H (INCI name: dilinoleic acid/butanediol copolymer), or else copolymers of polyols and of dimer diacids, and esters thereof, such as Hailuscent ISDA;
- fatty alcohols containing from 12 to 26 carbon atoms, which are preferably branched, for instance octyldodecanol, 2-butyloctanol, 2-hexyldecanol, 2-undecylpentadecanol and oleyl alcohol;
- $C_{12}$-$C_{22}$ higher fatty acids, such as oleic acid, linoleic acid or linolenic acid, and mixtures thereof;
- oils of plant origin, such as sesame oil (820.6 g/mol);
- fatty acids containing from 12 to 26 carbon atoms, for instance oleic acid;
- dialkyl carbonates, the two alkyl chains possibly being identical or different, such as dicaprylyl carbonate sold under the name Cetiol CC® by Cognis; and
- non-volatile oils of high molecular mass, for example between 650 and 10 000 g/mol, for instance:
i) vinylpyrrolidone copolymers such as the vinylpyrrolidone/1-hexadecene copolymer, Antaron V-216 sold or manufactured by the company ISP (MW=7300 g/mol),
ii) esters such as:
  a) linear fatty acid esters with a total carbon number ranging from 35 to 70, for instance pentaerythrityl tetrapelargonate (MW=697.05 g/mol),
  b) hydroxylated esters such as polyglycerol-2 triisostearate (MW=965.58 g/mol),
  c) aromatic esters such as tridecyl trimellitate (MW=757.19 g/mol),
  d) esters of $C_{24}$-$C_{28}$ branched fatty acids or fatty alcohols such as those described in patent application EP-A-0 955 039, and especially triisoarachidyl citrate (MW=1033.76 g/mol), pentaerythrityl tetraisononanoate (MW=697.05 g/mol), glyceryl triisostearate (MW=891.51 g/mol), glyceryl tris(2-decyl)tetradecanoate (MW=1143.98 g/mol), pentaerythrityl tetraisostearate (MW=1202.02 g/mol), polyglyceryl-2 tetraisostearate (MW=1232.04 g/mol) or else pentaerythrityl tetrakis(2-decyl)tetradecanoate (MW=1538.66 g/mol), e) esters and polyesters of a diol dimer and of a monocarboxylic or dicarboxylic acid, such as esters of a diol dimer and of a fatty acid and esters of a diol dimer and of a dicarboxylic acid dimer; mention may be made especially of the esters of dilinoleic diacids and of dilinoleyl diol dimers sold by the company Nippon Fine Chemical under the trade names Lusplan DD-DA5® and DD-DA7®, f) fatty acid esters of C12-C15 alcohols, such as the C12-15 Alkyl benzoate sold especially under the name Tegosoft TN from Evonik Goldschmidt;

and mixtures thereof.

The esters of a diol dimer and of a monocarboxylic acid may be obtained from a monocarboxylic acid containing from 4 to 34 carbon atoms and especially from 10 to 32 carbon atoms, which acids are linear or branched, and saturated or unsaturated.

As illustrative examples of monocarboxylic acids that are suitable for use in the invention, mention may be made especially of fatty acids.

The esters of diol dimer and of dicarboxylic acid may be obtained from a dicarboxylic acid dimer derived in particular from the dimerization of an unsaturated fatty acid especially of $C_8$ to $C_{34}$, especially $C_{12}$ to $C_{22}$, in particular $C_{16}$ to C20 and more particularly $C_{18}$.

According to one particular variant, it is more particularly the dicarboxylic acid dimer from which the diol dimer to be esterified is also derived.

The esters of a diol dimer and of a carboxylic acid may be obtained from a diol dimer produced by catalytic hydrogenation of a dicarboxylic acid dimer as described previously, for example hydrogenated dilinoleic diacid.

Illustrations of esters of a diol dimer that may especially be mentioned include the esters of dilinoleic diacids and of dilinoleyl diol dimers sold by the company Nippon Fine Chemical under the trade names Lusplan DD-DA5® and DD-DA7®.

Preferably, the composition according to the invention comprises at least one non-volatile oil chosen from polar oils. Preferably, the non-volatile oil is chosen from fatty alcohols containing from 12 to 26 carbon atoms, which are preferably monoalcohols, and preferably branched, for instance octyldodecanol, 2-butyloctanol, 2-hexyldecanol, 2-undecylpentadecanol and oleyl alcohol; according to another embodiment, the said additional polar non-volatile oil is a fluoro oil.

According to one particular mode, the composition of the invention comprises, as non-volatile hydrocarbon-based oil, at least one oil chosen from fatty acid esters of C12-C15 alcohols, such as the C12-15 Alkyl benzoate sold especially under the name Tegosoft TN from Evonik Goldschmidt.

Non-Volatile Fluoro Oil

According to a second embodiment, the second non-volatile oil is a fluoro oil.

The term "fluoro oil" means an oil containing at least one fluorine atom.

The fluoro oils that may be used according to the invention may be chosen from fluorosilicone oils, fluoro polyethers and fluorosilicones as described in document EP-A-847 752, and perfluoro compounds.

According to the invention, the term "perfluoro compounds" means compounds in which all the hydrogen atoms have been replaced with fluorine atoms.

According to one particularly preferred embodiment, the fluoro oil according to the invention is chosen from per-fluoro oils.

As examples of perfluoro oils that may be used in the invention, mention may be made of perfluorodecalins and perfluoroperhydrophenanthrenes.

According to one particularly preferred embodiment, the fluoro oil is chosen from perfluoroperhydrophenanthrenes, and especially the Fiflow® products sold by the company Créations Couleurs. In particular, use may be made of the fluoro oil whose INCI name is perfluoroperhydrophenanthrene, sold under the reference Fiflow 220 by the company F2 Chemicals.

Preferably, the composition according to the invention advantageously contains from 1% to 40% by weight and in particular from 3% to 30% by weight of additional non-volatile oil relative to the total weight of the composition.

According to one particular mode, the composition comprises an additional polar hydrocarbon-based oil in a content ranging from 1% to 20% by weight, especially from 5% to 15% by weight and better still from 7% to 12% by weight relative to the total weight of the said composition.

Additional Volatile Oil

According to a second embodiment, the additional oil is a volatile oil, different from the silicone oil.

The term "volatile oil" means an oil (or non-aqueous medium) that can evaporate on contact with the skin in less than one hour, at room temperature and atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.1 to 10 mmHg).

These oils may be silicone oils, hydrocarbon-based oils or fluoro oils, or mixtures thereof.

The additional volatile silicone oil that may be used in the invention may be chosen from silicone oils especially having a viscosity≤8 centistokes (cSt) ($8 \times 10^{-6}$ m$^2$/s).

Furthermore, the volatile silicone oil that may be used in the invention may preferably be chosen from silicone oils with a flash point ranging from 40° C. to 102° C., preferably with a flash point of greater than 55° C. and less than or equal to 95° C., and preferentially less than 80° C.

Volatile silicone oils that may be mentioned include:
volatile linear or cyclic silicone oils, especially those with a viscosity≤8 centistokes (cSt) ($8 \times 10^{-6}$ m$^2$/s), and especially containing from 2 to 10 silicon atoms and in particular from 2 to 7 silicon atoms, these silicones optionally comprising alkyl or alkoxy groups containing from 1 to 10 carbon atoms.

More particularly, the volatile silicone oils are non-cyclic and are chosen in particular from:
the non-cyclic linear silicones of formula (I):

$$R_3SiO\text{—}(R_2SiO)_n\text{—}SiR_3 \qquad (I)$$

in which R, which may be identical or different, denotes:
a saturated or unsaturated hydrocarbon-based radical, containing from 1 to 10 carbon atoms and preferably from 1 to 6 carbon atoms, optionally substituted with one or more fluorine atoms or with one or more hydroxyl groups, or
a hydroxyl group, one of the radicals R possibly being a phenyl group, n is an integer ranging from 0 to 8, preferably ranging from 2 to 6 and better still ranging from 3 to 5, the silicone compound of formula (I) containing not more than 15 carbon atoms, the branched silicones of formula (II) or (III) below:

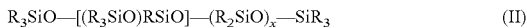  (II)

  (III)

in which R, which may be identical or different, denotes:
- a saturated or unsaturated hydrocarbon-based radical, containing from 1 to 10 carbon atoms, optionally substituted with one or more fluorine atoms or with one or more hydroxyl groups, or
- a hydroxyl group, one of the radicals R possibly being a phenyl group, x is an integer ranging from 0 to 8, the silicone compound of formula (II) or (III) containing not more than carbon atoms.

Preferably, for the compounds of formulae (I), (II) and (III), the ratio between the number of carbon atoms and the number of silicon atoms is between 2.25 and 4.33.

The silicones of formulae (I) to (III) may be prepared according to the known processes for synthesizing silicone compounds.

Among the silicones of formula (I) that may be mentioned are:
- the following disiloxanes: hexamethyldisiloxane (surface tension=15.9 mN/m), sold especially under the name DC 200 Fluid 0. 65 cSt by the company Dow Corning, 1,3-di-tert-butyl-1,1,3,3-tetramethyldisiloxane; 1,3-dipropyl-1,1,3,3-tetramethyldisiloxane; heptylpentamethyldisiloxane; 1,1,1-triethyl-3,3,3-trimethyldisiloxane; hexaethyldisiloxane; 1,1,3,3-tetramethyl-1,3-bis(2-methylpropyl)disiloxane; pentamethyloctyldisiloxane; 1,1,1-trimethyl-3,3,3-tris(1-methylethyl)disiloxane; 1-butyl-3-ethyl-1,1,3-trimethyl-3-propyldisiloxane; pentamethylpentyldisiloxane; 1-butyl-1,1,3,3-tetramethyl-3-(1-methylethyl)disiloxane; 1,1,3,3-tetramethyl-1,3-bis(1-methylpropyl)disiloxane; 1,1,3-triethyl-1,3,3-tripropyldisiloxane; (3,3-dimethylbutyl)pentamethyldisiloxane; (3-methylbutyl)pentamethyldisiloxane; (3-methylpentyl)pentamethyldisiloxane; 1,1,1-triethyl-3,3-dimethyl-3-propyldisiloxane; 1-(1,1-dimethylethyl)-1,1,3,3,3-pentamethyldisiloxane; 1,1,1-trimethyl-3,3,3-tripropyldisiloxane; 1,3-dimethyl-1,1,3,3-tetrakis(1-methylethyl)disiloxane; 1,1-dibutyl-1,3,3,3-tetramethyldisiloxane; 1,1,3,3-tetramethyl-1,3-bis(1-methylethyl)disiloxane; 1,1,1,3-tetramethyl-3,3-bis(1-methylethyl)disiloxane; 1,1,1,3-tetramethyl-3,3-dipropyldisiloxane; 1,1,3,3-tetramethyl-1,3-bis(3-methylbutyl)disiloxane; butylpentamethyldisiloxane; pentaethylmethyldisiloxane; 1,1,3,3-tetramethyl-1,3-dipentyldisiloxane; 1,3-dimethyl-1,1,3,3-tetrapropyldisiloxane; 1,1,1,3-tetraethyl-3,3-dimethyldisiloxane; 1,1,1-triethyl-3,3,3-tripropyldisiloxane; 1,3-dibutyl-1,1,3,3-tetramethyldisiloxane and hexylpentamethyldisiloxane;
- the following trisiloxanes: octamethyltrisiloxane (surface tension=17.4 mN/m), sold especially under the name DC 200 Fluid 1 cSt by the company Dow Corning, 3-pentyl-1,1,1,3,5,5,5-heptamethyltrisiloxane; 1-hexyl-1,1,3,3,5,5,5-heptamethyltrisiloxane; 1,1,1,3,3,5,5-heptamethyl-5-octyltrisiloxane; 1,1,1,3,5,5,5-heptamethyl-3-octyltrisiloxane, sold especially under the name Silsoft 034 by the company OSI; 1,1,1,3,5,5,5-heptamethyl-3-hexyltrisiloxane (surface tension=20.5 mN/m), sold especially under the name DC 2-1731 by the company Dow Corning; 1,1,3,3,5,5-hexamethyl-1,5-dipropyltrisiloxane; 3-(1-ethylbutyl)-1,1,1,3,5,5,5-heptamethyltrisiloxane; 1,1,1,3,5,5,5-heptamethyl-3-(1-methylpentyl)trisiloxane; 1,5-diethyl-1,1,3,3,5,5-hexamethyltrisiloxane; 1,1,1,3,5,5,5-heptamethyl-3-(1-methylpropyl)trisiloxane; 3-(1,1-dimethylethyl)-1,1,1,3,5,5,5-heptamethyltrisiloxane; 1,1,1,5,5,5-hexamethyl-3,3-bis(1-methylethyl)trisiloxane; 1,1,1,3,3,5,5-hexamethyl-1,5-bis(1-methylpropyl)trisiloxane; 1,5-bis(1,1-dimethylethyl)-1,1,3,3,5,5-hexamethyltrisiloxane; 3-(3,3-dimethylbutyl)-1,1,1,3,5,5,5-heptamethyltrisiloxane; 1,1,1,3,5,5,5-heptamethyl-3-(3-methylbutyl)trisiloxane; 1,1,1,3,5,5,5-heptamethyl-3-(3-methylpentyl)trisiloxane; 1,1,1,3,5,5,5-heptamethyl-3-(2-methylpropyl)trisiloxane; 1-butyl-1,1,3,3,5,5,5-heptamethyltrisiloxane; 1,1,1,3,5,5,5-heptamethyl-3-propyltrisiloxane; 3-isohexyl-1,1,1,3,5,5,5-heptamethyltrisiloxane; 1,3,5-triethyl-1,1,3,5,5-pentamethyltrisiloxane; 3-butyl-1,1,1,3,5,5,5-heptamethyltrisiloxane; 3-tert-pentyl-1,1,1,3,5,5,5-heptamethyltrisiloxane; 1,1,1,5,5,5-hexamethyl-3,3-dipropyltrisiloxane; 3,3-diethyl-1,1,1,5,5,5-hexamethyltrisiloxane; 1,5-dibutyl-1,1,3,3,5,5-hexamethyltrisiloxane; 1,1,1,5,5,5-hexaethyl-3,3-dimethyltrisiloxane; 3,3-dibutyl-1,1,1,5,5,5-hexamethyltrisiloxane; 3-ethyl-1,1,1,3,5,5,5-heptamethyltrisiloxane; 3-heptyl-1,1,1,3,5,5,5-heptamethyltrisiloxane and 1-ethyl-1,1,3,3,5,5,5-heptamethyltrisiloxane;
- the following tetrasiloxanes: decamethyltetrasiloxane (surface tension=18 mN/m), sold especially under the name DC 200 Fluid 1.5 cSt by the company Dow Corning; 1,1,3,3,5,5,7,7-octamethyl-1,7-dipropyltetrasiloxane; 1,1,1,3,3,5,7,7,7-nonamethyl-5-(1-methylethyl)tetrasiloxane; 1-butyl-1,1,3,3,5,5,7,7,7-nonamethyltetrasiloxane; 3,5-diethyl-1,1,1,3,5,7,7,7-octamethyltetrasiloxane; 1,3,5,7-tetraethyl-1,1,3,5,7,7-hexamethyltetrasiloxane; 3,3,5,5-tetraethyl-1,1,1,7,7,7-hexamethyltetrasiloxane; 1,1,1,3,3,5,5,7,7-nonamethyl-7-phenyltetrasiloxane; 3,3-diethyl-1,1,1,5,5,7,7,7-octamethyltetrasiloxane; 1,1,1,3,3,5,7,7,7-nonamethyl-5-phenyltetrasiloxane; d)
- the following pentasiloxanes: dodecamethylpentasiloxane (surface tension=18.7 mN/m), sold especially under the name DC 200 Fluid 2 cSt by the company Dow Corning; 1,1,3,3,5,5,7,7,9,9-decamethyl-1,9-dipropylpentasiloxane; 3,3,5,5,7,7-hexaethyl-1,1,1,9,9,9-hexamethylpentasiloxane; 1,1,1,3,3,5,7,7,9,9,9-undecamethyl-5-phenylpentasiloxane; 1-butyl-1,1,3,3,5,5,7,7,9,9,9-undecamethylpentasiloxane; 3,3-diethyl-1,1,1,5,5,7,7,9,9,9-decamethylpentasiloxane; 1,3,5,7,9-pentaethyl-1,1,3,5,7,9,9-heptamethylpentasiloxane; 3,5,7-triethyl-1,1,1,3,5,7,9,9,9-nonamethylpentasiloxane and 1,1,1-triethyl-3,3,5,5,7,7,9,9,9-nonamethylpentasiloxane;
- the following hexasiloxanes: 1-butyl-1,1,3,3,5,5,7,7,9,9,11,11,11-tridecamethylhexasiloxane; 3,5,7,9-tetraethyl-1,1,1,3,5,7,9,11,11,11-decamethylhexasiloxane and tetradecamethylhexasiloxane;
- hexadecamethylheptasiloxane;
- octadecamethyloctasiloxane;
- eicosamethylnonasiloxane.

Among the silicones of formula (II) that may be mentioned are:
- the following tetrasiloxanes: 2-[3,3,3-trimethyl-1,1-bis[(trimethylsilyl)oxy]disiloxanyl]ethyl; 1,1,1,5,5,5-hexamethyl-3-(2-methylpropyl)-3-[(trimethylsilyl)oxy]trisiloxane; 3-(1,1-dimethylethyl)-1,1,1,5,5,5-hexamethyl-3-[(trimethylsilyl)oxy]trisiloxane; 3-butyl- 1,1,1,5,5,5-hexamethyl-3-[(trimethylsilyl)oxy] trisiloxane; 1,1,1,5,5,5-hexamethyl-3-propyl-3-[(trimethylsilyl)oxy]trisiloxane; 3-ethyl-1,1,1,5,5,5-hexamethyl-3-[(trimethylsilyl)oxy]trisiloxane; 1,1,1-triethyl-3,5,5,5-tetramethyl-3-(trimethylsiloxy) trisiloxane; 3-methyl-, 1,1,5,5,5-hexamethyl-3-[trimethylsilyl)oxy]trisiloxane; 3-[(dimethylphenylsilyl)oxy]-1,1,3,5,5,5-heptamethyl-trisiloxane; 1,1,1,5,5,5-hexamethyl-3-(2-methylpentyl)-3-[(trimethylsilyl)oxy]trisiloxane; 1,1,1,5,5,5-hexamethyl-3-(4-methylpentyl)-3-[(trimethylsilyl)oxy] trisiloxane; 3-hexyl-1,1,1,5,5,5-hexamethyl-3-[(trimethylsilyl)oxy]trisiloxane and 1,1,1,3,5,5,5-heptamethyl-3-[(trimethylsilyl)oxy]trisiloxane;

the following pentasiloxanes: 1,1,1,3,5,5,7,7,7-nonamethyl-3-(trimethylsiloxy)tetrasiloxane and 1,1,1,3,3,7,7-octamethyl-5-phenyl-5-[(trimethylsilyl)oxy] tetrasiloxane;

the following hexasiloxane: 1,1,1,3,5,5,7,7,9,9,11,11,11-tridecamethyl-3-[(trimethylsilyl)oxy]hexasiloxane.

Among the silicones of formula (III), mention may be made of:

1,1,1,5,5,5-hexamethyl-3,3-bis(trimethylsiloxy)trisiloxane.

Use may also be made of other volatile silicone oils chosen from:

the following tetrasiloxanes: 2,2,8,8-tetramethyl-5-[(pentamethyldisiloxanyl)methyl]-3,7-dioxa-2,8-disilanonane; 2,2,5,8,8-pentamethyl-5-[(trimethylsilyl)methoxy]-4,6-dioxa-2,5,8-trisilanonane; 1,3-dimethyl-1,3-bis[(trimethylsilyl)methyl]-1,3-disiloxanediol; 3-ethyl-1,1,1,5,5,5-hexamethyl-3-[3-(trimethylsiloxy)propyl]trisiloxane and 1,1,1,5,5,5-hexamethyl-3-phenyl-3-[(trimethylsilyl)oxy]trisiloxane (Dow 556 Fluid);

the following pentasiloxanes: 2,2,7,7,9,9,11,11,16,16-decamethyl-3,8,10,15-tetraoxa-2,7,9,11,16-pentasilaheptadecane and the tetrakis[(trimethylsilyl)methyl]ester of silicic acid;

the following hexasiloxanes: 3,5-diethyl-1,1,1,7,7,7-hexamethyl-3,5-bis[(trimethylsilyl)oxy]tetrasiloxane and 1,1,1,3,5,7,7,7-octamethyl-3,5-bis[(trimethylsilyl)oxy] tetrasiloxane;

the heptasiloxane: 1,1,1,3,7,7,7-heptamethyl-3,5,5-tris [(trimethylsilyl)oxy]tetrasiloxane;

the following octasiloxanes: 1,1,1,3,5,5,9,9,9-nonamethyl-3,7,7-tris[(trimethylsilyl)oxy]pentasiloxane; 1,1,1,3,5,7,9,9,9-nonamethyl-3,5,7-tris[(trimethylsilyl) oxy]pentasiloxane and 1,1,1,7,7,7-hexamethyl-3,3,5,5-tetrakis[(trimethylsilyl)oxy]tetrasiloxane.

Volatile silicone oils that may more particularly be mentioned include decamethylcyclopentasiloxane sold especially under the name DC-245 by the company Dow Corning, dodecamethylcyclohexasiloxane sold especially under the name DC-246 by the company Dow Corning, octamethyltrisiloxane sold especially under the name DC-200 Fluid 1 cSt by the company Dow Corning, decamethyltetrasiloxane sold especially under the name DC-200 Fluid 1.5 cSt by the company Dow Corning and DC-200 Fluid 5 cSt sold by the company Dow Corning, octamethylcyclotetrasiloxane, heptamethylhexyltrisiloxane, heptamethylethyltrisiloxane, heptamethyloctyltrisiloxane and dodecamethylpentasiloxane, and mixtures thereof.

In particular, volatile oils that may be mentioned include volatile hydrocarbon-based oils and especially apolar volatile hydrocarbon-based oils (the flash point is in particular measured according to ISO Standard 3679), such as hydrocarbon-based oils containing from 8 to 16 carbon atoms, and especially:

branched $C_8$-$C_{16}$ alkanes, for instance $C_8$-$C_{14}$ isoalkanes of petroleum origin (also known as isoparaffins), for instance isododecane (also known as 2,2,4,4,6-pentamethylheptane), isohexadecane and isodecane, and, for example, the oils sold under the trade name Isopar or Permethyl, linear alkanes, for example such as n-dodecane (C12) and n-tetradecane (C14) sold by Sasol under the references, respectively, Parafol 12-97 and Parafol 14-97, and also mixtures thereof, the undecane-tridecane mixture (Cetiol UT), mixtures of n-undecane (C11) and of n-tridecane (C13) obtained in Examples 1 and 2 of patent application WO 2008/155 059 from the company Cognis, and mixtures thereof.

The volatile solvent is preferably chosen from volatile hydrocarbon-based oils containing from 8 to 14 carbon atoms, and mixtures thereof.

As other volatile hydrocarbon-based oils, and especially as volatile polar hydrocarbon-based oils, mention may also be made of ketones that are liquid at room temperature, such as methyl ethyl ketone or acetone; short-chain esters (containing from 3 to 8 carbon atoms in total) such as ethyl acetate, methyl acetate, propyl acetate or n-butyl acetate; ethers that are liquid at room temperature, such as diethyl ether, dimethyl ether or dichlorodiethyl ether; alcohols and especially linear or branched lower monoalcohols containing from 2 to 5 carbon atoms, such as ethanol, isopropanol or n-propanol.

Preferably, the composition comprises at least one additional non-silicone volatile oil.

Preferably, the said additional oil is a volatile hydrocarbon-based oil. Preferably, it is isododecane.

Preferably, the composition according to the invention contains from 1% to 50% by weight and in particular from 3% to 40% by weight of additional volatile oil relative to the total weight of the composition.

Solid Fatty Substances

Besides the oils described previously, the composition according to the invention may comprise at least one agent for structuring the fatty phase, in particular at least one fatty substance that is not liquid at room temperature (25° C.) and at atmospheric pressure, known as a solid fatty substance, chosen especially from waxes and pasty fatty substances, and mixtures thereof.

According to one mode, the composition of the invention comprises at least one wax.

Preferably, the composition of the invention comprises at least one apolar wax.

According to one particular mode, the invention relates to a cosmetic composition, preferably for making up and/or caring for keratin materials, especially the skin or the lips, in particular the lips, comprising, in a cosmetically acceptable medium, at least:

(a) a compound A (referred to, in the context of the present patent application, as a supramolecular compound) that may be obtained by reaction between:

at least one oil bearing at least one nucleophilic reactive function chosen from OH and $NH_2$, and at least one junction group capable of establishing hydrogen bonds with one or more partner junction groups, each pairing of a junction group involving at least three hydrogen bonds, the said junction group bearing at least one isocyanate or imidazole reactive function capable of reacting with the reactive function borne by the oil, the said junction group also comprising at least one unit of formula (I) or (II):

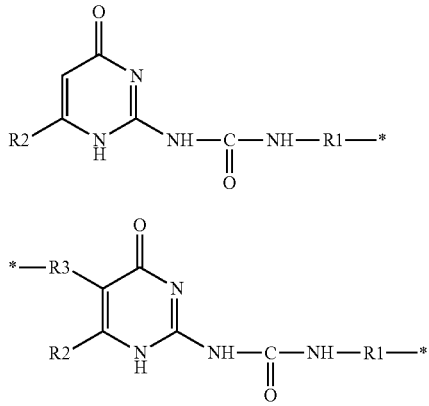

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;
R2 represents a hydrogen atom or a linear, branched or cyclic, saturated or unsaturated, optionally aromatic, C1-C32 carbon-based and especially hydrocarbon-based radical, which may comprise one or more heteroatoms chosen from O, N, S, F, Si and P;

(b) at least two distinct non-volatile silicone oils chosen from:
i) phenyl silicone oils of formula (II), (VII) or (X) below:

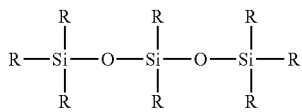

in which the groups R represent, independently of each other, saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl, or a phenyl, at least one of the groups R being a phenyl group,

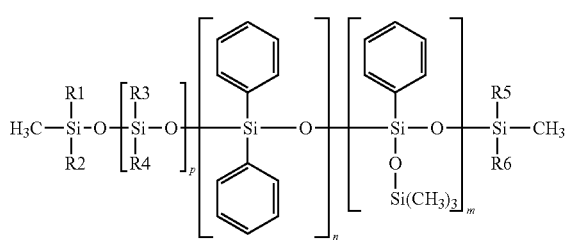

in which:
R1 to R6, independently of each other, are saturated or unsaturated, linear, cyclic or branched $C_1$-$C_{30}$ and especially $C_1$-$C_{12}$ hydrocarbon-based radicals, and in particular a methyl, ethyl, propyl or butyl radical, preferably methyl,
m, n and p are, independently of each other, integers between 0 and 100, with the proviso that the sum n+m is between 1 and 100;
ii) linear or cyclic polydimethylsiloxanes (PDMSs),
iii) polydimethylsiloxanes comprising alkyl or alkoxy groups, which are pendent and/or at the end of the silicone chain, these groups each containing from 2 to 24 carbon atoms,
it being understood that:
at least one of the non-volatile silicone oils is chosen from the phenyl silicone oils of formula (II) or of formula (VII) with p=0 (also known as oil that is "compatible" with the supramolecular compound in the description) and
at least one of the said non-volatile silicone oils is chosen from the phenyl silicone oils of formula (VII) with p≠0 and $R_3$ and $R_4$ are saturated or unsaturated, linear or branched $C_1$-$C_{30}$ and especially $C_1$-$C_{12}$ hydrocarbon-based radicals, and in particular a methyl, ethyl, propyl or butyl radical, preferably methyl, linear or cyclic polydimethylsiloxanes (PDMSs), and polydimethylsiloxanes comprising alkyl or alkoxy groups, which are pendent and/or at the end of the silicone chain, these groups each containing from 2 to 24 carbon atoms (also known as oil that is "incompatible" with the supramolecular compound in the description),
and
(d) at least one agent for structuring the liquid fatty phase, chosen especially from waxes and/or pasty fatty substances, in particular waxes, in a content ranging from 1% to 20% by weight, in particular from 1% to 15% by weight and better still from 1% to 10% by weight relative to the total weight of the said composition.

Waxes

For the purposes of the present invention, the term "wax" means a lipophilic compound, which is solid at room temperature (25° C.), with a reversible solid/liquid change of state, which has a melting point of greater than or equal to 30° C., which may be up to 200° C. and especially up to 120° C.

In particular, the waxes that are suitable for use in the invention may have a melting point of greater than or equal to 45° C. and in particular greater than or equal to 55° C.

For the purposes of the invention, the melting point corresponds to the temperature of the most endothermic peak observed on thermal analysis (DSC) as described in standard ISO 11357-3; 1999.

The melting point of the wax may be measured using a differential scanning calorimeter (DSC), for example the calorimeter sold under the name DSC 30 by the company Mettler, or in particular the calorimeter sold under the name DSC Q2000 by the company TA Instruments.

Preferably, the waxes have a heat of fusion ΔHf of greater than or equal to 70 J/g.

Preferably, the waxes comprise at least one crystallizable part, which is visible by X-ray observation.

Preferably, the measuring protocol is as follows:
A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature increase ranging from −20° C. to 100° C. at a heating rate of 5° C./minute. During the second temperature increase, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The wax may especially have a hardness ranging from 0.05 MPa to 15 MPa and preferably ranging from 6 MPa to 15 MPa. The hardness is determined by measuring the compressive force, measured at 20° C. using the texture analyser sold under the name TA-TX2i by the company Rheo, equipped with a stainless-steel cylinder with a diameter of 2 mm, travelling at a measuring speed of 0.1 mm/second, and penetrating the wax to a penetration depth of 0.3 mm.

According to another preferred measuring protocol:

A sample of 5 mg of wax placed in a crucible is subjected to a first temperature rise ranging from −20° C. to 120° C., at a heating rate of 10° C./minute, it is then cooled from 120° C. to −20° C. at a cooling rate of 10° C./minute and is finally subjected to a second temperature rise ranging from −20° C. to 120° C. at a heating rate of 5° C./minute.

During the second temperature rise, the following parameters are measured:
the melting point ($T_f$) of the wax, as mentioned previously corresponding to the temperature of the most endothermic peak of the melting curve observed, representing the variation of the difference in power absorbed as a function of the temperature,
ΔHf: the heat of fusion of the wax, corresponding to the integral entire melting curve obtained. This heat of fusion of the wax is the amount of energy required to make the compound change from the solid state to the liquid state. It is expressed in J/g.

The waxes that may be used in the compositions according to the invention are chosen from waxes that are solid at room temperature of animal, plant, mineral or synthetic origin, and mixtures thereof.

The waxes may be hydrocarbon-based waxes, silicone waxes or fluoro waxes, and may be of plant, mineral, animal and/or synthetic origin. In particular, the waxes have a melting point of greater than 25° C. and better still greater than 45° C.

Preferably, the composition according to the invention comprises a wax content of between 1% and 40% by weight, relative to the total weight of the composition, preferably between 3% and 30% by weight, better still from 5% to 20% and even better still from 7% to 15% by weight relative to the total weight of the composition.

Advantageously, the composition according to the invention comprises a wax content of between 1% and 20% by weight, relative to the total weight of the composition, preferably between 3% and 15% by weight and better still from 5% to 10% by weight relative to the total weight of the composition.

Apolar Waxes:

Preferably, the composition according to the invention comprises at least one apolar wax.

For the purposes of the present invention, the term "apolar wax" means a wax whose solubility parameter at 25° C. as defined below, $\delta_a$, is equal to 0 $(J/cm^3)^{1/2}$.

Apolar waxes are in particular hydrocarbon-based waxes constituted solely of carbon and hydrogen atoms, and free of heteroatoms such as N, O, Si and P.

In particular, the expression "apolar wax" is understood to mean a wax that is constituted solely of apolar wax, rather than a mixture also comprising other types of waxes that are not apolar waxes.

As illustrations of apolar waxes that are suitable for use in the invention, mention may be made especially of hydrocarbon-based waxes, for instance microcrystalline waxes, paraffin waxes, ozokerite and polyethylene waxes.

Preferably, the composition according to the invention comprises at least one apolar hydrocarbon-based wax chosen from microcrystalline waxes, paraffin waxes, ozokerite and polyethylene waxes.

Polyethylene waxes that may be mentioned include Performalene 500-L Polyethylene and Performalene 400 Polyethylene sold by New Phase Technologies.

An ozokerite that may be mentioned is Ozokerite Wax SP 1020 P from Strahl & Pitsch.

As microcrystalline waxes that may be used, mention may be made of Multiwax W 445® sold by the company Sonneborn, and Microwax HW® and Base Wax 30540® sold by the company Paramelt.

As microwaxes that may be used in the compositions according to the invention as apolar wax, mention may be made especially of polyethylene microwaxes such as those sold under the names Micropoly 200®, 220®, 220L® and 250S® by the company Micro Powders.

Preferably, the composition according to the invention comprises at least one apolar wax chosen from microcrystalline waxes, polyethylene waxes and ozokerite waxes.

According to one particular mode, the composition of the invention comprises at least one apolar wax chosen from polyethylene waxes (Performalene 500L polyethylene from New Phase Technologies), microcrystalline waxes (Microwax HW from Paramelt) and alkane waxes (Ozokerite Wax SP 1020 P from Strahl & Pitsch).

The composition according to the invention may comprise a content of apolar waxes ranging from 0.1% to 30% by weight relative to the total weight of the composition; it may in particular contain from 0.5% to 20% and more particularly from 1% to 15% thereof.

Advantageously, the composition according to the invention comprises an apolar wax content of between 1% and 20% by weight, relative to the total weight of the composition, preferably between 3% and 15% by weight and better still from 5% to 10% by weight relative to the total weight of the composition.

Polar Wax

According to one embodiment, the composition according to the invention may comprise at least one polar wax.

For the purposes of the present invention, the term "polar wax" means a wax whose solubility parameter at 25° C., $\delta_a$, is other than 0 $(J/cm^3)^{1/2}$.

In particular, the term "polar wax" means a wax whose chemical structure is formed essentially from, or even constituted of, carbon and hydrogen atoms, and comprising at least one highly electronegative heteroatom such as an oxygen, nitrogen, silicon or phosphorus atom.

The definition and calculation of the solubility parameters in the Hansen three-dimensional solubility space are described in the article by C. M. Hansen: "The three dimensional solubility parameters", J. Paint Technol. 39, 105 (1967).

According to this Hansen space:
- $\delta_D$ characterizes the London dispersion forces derived from the formation of dipoles induced during molecular impacts;
- $\delta_p$ characterizes the Debye interaction forces between permanent dipoles and also the Keesom interaction forces between induced dipoles and permanent dipoles;
- $\delta_h$ characterizes the specific interaction forces (such as hydrogen bonding, acid/base, donor/acceptor, etc.); and
- $\delta_a$ is determined by the equation:

$$\delta_a = (\delta_p^2 + \delta_h^2)^{1/2}.$$

The parameters $\delta_p$, $\delta_h$, $\delta_D$ and $\delta_a$ are expressed in $(J/cm^3)^{1/2}$.

The polar waxes may especially be hydrocarbon-based, fluoro or silicone waxes.

The term "silicone wax" means a wax comprising at least one silicon atom, especially comprising Si—O groups.

The term "hydrocarbon-based wax" means a wax formed essentially from, or even constituted of, carbon and hydrogen atoms, and optionally oxygen and nitrogen atoms, and that does not contain any silicon or fluorine atoms. It may contain alcohol, ester, ether, carboxylic acid, amine and/or amide groups.

According to a first preferred embodiment, the polar wax is a hydrocarbon-based wax. As a hydrocarbon-based polar wax, a wax chosen from ester waxes and alcohol waxes is in particular preferred.

The expression "ester wax" is understood according to the invention to mean a wax comprising at least one ester function. According to the invention, the term "alcohol wax" means a wax comprising at least one alcohol function, i.e. comprising at least one free hydroxyl (OH) group.

The following may especially be used as ester wax:
ester waxes such as those chosen from:
i) waxes of formula $R_1COOR_2$ in which $R_1$ and $R_2$ represent linear, branched or cyclic aliphatic chains, the number of atoms of which varies from 10 to 50, which may contain a heteroatom such as O, N or P and the melting point of which varies from 25° C. to 120° C. In particular, use may be made, as an ester wax, of a $C_{20}$-$C_{40}$ alkyl(hydroxystearyloxy) stearate (the alkyl group comprising from 20 to 40 carbon atoms), alone or as a mixture, or a $C_{20}$-$C_{40}$ alkyl stearate. Such waxes are especially sold under the names Kester Wax K 82 P®, Hydroxypolyester K 82 P®, Kester Wax K 80 P® and Kester Wax K82H by the company Koster Keunen.

Use may also be made of a glycol and butylene glycol montanate (octacosanoate) such as the wax Licowax KPS Flakes (INCI name: glycol montanate) sold by the company Clariant.

ii) bis(1,1,1-trimethylolpropane)tetrastearate, sold under the name Hest 2T-4S® by the company Heterene, iii) diester waxes of a dicarboxylic acid of general formula $R^3$—(—OCO—$R^4$—COO—$R^5$), in which $R^3$ and $R^5$ are identical or different, preferably identical, and represent a $C_4$-$C_{30}$ alkyl group (alkyl group comprising from 4 to 30 carbon atoms) and $R^4$ represents a linear or branched $C_4$-$C_{30}$ aliphatic group (alkyl group comprising from 4 to 30 carbon atoms) which may or may not contain one or more unsaturated groups, and preferably that is linear and unsaturated, iv) mention may also be made of the waxes obtained by catalytic hydrogenation of animal or plant oils having linear or branched $C_8$-$C_{32}$ fatty chains, for example such as hydrogenated jojoba oil, hydrogenated sunflower oil, hydrogenated castor oil, hydrogenated coconut oil, and also the waxes obtained by hydrogenation of castor oil esterified with cetyl alcohol, such as those sold under the names Phytowax ricin 16L64® and 22L73® by the company Sophim. Such waxes are described in patent application FR-A-2 792 190 and the waxes obtained by hydrogenation of olive oil esterified with stearyl alcohol such as that sold under the name Phytowax Olive 18 L 57, or else;

v) beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumach wax; montan wax, orange wax, laurel wax and hydrogenated jojoba wax.

According to another embodiment, the polar wax may be an alcohol wax. The expression "alcohol wax" is understood according to the invention to mean a wax comprising at least one alcohol function, i.e. comprising at least one free hydroxyl (OH) group.

Alcohol waxes that may be mentioned include for example the wax Performacol 550-L Alcohol from New Phase Technologies, stearyl alcohol and cetyl alcohol.

According to a second embodiment, the polar wax may be a silicone wax such as siliconized beeswax, or an alkyl dimethicone such as the $C_{30}$-$C_{45}$ alkyl dimethicone sold under the reference SF1642 by Momentive Performance Materials.

According to one particular embodiment, the composition according to the invention comprises at least one apolar wax (preferably a hydrocarbon-based wax) and a polar wax (preferably a silicone wax).

Preferably, the composition according to the invention comprises a content of polar wax ranging from 1% to 40% by weight of wax relative to the total weight of the composition, better still from 1% to 30% by weight and in particular from 5% to 20% by weight relative to the total weight of the composition.

According to one particular mode, the composition does not comprise any polar wax.

Pasty Fatty Substances

The composition according to the invention may comprise, besides the wax(es) at least one additional solid fatty substance, preferably chosen from pasty fatty substances.

For the purposes of the present invention, the term "pasty fatty substance" means a lipophilic fatty compound with a reversible solid/liquid change of state, comprising at a temperature of 23° C. a liquid fraction and a solid fraction.

In other words, the starting melting point of the pasty compound can be less than 23° C. The liquid fraction of the pasty compound measured at 23° C. can represent 9% to 97% by weight of the compound. This liquid fraction at 23° C. preferably represents between 15% and 85% and more preferably between 40% and 85% by weight.

Preferably, the pasty fatty substances have an end melting point of less than 60° C.

Preferably, the pasty fatty substances have a hardness of less than or equal to 6 MPa.

Preferably, the pasty fatty substances have, in the solid state, an anisotropic crystal organization, which is visible by X-ray observation.

For the purposes of the invention, the melting point corresponds to the temperature of the most endothermic peak observed on thermal analysis (DSC) as described in standard ISO 11357-3; 1999. The melting point of a pasty substance or of a wax may be measured using a differential scanning calorimeter (DSC), for example the calorimeter sold under the name DSC Q2000 by the company TA Instruments.

As regards the measurement of the melting point and the determination of the end melting point, the sample preparation and measurement protocols are as follows:

A sample of 5 mg of pasty fatty substance, preheated to 80° C. and withdrawn with magnetic stirring using a spatula that is also heated, is placed in a hermetic aluminium capsule, or a crucible. Two tests are performed to ensure the reproducibility of the results.

The measurements are performed on the abovementioned calorimeter. The oven is flushed with nitrogen. Cooling is performed by an RCS 90 heat exchanger. The sample is then subjected to the following protocol: it is first placed at a temperature of 20° C., and then subjected to a first temperature rise passing from 20° C. to 80° C., at a heating rate of 5° C./minute, then is cooled from 80° C. to −80° C. at a cooling rate of 5° C./minute and finally subjected to a second temperature rise passing from −80° C. to 80° C. at a heating rate of 5° C./minute. During the second temperature rise, the variation in the difference between the power absorbed by the empty crucible and the crucible containing the sample of paste or wax as a function of the temperature is measured. The melting point of the compound is the temperature value corresponding to the top of the peak of the curve representing the variation in the difference in power absorbed as a function of the temperature.

The end melting point corresponds to the temperature at which 95% of the sample has melted.

The liquid fraction by weight of the pasty compound at 23° C. is equal to the ratio of the heat of fusion consumed at 23° C. to the heat of fusion of the pasty compound.

The heat of fusion of the pasty compound is the heat consumed by the compound in order to pass from the solid state to the liquid state. The pasty compound is said to be in the solid state when all of its mass is in crystalline solid form. The pasty compound is said to be in the liquid state when all of its mass is in liquid form.

The heat of fusion of the pasty compound is equal to the integral of the entire melting curve obtained using the abovementioned colorimeter, with a temperature rise of 5 or 10° C./minute, according to standard ISO 11357-3:1999. The heat of fusion of the pasty compound is the amount of energy required to make the compound change from the solid state to the liquid state. It is expressed in J/g.

The heat of fusion consumed at 23° C. is the amount of energy absorbed by the sample to change from the solid state to the state that it has at 23° C., constituted of a liquid fraction and a solid fraction.

The liquid fraction of the pasty compound measured at 32° C. preferably represents from 30% to 100% by weight of the compound, preferably from 50% to 100%, more preferably from 60% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound.

The heat of fusion consumed at 32° C. is calculated in the same way as the heat of fusion consumed at 23° C.

As regards the measurement of the hardness, the sample preparation and measurement protocols are as follows:

The pasty fatty substance is placed in a mould 75 mm in diameter, which is filled to about 75% of its height. In order to overcome the thermal history and to control the crystallization, the mould is placed in a Vötsch VC 0018 programmable oven, where it is first placed at a temperature of 80° C. for 60 minutes, then cooled from 80° C. to 0° C. at a cooling rate of 5° C./minute, and then left at the stabilized temperature of 0° C. for 60 minutes, and then subjected to a temperature rise ranging from 0° C. to 20° C. at a heating rate of 5° C./minute, and then left at the stabilized temperature of 20° C. for 180 minutes.

The compression force measurement is taken using a TA/TX2i texturometer from Swantech. The spindle used is chosen according to the texture:
- cylindrical steel spindle 2 mm in diameter for very rigid starting materials;
- cylindrical steel spindle 12 mm in diameter for sparingly rigid starting materials.

The measurement comprises three steps: a first step after automatic detection of the surface of the sample, where the spindle moves at a measuring speed of 0.1 mm/s, and penetrates into the pasty fatty substance to a penetration depth of 0.3 mm, the software notes the maximum force value reached; a second "relaxation" step where the spindle remains at this position for one second and the force is noted after 1 second of relaxation; finally, a third "withdrawal" step in which the spindle returns to its initial position at a speed of 1 mm/s, and the probe withdrawal energy (negative force) is noted.

The hardness value measured during the first step corresponds to the maximum compression force measured in newtons divided by the area of the texturometer cylinder expressed in $mm^2$ in contact with the pasty fatty substance. The hardness value obtained is expressed in megapascals or MPa.

The pasty compound is preferably chosen from synthetic compounds and compounds of plant origin. A pasty compound may be obtained by synthesis from starting materials of plant origin.

The pasty compound is advantageously chosen from:
- lanolin and its derivatives,
- polyol ethers chosen from ethers of pentaerythritol and of polyalkylene glycol, ethers of fatty alcohol and of sugar, and mixtures thereof, the ethers of pentaerythritol and of polyethylene glycol comprising 5 oxyethylene units (5 OE) (CTFA name: PEG-5 Pentaerythrityl Ether), polypropylene glycol pentaerythrityl ether comprising five oxypropylene (5 OP) units (CTFA name: PPG-5 Pentaerythrityl Ether) and mixtures thereof, and more especially the mixture PEG-5 Pentaerythrityl Ether, PPG-5 Pentaerythrityl Ether and soybean oil, sold under the name Lanolide by the company Vevy, which is a mixture in which the constituents are in a 46/46/8 weight ratio: 46% PEG-5 Pentaerythrityl Ether, 46% PPG-5 Pentaerythrityl Ether and 8% soybean oil;
- polymeric or non-polymeric silicone compounds
- polymeric or non-polymeric fluoro compounds
- vinyl polymers, especially:
    - olefin homopolymers and copolymers,
    - hydrogenated diene homopolymers and copolymers,
    - linear or branched oligomers, homopolymers or copolymers of alkyl(meth)acrylates preferably containing a $C_8$-$C_{30}$ alkyl group,
    - oligomers, homopolymers and copolymers of vinyl esters containing $C_8$-$C_{30}$ alkyl groups,
    - oligomers, homopolymers and copolymers of vinyl ethers containing $C_8$-$C_{30}$ alkyl groups,
- liposoluble polyethers resulting from the polyetherification between one or more $C_2$-$C_{100}$ and preferably $C_2$-$C_{50}$ diols,
- esters,
- and/or mixtures thereof.

The pasty compound is preferably a polymer, especially a hydrocarbon-based polymer.

Among the liposoluble polyethers that are particularly preferred are copolymers of ethylene oxide and/or of propylene oxide with $C_6$-$C_{30}$ long-chain alkylene oxides, more preferably such that the weight ratio of the ethylene oxide and/or of the propylene oxide to the alkylene oxides in the copolymer is from 5:95 to 70:30. In this family, mention will be made especially of copolymers such that the long-chain alkylene oxides are arranged in blocks having an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by Akzo Nobel.

Among the esters, the following are especially preferred:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially such as those sold under the brand name Softisan 649 by the company Sasol,
the arachidyl propionate sold under the brand name Waxenol 801 by Alzo,
phytosterol esters,
fatty acid triglycerides and derivatives thereof, for instance triglycerides of fatty acids, which are especially $C_{10}$-$C_{18}$, and partially or totally hydrogenated such as those sold under the reference Softisan 100 by the company Sasol,
pentaerythritol esters,
non-crosslinked polyesters resulting from polycondensation between a linear or branched C4-C50 dicarboxylic acid or polycarboxylic acid and a C2-C50 diol or polyol, aliphatic esters of an ester resulting from the esterification of an aliphatic hydroxycarboxylic acid ester with an aliphatic carboxylic acid. Preferably, the aliphatic carboxylic acid comprises from 4 to 30 and preferably from 8 to 30 carbon atoms. It is preferably chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof. The aliphatic carboxylic acid is preferably branched. The aliphatic hydroxycarboxylic acid ester is advantageously derived from a hydroxylated aliphatic carboxylic acid containing from 2 to 40 carbon atoms, preferably from 10 to 34 carbon atoms and better still from 12 to 28 carbon atoms, and from 1 to 20 hydroxyl groups, preferably from 1 to 10 hydroxyl groups and better still from 1 to 6 hydroxyl groups. The aliphatic hydroxycarboxylic acid ester is chosen from:
a) partial or total esters of saturated linear mono-hydroxylated aliphatic monocarboxylic acids;
b) partial or total esters of saturated polyhydroxylated aliphatic polycarboxylic acids;
c) partial or total esters of $C_2$ to $C_{16}$ aliphatic polyols that have reacted with a monohydroxylated or polyhydroxylated aliphatic monocarboxylic or polycarboxylic acid,
esters of a diol dimer and of a diacid dimer, where appropriate esterified on their free alcohol or acid function(s) with acid or alcohol radicals, especially dimer dilinoleate esters; such esters may be chosen especially from the esters having the following INCI nomenclature: bis-behenyl/isostearyl/phytosteryl dimer dilinoleyl dimer dilinoleate (Plandool G), phytosteryl/isostearyl/cetyl/stearyl/behenyl dimer dilinoleate (Plandool H or Plandool S), and mixtures thereof,
hydrogenated rosinate esters, such as dilinoleyl dimers of hydrogenated rosinate (Lusplan DD-DHR or DD-DHR from Nippon Fine Chemical);
and mixtures thereof.

Advantageously, the pasty compound(s) preferably represent 0.1% to 80%, better still 0.5% to 60%, better still 1% to 30% and even better still 1% to 20% by weight relative to the total weight of the composition.

According to one particular mode, the composition does not comprise any additional pasty fatty substance.

Additional Film-Forming Polymer

Besides the copolymer described previously, the composition may comprise an additional polymer such as a film-forming polymer.

According to the present invention, the term "film-forming polymer" means a polymer that is capable of forming, by itself or in the presence of an auxiliary film-forming agent, a continuous deposit on a support, especially on keratin materials.

Among the film-forming polymers that may be used in the composition of the present invention, mention may be made of synthetic polymers, of free-radical type or of polycondensate type, polymers of natural origin, and mixtures thereof. Film-forming polymers that may be mentioned in particular include acrylic polymers, polyurethanes, polyesters, polyamides, polyureas and cellulose-based polymers, for instance nitrocellulose.

The polymer may be combined with one or more auxiliary film-forming agents. Such a film-forming agent may be chosen from any compound known to those skilled in the art as being capable of fulfilling the desired function, and may be chosen especially from plasticizers and coalescers.

Silicone Resins

According to one advantageous embodiment, the composition comprises at least one silicone resin.

The presence of a silicone resin especially makes it possible, in particular in makeup compositions in particular for the skin or the lips, to obtain a deposit that shows good colour remanence.

More generally, the term "resin" means a compound whose structure is three-dimensional. "Silicone resins" are also referred to as "siloxane resins". Thus, for the purposes of the present invention, a polydimethylsiloxane is not a silicone resin.

The nomenclature of silicone resins (also known as siloxane resins) is known under the name "MDTQ", the resin being described as a function of the various siloxane monomer units it comprises, each of the letters "MDTQ" characterizing a type of unit.

The letter M represents the monofunctional unit of formula $R1R2R3SiO_{1/2}$, the silicon atom being bonded to only one oxygen atom in the polymer comprising this unit.

The letter D means a difunctional unit $R1R2SiO_{2/2}$ in which the silicon atom is bonded to two oxygen atoms.

The letter T represents a trifunctional unit of formula $R1SiO_{3/2}$.

Such resins are described, for example, in the *Encyclopedia of Polymer Science and Engineering*, vol. 15, John Wiley & Sons, New York, (1989), pp. 265-270, and U.S. Pat. Nos. 2,676,182, 3,627,851, 3,772,247, 5,248,739 or U.S. Pat. Nos. 5,082,706, 5,319,040, 5,302,685 and 4,935,484.

In the units M, D and T defined previously, R, namely R1 and R2, represents a hydrocarbon-based radical (especially alkyl) containing from 1 to 10 carbon atoms, a phenyl group, a phenylalkyl group or a hydroxyl group.

Finally, the letter Q means a tetrafunctional unit $SiO_{4/2}$ in which the silicon atom is bonded to four hydrogen atoms, which are themselves bonded to the rest of the polymer.

Various silicone resins with different properties may be obtained from these different units, the properties of these polymers varying as a function of the type of monomer (or unit), the nature and number of the radical R, the length of the polymer chain, the degree of branching and the size of the pendent chains.

As silicone resins that may be used in the compositions according to the invention, use may be made, for example, of silicone resins of MQ type, of T type or of MQT type.

MQ Resins:

As examples of silicone resins of MQ type, mention may be made of the alkyl siloxysilicates of formula $[(R1)_3SiO_{1/2}]_x(SiO_{4/2})_y$ (MQ units) in which x and y are integers ranging from 50 to 80, and such that the group R1 represents a radical as defined previously, and is preferably an alkyl group containing from 1 to 8 carbon atoms or a hydroxyl group, preferably a methyl group.

- As examples of solid silicone resins of MQ type of trimethyl siloxysilicate type, mention may be made of those sold under the reference SR1000 by the company General Electric, under the reference TMS 803 by the company Wacker, or under the name KF-7312J by the company Shin-Etsu or DC 749 or DC 593 by the company Dow Corning.
- As silicone resins comprising MQ siloxysilicate units, mention may also be made of phenylalkylsiloxysilicate resins, such as phenylpropyldimethylsiloxysilicate (Silshine 151 sold by the company General Electric). The preparation of such resins is described especially in patent U.S. Pat. No. 5,817,302.

T Resins:

Examples of silicone resins of type T that may be mentioned include the polysilsesquioxanes of formula $(RSiO_{3/2})_x$ (units T) in which x is greater than 100 and such that the group R is an alkyl group containing from 1 to 10 carbon atoms, said polysilsesquioxanes also possibly comprising Si—OH end groups.

Polymethylsilsesquioxane resins that may preferably be used are those in which R represents a methyl group, for instance those sold:

- by the company Wacker under the reference Resin MK, such as Belsil PMS MK: polymer comprising $CH_3SiO_{3/2}$ repeating units (units T), which may also comprise up to 1% by weight of $(CH_3)_2SiO_{2/2}$ units (units D) and having an average molecular weight of about 10 000 g/mol, or
- by the company Shin-Etsu under the reference KR220L, which are composed of units T of formula $CH_3SiO_{3/2}$ and have Si—OH (silanol) end groups, under the reference KR242A, which comprise 98% of units T and 2% of dimethyl units D and have Si—OH end groups, or alternatively under the reference KR251 comprising 88% of units T and 12% of dimethyl units D and have Si—OH end groups.

MQT Resins:

Resins comprising MQT units that are especially known are those mentioned in document U.S. Pat. No. 5,110,890.

A preferred form of resins of MQT type are MQT-propyl (also known as MQTPr) resins. Such resins that may be used in the compositions according to the invention are especially the resins described and prepared in patent application WO 2005/075 542, the content of which is incorporated herein by reference.

The MQ-T-propyl resin preferably comprises the following units:

(i) $(R1_3SiO_{1/2})_a$
(ii) $(R2_2SiO_{2/2})_b$
(iii) $(R3SiO_{3/2})_c$ and
(iv) $(SiO_{4/2})_d$ with R1, R2 and R3 independently representing a hydrocarbon-based radical, especially alkyl, containing from 1 to 10 carbon atoms, a phenyl group, a phenylalkyl group or a hydroxyl group and preferably an alkyl radical containing from 1 to 8 carbon atoms or a phenyl group,
a being between 0.05 and 0.5,
b being between 0 and 0.3,
c being greater than zero,
d being between 0.05 and 0.6,
a+b+c+d=1, and a, b, c and d being mole fractions,
on condition that more than 40 mol % of the groups R3 of the siloxane resin are propyl groups.

Preferably, the siloxane resin comprises the following units:

(i) $(R1_3SiO_{1/2})_a$
(iii) $(R3SiO_{3/2})_c$ and
(iv) $(SiO_{4/2})_d$ with

R1 and R3 independently representing an alkyl group containing from 1 to 8 carbon atoms, R1 preferably being a methyl group and R3 preferably being a propyl group,
a being between 0.05 and 0.5 and preferably between 0.15 and 0.4,
c being greater than zero, preferably between 0.15 and 0.4,
d being between 0.05 and 0.6, preferably between 0.2 and 0.6 or alternatively between 0.2 and 0.55,
a+b+c+d=1, and a, b, c and d being mole fractions,
on condition that more than 40 mol % of the groups R3 of the siloxane resin are propyl groups.

The siloxane resins that may be used according to the invention may be obtained via a process comprising the reaction of:

A) an MQ resin comprising at least 80 mol % of units $(R1_3SiO_{1/2})_a$ and $(SiO_{4/2})_d$,
R1 representing an alkyl group containing from 1 to 8 carbon atoms, an aryl group, a carbinol group or an amino group,
a and d being greater than zero,
the ratio a/d being between 0.5 and 1.5;
and B) a T-propyl resin comprising at least 80 mol % of units $(R3SiO_{3/2})_c$,
R3 representing an alkyl group containing from 1 to 8 carbon atoms, an aryl group, a carbinol group or an amino group,
c being greater than zero,
on condition that at least 40 mol % of the groups R3 are propyl groups,
in which the mass ratio A/B is between 95/5 and 15/85 and preferably the mass ratio A/B is 30/70.

Advantageously, the mass ratio A/B is between 95/5 and 15/85. Preferably, the ratio A/B is less than or equal to 70/30. These preferred ratios have proven to allow comfortable deposits due to the absence of percolation of the rigid particles of MQ resin in the deposit.

Thus, preferably, the silicone resin is chosen from the group comprising:

a) a resin of MQ type, chosen especially from (i) alkyl siloxysilicates, which may be trimethyl siloxysilicates, of formula $[(R1)_3SiO_{1/2}]_x(SiO_{4/2})_y$, in which x and y are integers ranging from 50 to 80, and such that the group R1 represents a hydrocarbon-based radical containing from 1 to 10 carbon atoms, a phenyl group, a phenylalkyl group or a hydroxyl group, and preferably is an alkyl group containing from 1 to 8 carbon atoms, preferably a methyl group, and (ii) phenylalkyl siloxysilicate resins, such as phenylpropyldimethyl siloxysilicate, and/or b) a resin of T type, chosen especially from the polysilsesquioxanes of formula $(RSiO_{3/2})_x$, in which x is greater than 100 and the group R is an alkyl group containing from 1 to 10 carbon atoms, for example a methyl group, said polysilsesquioxanes also possibly comprising Si—OH end groups, and/or c) a resin of MQT type, especially of MQT-propyl type, which may comprise units (i) $(R1_3SiO_{1/2})_a$, (ii) $(R2_2SiO_{2/2})_b$, (iii) $(R3SiO_{3/2})_c$ and (iv) $(SiO_{4/2})_d$,
with R1, R2 and R3 independently representing a hydrocarbon-based radical, especially alkyl, containing from 1 to 10 carbon atoms, a phenyl group, a phenylalkyl group or a hydroxyl group and preferably an alkyl radical containing from 1 to 8 carbon atoms or a phenyl group, a being between 0.05 and 0.5,
b being between 0 and 0.3,
c being greater than zero,
d being between 0.05 and 0.6,
a+b+c+d=1, and a, b, c and d being mole fractions,
on condition that more than 40 mol % of the groups R3 of the siloxane resin are propyl groups.

Preferably, when a phenyl silicone oil is present, it is present in the composition according to the invention in a total content of resin solids ranging from 1% to 40% by weight, preferably ranging from 2% to 30% by weight and better still ranging from 3% to 25% by weight relative to the total weight of the composition.

Lipophilic Gelling Agents

According to one embodiment, the composition according to the invention may comprise at least one gelling agent. The gelling agents that may be used in the compositions according to the invention may be organic or mineral, polymeric or molecular lipophilic gelling agents.

Mineral lipophilic gelling agents that may be mentioned include optionally modified clays, for instance hectorites modified with a $C_{10}$-$C_{22}$ ammonium chloride, for instance hectorite modified with distearyldimethylammonium chloride, for instance the product sold under the name Bentone 38V® by the company Elementis.

Mention may also be made of fumed silica optionally subjected to a hydrophobic surface treatment, the particle size of which is less than 1 μm. Specifically, it is possible to chemically modify the surface of the silica, by chemical reaction generating a reduced number of silanol groups present at the surface of the silica. It is especially possible to substitute silanol groups with hydrophobic groups: a hydrophobic silica is then obtained.

The hydrophobic groups may be:
trimethylsiloxyl groups, which are obtained especially by treating fumed silica in the presence of hexamethyldisilazane. Silicas thus treated are known as "Silica silylate" according to the CTFA (8th edition, 2000). They are sold, for example, under the references Aerosil R812® by the company Degussa, and Cab-O-Sil TS-530® by the company Cabot;
dimethylsilyloxyl or polydimethylsiloxane groups, which are obtained especially by treating fumed silica in the presence of polydimethylsiloxane or dimethyldichlorosilane. Silicas thus treated are known as "Silica Dimethyl Silylate" according to the CTFA (8th edition, 2000). They are sold, for example, under the references Aerosil R972® and Aerosil R974® by the company Degussa, and Cab-O-Sil TS-610® and Cab-O-Sil TS-720® by the company Cabot.

Among the lipophilic gelling agents that may be used in the compositions according to the invention, mention may also be made of fatty acid esters of dextrin, such as dextrin palmitates, especially the products sold under the name Rheopearl TL® or Rheopearl KL® by the company Chiba Flour.

Silicone polyamides of the polyorganosiloxane type may also be used, such as those described in documents U.S. Pat. Nos. 5,874,069, 5,919,441, 6,051,216 and 5,981,680.

These silicone polymers may belong to the following two families:
polyorganosiloxanes comprising at least two groups capable of establishing hydrogen interactions, these two groups being in the chain of the polymer, and/or
polyorganosiloxanes comprising at least two groups capable of establishing hydrogen interactions, these two groups being located on grafts or branches.

Colorants

In a particularly preferred manner, the composition according to the invention comprises at least one dyestuff. Preferably, the dyestuff is present in a content of at least 0.1% by weight relative to the total weight of the composition. The dyestuff may be chosen from pulverulent dyestuffs (especially pigments and nacres) and water-soluble or liposoluble dyestuffs.

For the purposes of the invention, the term "pigments" means white or coloured, mineral or organic particles, which are insoluble in an aqueous solution, and which are intended to colour and/or opacify the resulting makeup film. The pigments also include nacres or nacreous pigments.

The pigments may be present in a proportion of from 0.1% to 15% by weight, especially from 1% to 10% by weight and in particular from 2% to 8% by weight relative to the total weight of the cosmetic composition.

As inorganic pigments that can be used in the invention, mention may be made of titanium oxides, zirconium oxides or cerium oxides, and also zinc oxides, iron oxides or chromium oxides, ferric blue, manganese violet, ultramarine blue and chromium hydrate.

According to one embodiment, titanium oxides and iron oxides are more particularly considered in the invention.

According to one embodiment, a pigment that is suitable for use in the invention may in particular be based on titanium dioxide and iron oxide.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

A pigment that is suitable for use in the invention may comprise a structure that may be, for example, of silica microsphere type containing iron oxide. An example of a pigment having this structure is the product sold by the company Miyoshi under the reference PC Ball PC-LL-100 P, this pigment being constituted of silica microspheres containing yellow iron oxide.

Among the organic pigments that may be used in the invention, mention may be made of carbon black, pigments of D&C type, lakes based on cochineal carmine or on barium, strontium, calcium or aluminium, or alternatively the diketopyrrolopyrroles (DPP) described in documents EP-A-542 669, EP-A-787 730, EP-A-787 731 and WO-A-96/08537.

The terms "nacres" and "nacreous pigments" should be understood as meaning iridescent or non-iridescent coloured particles of any form, especially produced by certain molluscs in their shell, or else synthesized, and which have a colour effect by optical interference.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Among the nacres available on the market, mention may be made of the nacres Timica, Flamenco and Duochrome (based on mica) sold by the company Engelhard, the Timiron nacres sold by the company Merck, the Prestige mica-based nacres, sold by the company Eckart, and the Sunshine synthetic mica-based nacres, sold by the company Sun Chemical.

The nacres may more particularly have a yellow, pink, red, bronze, orange, brown, gold and/or coppery colour or glint.

As illustrations of nacres that may be used in the context of the present invention, mention may be made of gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the names Bronze fine (17384) (Colorona) and Bronze (17353) (Colorona) and by the company Engelhard under the name Super bronze (Cloisonne); the orange nacres sold especially by the company Engelhard under the names Orange 363C (Cloisonne) and Orange MCR 101 (Cosmica) and by the company Merck under the names Passion orange (Colorona) and Matte orange (17449) (Microna); the brown-tinted nacres sold especially by the company Engelhard under the names Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red-tinted nacres with a golden tint sold especially by the company Engelhard under the name Sunstone G012 (Gemtone); the pink nacres sold especially by the company Engelhard under the name Tan opale G005 (Gemtone); the black nacres with a golden tint sold especially by the company Engelhard under the name Nu-antique bronze 240 AB (Timica); the blue nacres sold especially by the company Merck under the name Matte blue (17433) (Microna); the white nacres with a silvery tint sold especially by the company Merck under the name Xirona Silver; and the golden-green pinkish-orange nacres sold especially by the company Merck under the name Indian summer (Xirona), and mixtures thereof.

According to one embodiment variant, a composition of the invention may comprise as pigments a pigment chosen from titanium dioxide, pigments based on titanium dioxide and iron oxide, or pigments based on titanium dioxide, for instance sericite/brown iron oxide/titanium dioxide/silica, or natural mica coated with titanium oxide, and mixtures thereof.

A composition according to the invention may also comprise at least one dyestuff different from the pigments as defined above.

Such a dyestuff may be chosen from organic or inorganic, liposoluble or water-soluble dyestuffs, and materials with a specific optical effect, and mixtures thereof.

A cosmetic composition according to the invention may thus also comprise water-soluble or liposoluble dyes. The liposoluble dyes are, for example, Sudan Red, DC Red 17, DC Green 6, β-carotene, soybean oil, Sudan Brown, DC Yellow 11, DC Violet 2, DC Orange 5 and quinoline yellow. The water-soluble dyes are, for example, beetroot juice or methylene blue.

A cosmetic composition according to the invention may also contain at least one material with a specific optical effect.

This effect is different from a simple conventional hue effect, i.e. a unified and stabilized effect as produced by standard dyestuffs, for instance monochromatic pigments. For the purposes of the invention, the term "stabilized" means lacking an effect of variability of the colour as a function of the angle of observation or alternatively in response to a temperature change.

For example, this material may be chosen from particles with a metallic tint, goniochromatic colouring agents, diffracting pigments, thermochromic agents, optical brighteners, and also fibres, especially interference fibres.

The particles with a metallic tint that may be used in the invention are chosen in particular from:
 particles of at least one metal and/or of at least one metal derivative,
 particles comprising a single-material or multi-material organic or inorganic substrate, at least partially coated with at least one layer with a metallic glint comprising at least one metal and/or at least one metal derivative, and
 mixtures of the said particles.

Among the metals that may be present in the said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr and mixtures or alloys thereof (for example bronzes and brasses) are preferred metals.

The term "metal derivatives" is intended to denote compounds derived from metals, especially oxides, fluorides, chlorides and sulfides.

Illustrations of these particles that may be mentioned include aluminium particles, such as those sold under the names Starbrite 1200 EAC® by the company Siberline and Metalure® by the company Eckart.

Mention may also be made of metal powders of copper or of alloy mixtures such as the references 2844 sold by the company Radium Bronze, metallic pigments, for instance aluminium or bronze, such as those sold under the names Rotosafe 700 from the company Eckart, silica-coated aluminium particles sold under the name Visionaire Bright Silver from the company Eckart, and metal alloy particles, for instance the silica-coated bronze (alloy of copper and zinc) powders sold under the name Visionaire Bright Natural Gold from the company Eckart.

They may also be particles comprising a glass substrate, for instance those sold by the company Nippon Sheet Glass under the name Microglass Metashine.

The goniochromatic colouring agent may be chosen, for example, from multilayer interference structures and liquid-crystal colouring agents.

Examples of symmetrical multilayer interference structures that may be used in the compositions prepared in accordance with the invention are, for example, the following structures: Al/SiO$_2$/Al/SiO$_2$/Al, pigments having this structure being sold by the company DuPont de Nemours; Cr/MgF$_2$/Al/MgF$_2$/Cr, pigments having this structure being sold under the name Chromaflair by the company Flex; MoS$_2$/SiO$_2$/Al/SiO$_2$/MoS$_2$; Fe$_2$O$_3$/SiO$_2$/Al/SiO$_2$/Fe$_2$O$_3$, and Fe$_2$O$_3$/SiO$_2$/Fe$_2$O$_3$/SiO$_2$/Fe$_2$O$_3$, pigments having these structures being sold under the name Sicopearl by the company BASF; MoS$_2$/SiO$_2$/mica-oxide/SiO$_2$/MoS$_2$; Fe$_2$O$_3$/SiO$_2$/mica-oxide/SiO$_2$/Fe$_2$O$_3$; TiO$_2$/SiO$_2$/TiO$_2$ and TiO$_2$/Al$_2$O$_3$/TiO$_2$; SnO/TiO$_2$/SiO$_2$/TiO$_2$/SnO; Fe$_2$O$_3$/SiO$_2$/Fe$_2$O$_3$; SnO/mica/TiO$_2$/SiO$_2$/TiO$_2$/mica/SnO, pigments having these structures being sold under the name Xirona by the company Merck (Darmstadt). By way of example, these pigments may be the pigments of silica/titanium oxide/tin oxide structure sold under the name Xirona Magic by the company Merck, the pigments of silica/brown iron oxide structure sold under the name Xirona Indian Summer by the company Merck and the pigments of silica/titanium oxide/mica/tin oxide structure sold under the name Xirona Caribbean Blue by the company Merck. Mention may also be made of the Infinite Colors pigments from the company Shiseido. Depending on the thickness and the nature of the various coats, different effects are obtained. Thus, with the structure Fe$_2$O$_3$/SiO$_2$/Al/SiO$_2$/Fe$_2$O$_3$, the colour changes from green-golden to red-grey for SiO$_2$ layers of from 320 to 350 nm; from red to golden for SiO$_2$ layers of from 380 to 400 nm; from violet to green for SiO$_2$ layers of from 410 to 420 nm; from copper to red for SiO$_2$ layers of from 430 to 440 nm.

Examples of pigments with a polymeric multilayer structure that may be mentioned include those sold by the company 3M under the name Color Glitter.

Examples of liquid-crystal goniochromatic particles that may be used include those sold by the company Chenix and also the product sold under the name Helicone® HC by the company Wacker.

The dyestuffs, in particular the pigments treated with a hydrophobic agent, may be present in the composition in a content ranging from 0.1% to 50% by weight, preferably ranging from 0.5% to 30% by weight and preferentially ranging from 1% to 20% by weight, relative to the total weight of the composition.

Fillers:

The composition according to the invention may comprise at least one filler.

For the purposes of the present invention, the term "filler" denotes solid particles of any form, which are in an insoluble form and dispersed in the medium of the composition, even at temperatures that may be up to the melting point of all the fatty substances of the composition.

Generally, the fillers used according to the invention are colourless or white, namely non-pigmentary, i.e. they are not used to give a particular colour or shade to the composition according to the invention, even though their use may inherently lead to such a result. These fillers serve especially to modify the rheology or the texture of the composition.

In this respect, they are different from nacres, organic pigmentary materials, for instance carbon black, pigments of D&C type, and lakes based on cochineal carmine or on barium, strontium, calcium or aluminium, and inorganic pigmentary materials, for instance titanium dioxide, zirconium oxide or cerium oxide, and also iron oxides (black, yellow or red), chromium oxide, manganese violet, ultramarine blue, chromium hydrate and ferric blue, which are, themselves, used to give a shade and coloration to the compositions incorporating them.

For the purposes of the invention, such compounds are not covered by the definition of fillers, which thus covers non-pigmentary fillers, which may be organic or inorganic.

The non-pigmentary fillers used in the compositions according to the present invention may be of lamellar, globular or spherical form, of fibre type, or of any intermediate form between these defined forms.

The size of the particles, i.e. their granulometry, is chosen so as to ensure the good dispersion of the fillers in the composition according to the invention. The granulometry of the particles may be distributed within the range from 5 µm to 10 nm and in particular from 10 µm to 10 nm.

The fillers according to the invention may or may not be surface-coated, in particular surface-treated with silicones, amino acids, fluoro derivatives or any other substance that promotes the dispersion and compatibility of the filler in the composition.

Mineral Fillers

For the purposes of the present invention, the terms "mineral" and "inorganic" are used interchangeably.

Among the non-pigmentary mineral fillers that may be used in the compositions according to the invention, mention may be made of talc, mica, silica, perlite, which is especially commercially available from the company World Minerals Europe under the trade name Perlite P1430, Perlite P2550 or Perlite P204, kaolin, precipitated calcium carbonate, magnesium carbonate, magnesium hydrogen carbonate, hydroxyapatite, boron nitride, hollow silica microspheres (Silica Beads® from Maprecos), and glass or ceramic microcapsules, and mixtures thereof.

According to one embodiment, the cosmetic composition according to the invention comprises at least one non-pigmentary mineral filler chosen from the group comprising kaolin, talc, silica, perlite and clay, and mixtures thereof.

Organic Fillers

Among the organic fillers that may be mentioned are polyamide powder (Orgasol® Nylon® from Atochem), poly-β-alanine powder and polyethylene powder, lauroyllysine, starch, tetrafluoroethylene polymer powders (Teflon®), hollow polymer microspheres such as those of polyvinylidene chloride/acrylonitrile, for instance Expancel® (Nobel Industrie) or of acrylic acid copolymer (such as Polytrap (Dow Corning)), acrylate copolymers, PMMA, 12-hydroxystearic acid oligomer stearate and silicone resin microbeads (for example Tospearls® from Toshiba), magnesium carbonate, magnesium hydrogen carbonate, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate, and mixtures thereof.

For the purposes of the present invention, the organic fillers are different from the pigments.

They may also be particles comprising a copolymer, the said copolymer comprising trimethylol hexyl lactone. In particular, it may be a copolymer of hexamethylene diisocyanate/trimethylol hexyl lactone. Such particles are especially commercially available, for example, under the name Plastic Powder D-400® or Plastic Powder D-800® from the company Toshiki.

According to one embodiment, a composition of the invention may comprise at least one filler chosen from talc, silica, starch, clay, kaolin and perlite, and mixtures thereof.

One or more dispersants may be used, where appropriate, to protect the dispersed fillers or particles against aggregation or flocculation. They may be added independently of the solid fillers or particles or in the form of a colloidal dispersion of particles.

The concentration of dispersants is chosen so as to obtain satisfactory dispersion of the solid particles (without flocculation).

This dispersant may be a surfactant, an oligomer, a polymer or a mixture of several thereof, bearing one or more functionalities with strong affinity for the surface of the particles to be dispersed. In particular, poly(12-hydroxystearic acid) esters are used, such as poly(12-hydroxystearic acid) stearate with a molecular weight of about 750 g/mol, such as the product sold under the name Solsperse 21 000® by the company Avecia, esters of poly(12-hydroxystearic acid) with polyols such as glycerol or diglycerol, such as polyglyceryl-2 dipolyhydroxystearate (CTFA name) sold under the reference Dehymuls PGPH® by the company Henkel (or diglyceryl poly(12-hydroxystearate)), or alternatively poly(12-hydroxystearic acid), such as the product sold under the reference Arlacel P100 by the company Uniqema, and mixtures thereof.

As other dispersants that may be used in the composition of the invention, mention may be made of quaternary ammonium derivatives of polycondensate fatty acids, for instance Solsperse 17 000® sold by the company Avecia, and mixtures of polydimethylsiloxane/oxypropylene such as those sold by the company Dow Corning under the references DC2-5185 and DC2-5225 C.

Preferably, the composition according to the invention comprises at least one compound chosen from a hydrocarbon-based oil and/or a pasty fatty substance and/or a dyestuff and/or a filler and/or a lipophilic gelling agent and/or a silicone resin; and a mixture thereof.

Usual Additional Cosmetic Ingredients

The composition according to the invention may also comprise any common cosmetic ingredient, which may be chosen especially from film-forming polymers, antioxidants, fragrances, preserving agents, neutralizers, surfactants, sunscreens, vitamins, moisturizers, self-tanning compounds, antiwrinkle active agents, emollients, hydrophilic or lipophilic active agents, free-radical scavengers, deodorants, sequestrants, film-forming agents and semicrystalline polymers, and mixtures thereof.

Needless to say, a person skilled in the art will take care to select the optional additional ingredients and/or the amount thereof such that the advantageous properties of the composition according to the invention are not, or are not substantially, adversely affected by the envisioned addition.

The compositions according to the invention may be in any common acceptable form for a cosmetic composition. They may thus be in the form of a suspension, a dispersion especially of oil in water by means of vesicles; an oil-in-water, water-in-oil or multiple emulsion; a cast or moulded solid especially as a stick or a dish, or a compacted solid.

A person skilled in the art may select the appropriate galenical form, and also the method for preparing it, on the basis of his general knowledge, taking into account firstly the nature of the constituents used, especially their solubility in the support, and secondly the intended application of the composition.

Preferably, the composition according to the invention comprises less than 3% and better still less than 1% by weight of water relative to the total weight of the composition. Even more preferably, the composition is totally anhydrous. The term "anhydrous" especially means that water is preferably not deliberately added to the composition, but may be present in trace amount in the various compounds used in the composition.

According to one preferred embodiment, the composition according to the invention is a lipstick.

According to one particular mode, the composition is in solid form at 20° C. In the case of a lipstick, it may be a stick of lipstick or a lipstick cast in a dish, for example.

The term "solid" refers to a composition whose hardness, measured according to the following protocol, is greater than or equal to 30 $Nm^{-1}$ at a temperature of 20° C. and at atmospheric pressure (760 mmHg).

Protocol for Measuring the Hardness:

The hardness of the composition is measured according to the following protocol:

The stick of lipstick is stored at 20° C. for 24 hours before measuring the hardness.

The hardness may be measured at 20° C. via the "cheese wire" method, which consists in transversely cutting a wand of product, which is preferably a circular cylinder, by means of a rigid tungsten wire 250 µm in diameter, by moving the wire relative to the stick at a speed of 100 mm/minute.

The hardness of the samples of compositions of the invention, expressed in $Nm^{-1}$, is measured using a DFGHS2 tensile testing machine from the company Indelco-Chatillon.

The measurement is repeated three times and then averaged. The average of the three values read using the tensile testing machine mentioned above, noted Y, is given in grams. This average is converted into newtons and then divided by L which represents the longest distance through which the wire passes. In the case of a cylindrical wand, L is equal to the diameter (in metres).

The hardness is converted into $Nm^{-1}$ by the equation below:

$$(Y \times 10^{-3} \times 9.8)/L$$

For a measurement at a different temperature, the stick is stored for 24 hours at this new temperature before the measurement.

According to this measuring method, the composition according to the invention preferably has a hardness at 20° C. and at atmospheric pressure of greater than or equal to 40 $Nm^{-1}$ and preferably greater than 50 $Nm^{-1}$.

Preferably, the composition according to the invention especially has, according to this measuring method, a hardness at 20° C. of less than 500 $Nm^{-1}$, especially less than 400 $Nm^{-1}$ and preferably less than 300 $Nm^{-1}$.

A solid composition according to the invention will advantageously have, according to this measuring method, a hardness at 20° C. and at atmospheric pressure ranging from 45 to 100 $Nm^{-1}$ and preferentially from 55 to 85 $Nm^{-1}$.

The compositions in accordance with the invention may be used for caring for or making up keratin materials such as the skin, the eyelashes, the eyebrows, the nails or the lips, and more particularly for making up the lips, the eyelashes and/or the face.

According to one preferred embodiment, the composition according to the invention is a lipstick, in particular in the form of a stick.

They may thus be in the form of a care and/or makeup product for bodily or facial skin, the lips, the eyelashes, the eyebrows or the nails; an antisun or self-tanning product; they may advantageously be in the form of a makeup composition, especially a mascara, an eyeliner, a lipstick, a face powder, an eyeshadow or a foundation.

A subject of the invention is also a cosmetic process for treating keratin materials, especially bodily or facial skin, the lips and/or the eyelashes, comprising the application to the said materials of a cosmetic composition as defined previously.

This process according to the invention makes it possible especially to care for or make up the said keratin materials, in particular the lips, by applying a composition, especially a lipstick composition.

The invention is illustrated in greater detail in the following non-limiting exemplary embodiments.

EXAMPLES 1 AND 2

Solid Lipsticks

The following solid lipstick compositions were prepared:

| Cosmetic type | US INCI and commercial reference | Composition 1 according to the invention (weight %) | Composition 2 according to the invention (weight %) |
|---|---|---|---|
| Dye | Yellow 5 lake | 0.86 | 0.86 |
| Dye | Iron oxides (and) iron oxides | 0.96 | 0.96 |
| Dye | Blue 1 lake | 0.2 | 0.2 |
| Dye | Red 7 | 0.45 | 0.45 |
| Dye | Titanium dioxide | 0.2 | 0.2 |
| Nacre | Mica (and) titanium dioxide | 4.3 | 4.3 |
| Wax | Microcrystalline wax (Microwax HW from Paramelt) | 10 | 10 |
| Wax | C30-45 Alkyl dimethicone (SF 1642 from Momentive Performance Materials) | 2.5 | 2.5 |
| Fatty substance | Hydrogenated cocoglycerides (Softisan 100 from Sasol) | 10 | 10 |
| Supramolecular compound | Jarcol 24 (51.5% in isododecane: Supramolecular compound 12 prepared above) | 26.45 | 26.45 |
| Silicone resin | Trimethyl siloxysilicate (SR 1000 from Momentive) | — | 5 |
| Silicone | Phenyl trimethicone (Dow Corning 556 Cosmetic Grade Fluid from Dow Corning) | 17.63 | 16.38 |
| Silicone | Trimethylsiloxyphenyl Dimethicone (Wacker-Belsil PDM 1000 from Wacker) | 26.45 | 22.70 |
| | TOTAL: | 100 | 100 |
| | HARDNESS | 73.1 Nm$^{-1}$ | 77.9 Nm$^{-1}$ |

Preparation Protocol:

In a first stage, the pigments were ground in a three-roll mill in part of the phenyl trimethicone.

The rest of the liposoluble ingredients (with the exception of the waxes) were then mixed in a heating pan at a temperature of about 45° C. using a Rayneri blender. Once the mixture was homogeneous, the composition was heated to 98° C. and the waxes were added. Once the fatty phase was homogeneous, the ground pigmentary material and the nacres, if present, were incorporated into the mixture.

Finally, the composition was poured into moulds (preheated to 40° C.) to produce sticks 11.6 mm in diameter, and the whole was left to cool in a freezer for the time necessary to achieve efficient work-hardening (about 1 hour). The sticks were then left to stand at room temperature for 24 hours.

Evaluation:

For compositions 1 and 2, solid homogeneous sticks (which do not break during application) and which are stable at 23° C. and at 45° C. for 1 month (no exudation or phase separation is observed) are obtained. The sticks obtained are easy to apply to the lips (easy glidance and stick erosion) and the deposit obtained is homogeneous and of uniform thickness.

After application of the compositions to the lips, the following results are observed:

For each of the compositions 1 and 2, the makeup deposits obtained are homogeneous, comfortable, long-wearing and non-tacky. Furthermore, for each of the deposits, a satisfactory level of gloss (silky deposit) is obtained, immediately after application and 1 hour after application.

EXAMPLE 3

Study of the Compatibility of the Oils with the Supramolecular Compound (Jarcol 24: 51.5% in Isododecane: Supramolecular Compound 12 Prepared Above)

The supramolecular compound and each non-volatile silicone oil were mixed together in the respective weight ratios 30/70, 50/50 and 70/30, and the appearance of the mixture at room temperature was observed.

The oil is said to be "compatible" with the supramolecular compound when the mixture obtained is liquid, transparent and colourless.

The oil is said to be "incompatible" with the supramolecular compound when the mixture obtained is a two-phase mixture.

The results are given in the table below:

| Compatibility of the supramolecular compound with the following silicone oils | | | In the ratios supramolecular compound/silicone oil | | |
|---|---|---|---|---|---|
| | | | 30/70 | 50/50 | 70/30 |
| Commercial reference | US INCI Name | Structural formula | compat-ibility | compat-ibility | compat-ibility |
| DC556 from Dow Corning | Phenyl trimethicone 20 cSt | 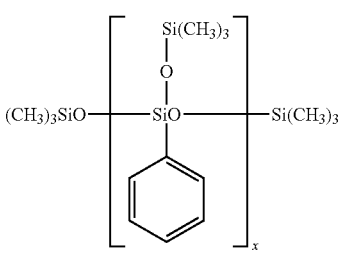 | Yes | Yes | Yes |
| KF-56A from Shin-Etsu | Diphenylsiloxyphenyl trimethicone | 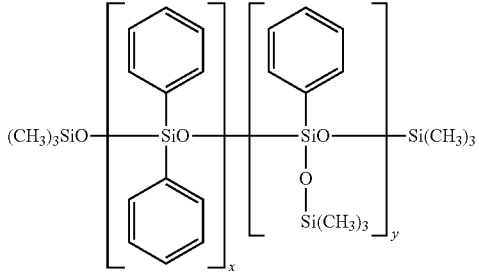 | Yes | Yes | Yes |
| PH1555 from Dow Corning | Trimethyl pentaphenyl trisiloxane 175 cSt | 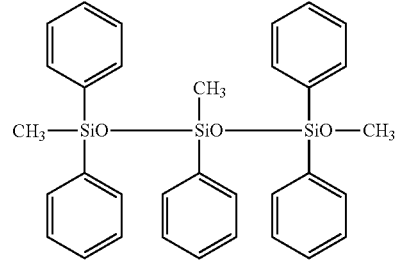 | No | Yes | Yes |
| Belsil PDM1000 from Wacker | Trimethyl siloxyphenyl dimethicone 1000 cSt | 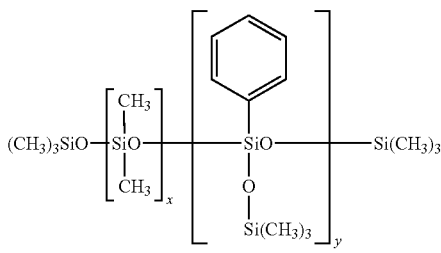 | No | No | No |
| Silshine 151 from Momentive Performance Materials | Phenylpropyldimethyl siloxy silicate | 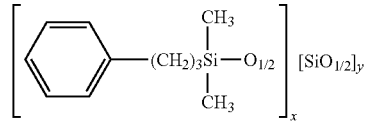 | Yes | Yes | Yes |

| Compatibility of the supramolecular compound with the following silicone oils | | | In the ratios supramolecular compound/silicone oil | | |
|---|---|---|---|---|---|
| | | | 30/70 | 50/50 | 70/30 |
| Commercial reference | US INCI Name | Structural formula | compat- ibility | compat- ibility | compat- ibility |
| KF-54 from Shin-Etsu | Diphenyl dimethicone 400 cSt | $(CH_3)_3SiO-\left[\begin{array}{c}CH_3\\|\\SiO\\|\\CH_3\end{array}\right]_x\left[\begin{array}{c}Ph\\|\\SiO\\|\\Ph\end{array}\right]_y Si(CH_3)_3$ | No | No | No |

EXAMPLE 4

Solid Lipstick (Stick)

The following solid lipstick composition was prepared:

| US INCI name and commercial reference | Amount (%) | Phase |
|---|---|---|
| (Jarcol 24: 51.5% in isododecane: Supramolecular compound 12 prepared above) | 21 | A1 |
| Phenyl trimethicone (DC 556 Cosmetic Grade Fluid from Dow Corning) | 32.60 | |
| Trimethylsiloxyphenyl Dimethicone (Wacker-Belsil PDM 1000 from Wacker) | 18.90 | A2 |
| Polyethylene wax (Performalene 500L polyethylene from New Phase Technologies) | 8.00 | B |
| Phenyl trimethicone (DC 556 Cosmetic Grade Fluid from Dow Corning) | 11.50 | C |
| Titanium dioxide | 1.82 | |
| Red 7 | 1.51 | |
| Red 28 lake | 1.26 | |
| Yellow 6 lake | 2.05 | |
| Iron oxides | 1.36 | |

Preparation Protocol:

In a first stage, the pigments of phase C were ground in a three-roll mill in part of the phenyl trimethicone.

The ingredients of phase A1 were mixed together in a heating pan and brought to a temperature of 100° C. while stirring with a Rayneri blender. Phase B was then introduced very cautiously, the mixture was heated for 5 minutes, and the wax was then added and mixed in until totally dissolved. The ground pigmentary material obtained previously was gradually introduced and homogenized fully with heating for 15 minutes.

Finally, the composition was poured into moulds (preheated to 40° C.) to produce sticks 11.6 mm in diameter, and the whole was left to cool in a freezer for the time necessary to achieve efficient work-hardening (about 1 hour). The sticks were then left to stand at room temperature (20° C.) for 24 hours.

Composition Hardness

The hardness of the composition is measured according to the following protocol:

The stick of lipstick is stored at 20° C. for 24 hours before measuring the hardness.

The hardness may be measured at 20° C. via the "cheese wire" method, which consists in transversely cutting a wand of product, which is preferably a circular cylinder, by means of a rigid tungsten wire 250 μm in diameter, by moving the wire relative to the stick at a speed of 100 mm/minute.

The hardness of the samples of compositions of the invention, expressed in $Nm^{-1}$, is measured using a DFGHS2 tensile testing machine from the company Indelco-Chatillon. The measurement is repeated three times and then averaged. The average of the three values read using the tensile testing machine mentioned above, noted Y, is given in grams. This average is converted into newtons and then divided by L which represents the longest distance through which the wire passes. In the case of a cylindrical wand, L is equal to the diameter (in metres).

The hardness is converted into $Nm^{-1}$ by the equation below:

$$(Y \times 10^{-3} \times 9.8)/L$$

For a measurement at a different temperature, the stick is stored for 24 hours at this new temperature before the measurement.

| Hardness (Conditioning Ø 11.6 mm) |
|---|
| 74 ± 6 g |
| 62 ± 4 N · m$^{-1}$ |

Evaluation

Solid homogeneous sticks (which do not break during application) and which are stable at 23° C. and at 45° C. for 1 month (no exudation or phase separation is observed) are obtained. The sticks obtained are easy to apply to the lips (easy glidance and stick erosion) and the deposit obtained shows an acceptable level of gloss (silky deposit), immediately after application and 1 hour after application, and is homogeneous, comfortable and of uniform thickness.

A sensory evaluation of the cosmetic properties on application (ease of application, glidance, absence of tack) and over time (colour remanence, no drying-out effect) was performed on a panel of 10 regular users of long-wearing lipstick in stick form.

For all the uses, the composition is easy to apply (glides well on the lips) and has a long-wearing effect (remanent colour effect). The deposited film is light to wear, non-greasy, non-tacky and comfortable; it does not dry out the lips, or even has the effect of moisturizing them.

EXAMPLE 5

Solid Lipstick (Stick)

The following lipstick composition was prepared according to the protocol described in Example 4.

| Chemical name and commercial reference | Amount (%) | Phase |
|---|---|---|
| Jarcol 24 (55.6% in isododecane) (supramolecular compound 12 prepared previously) | 21 | A1 |
| Phenyl trimethicone (Dow Corning 556 Cosmetic Grade Fluid from Dow Corning) (viscosity 20 cSt) | 20.53 | |
| C12-15 Alkyl benzoate (Tegosoft TN from Evonik Goldschmidt) | 10.67 | |
| Trimethylsiloxyphenyl dimethicone (Wacker-Belsil PDM 1000 from Wacker) | 18.30 | A2 |
| Polyethylene wax (Performalene 500L polyethylene from New Phase Technologies) | 10.00 | B |
| Phenyl trimethicone (Dow Corning 556 Cosmetic Grade Fluid from Dow Corning) (viscosity 20 cSt) | 11.50 | C |
| Titanium dioxide | 1.82 | |
| Red 7 (Unipure Red LC 3079 OR from LCW (Sensient)) | 1.51 | |
| Red 28 lake | 1.26 | |
| Yellow 6 lake | 2.05 | |
| Iron oxides | 1.36 | |

The hardness of the composition was measured as described in the preceding Example 4: 74±5 N·m$^{-1}$.

In evaluation on testers, the texture glides easily on application. The deposit is fine, glossy, comfortable and non-tacky. The remanence of the colour over time is good.

Compositions 4 and 5, in which the phenyl trimethicone is in a higher content than the trimethylsiloxyphenyl dimethicone, and the content of agents for structuring the liquid fatty phase is less than 20%, compared with the compositions of Examples 1 and 2 described previously, make it possible to further improve the cosmetic properties after application to the lips, in particular in terms of non-tacky effect, fineness of the deposited film and homogeneity of the makeup result.

The invention claimed is:

1. A solid lipstick composition comprising, in a cosmetically acceptable medium:
   (a) a supramolecular compound in an amount of 40 to 20% by weight of active material, relative to the total weight of the composition having the formula:

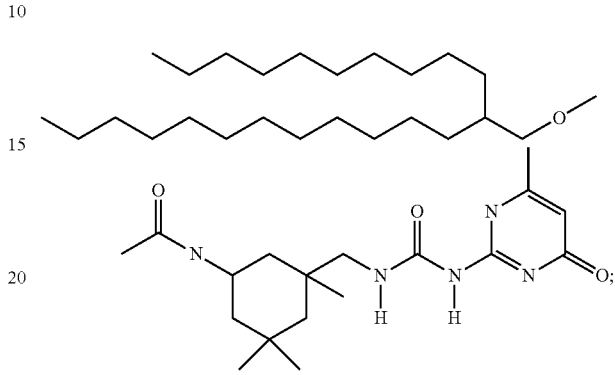

(b) two distinct non-volatile silicone oils in a total content ranging from 40% to 65% by weight relative to the total weight of the composition, wherein a first non-volatile silicone oil is phenyl trimethicone and a second non-volatile silicone oil is trimethylsiloxyphenyl dimethicone
   the first non-volatile silicone oil is present in a content greater than or equal to the second non-volatile silicone oil; and
   (c) polyethylene wax in a content of less than or equal to 20% by weight relative to the total weight of the composition,
   wherein the solid lipstick composition does not comprise a film former and
   wherein the solid lipstick composition does not break during application and which is stable at 23° C. and at 45° C. for 1 month defined by no observable exudation or phase separation.

2. The solid lipstick composition of claim 1, comprising at least one member selected from the group consisting of a hydrocarbon-based oil, a pasty fatty substance, a dyestuff and a filler.

3. The cosmetic composition of claim 1, wherein the supramolecular compound is present in the composition in an amount of 8% and 13% by weight of active material relative to the total weight of the composition.

4. A process for applying a lipstick to lips, the process comprising applying the solid lipstick composition of claim 1 to the lips.

* * * * *

UNITED STATES PATENT AND TRADEMARK OFFICE
CERTIFICATE OF CORRECTION

PATENT NO. : 10,653,600 B2
APPLICATION NO. : 14/128989
DATED : May 19, 2020
INVENTOR(S) : Nathalie Geffroy et al.

Page 1 of 1

It is certified that error appears in the above-identified patent and that said Letters Patent is hereby corrected as shown below:

In the Claims

In Column 94, Line 7, Claim 1, "40" should read -- 4% --.

Signed and Sealed this
Twenty-fifth Day of August, 2020

Andrei Iancu
*Director of the United States Patent and Trademark Office*